US009670506B2

(12) United States Patent
Pantaleo et al.

(10) Patent No.: US 9,670,506 B2
(45) Date of Patent: Jun. 6, 2017

(54) MODIFIED IMMUNIZATION VECTORS

(75) Inventors: Giuseppe Pantaleo, Lausanne (CH);
Thierry Calandra, Grandvaux (CH);
Alexandre Harari, Lausanne (CH);
Thierry Roger, Pully (CH); Mariano Esteban, Torrelodones (ES); Bertram Jacobs, Tempe, AZ (US); Karen Kibler, Tempe, AZ (US); Cornelius Melief, Leiden (NL); Rafick-Pierre Sekaly, Port St. Lucie, FL (US); Elias Haddad, Port St. Lucie, FL (US);
James Tartaglia, Nazareth, PA (US)

(73) Assignees: CONSEJO SUPERIOR DE INVESTIGACIONES CIENTIFICAS, Madrid (ES); ACADEMISCH ZIKENHUIS LEIDEN, Leiden (NL); CENTRE HOSPITALIER UNIVERSITAIRE VAUDOIS, Lausanne (CH); UNIVERSITE DE MONTREAL, Montreal, Quebec (CA); ARIZONA BOARD OF REGENTS, Phoenix, AZ (US); SANOFI PASTEUR LIMITED, Toronto, Ontario (CA)

( * ) Notice: Subject to any disclaimer, the term of this patent is extended or adjusted under 35 U.S.C. 154(b) by 335 days.

(21) Appl. No.: 13/266,282

(22) PCT Filed: Apr. 29, 2010

(86) PCT No.: PCT/US2010/032966
§ 371 (c)(1),
(2), (4) Date: Jan. 6, 2012

(87) PCT Pub. No.: WO2010/127115
PCT Pub. Date: Nov. 4, 2010

(65) Prior Publication Data
US 2012/0328653 A1 Dec. 27, 2012

Related U.S. Application Data

(60) Provisional application No. 61/174,024, filed on Apr. 30, 2009.

(51) Int. Cl.
C12N 15/63 (2006.01)
C12N 15/86 (2006.01)
A61K 39/00 (2006.01)

(52) U.S. Cl.
CPC ...... *C12N 15/86* (2013.01); *A61K 2039/5256* (2013.01); *C12N 2710/24143* (2013.01)

(58) Field of Classification Search
None
See application file for complete search history.

(56) References Cited

U.S. PATENT DOCUMENTS

| | | |
|---|---|---|
| 4,923,808 A | 5/1990 | Matteucci et al. |
| 5,185,146 A | 2/1993 | Altenburger et al. |
| 5,494,807 A | 2/1996 | Paoletti et al. |
| 5,505,941 A | 4/1996 | Paoletti et al. |
| 5,756,103 A | 5/1998 | Paoletti et al. |
| 5,762,938 A | 6/1998 | Paoletti et al. |
| 5,766,598 A | 6/1998 | Paoletti et al. |
| 5,833,975 A | 11/1998 | Paoletti et al. |
| 5,942,235 A | 8/1999 | Paoletti et al. |
| 5,972,597 A | 10/1999 | Paoletti et al. |
| 5,990,091 A | 11/1999 | Tartaglia et al. |
| 6,001,349 A | 12/1999 | Panicali et al. |
| 6,004,777 A | 12/1999 | Tartaglia et al. |
| 6,130,066 A | 10/2000 | Tartaglia et al. |
| 6,183,750 B1 | 2/2001 | Paoletti et al. |
| 6,265,189 B1 | 7/2001 | Paoletti et al. |
| 6,319,496 B1 | 11/2001 | Panicali et al. |
| 6,340,462 B1 | 1/2002 | Paoletti et al. |
| 6,440,422 B1 | 8/2002 | Sutter et al. |
| 6,596,279 B1 | 7/2003 | Paoletti et al. |
| 6,780,407 B1 | 8/2004 | Paoletti et al. |
| 7,049,145 B2 | 5/2006 | Erfle et al. |
| 7,255,862 B1 | 8/2007 | Tartaglia et al. |
| 7,323,557 B2 | 1/2008 | Wagner et al. |
| 7,332,588 B1 | 2/2008 | Wagner et al. |
| 7,431,929 B2 | 10/2008 | Jacobs et al. |
| 7,473,536 B2 | 1/2009 | Howle et al. |
| 7,473,762 B2 | 1/2009 | Foster et al. |
| 2009/0060947 A1 | 3/2009 | Tartalia et al. |

FOREIGN PATENT DOCUMENTS

WO WO 2007/132052 A1 11/2007

OTHER PUBLICATIONS

Verardi et al. Vaccinia virus Vectors with an Inactivated Gamma Interferon Receptor Homolog Gene (B8R) Are Attenuated In Vivo without a Concomitant Reduction in Immunogenicity. Journal of Virology 2001, vol. 75, No. 1, pp. 11-18.*
Jentarra et al. Vaccinia viruses with mutations in the E3L gene as potential replication-competent, attenuated vaccines: scarification vaccination. Vaccine Jun. 2, 2008; vol. 26, No. 23, pp. 2860-2872.*
Verardi et al. Vaccinia virus vectors with an inactivated gamma interferon receptor homolog gene (B8R) are attenuated in vivo without a concomitant reduction in immunogenicity. Journal of Virology 2001, vol. 75(1), pp. 11-18.*
Harari et al. An HIV-1 Clade C DNA prime, NYVAC boost vaccine regimen induces reliable, polyfunctional, and long-lasting T cell responses. Journal of Experimental Medicine Jan. 21, 2008, vol. 205, No. 1, p. 63-77.*
Su et al. Characterization of a virtually full-length human immunodeficiency virus type 1 genome of a prevalent intersubtype (C/B') recombinant strain in China. Journal of Virology, Dec. 2000, vol. 74, No. 23, p. 11367-11376.*
Ahlers, et al., Mechanisms of cytokine synergy essential for vaccine protection against viral challenge. Int. Immunol. 13(7), 897-908 (2000).
Burton, et al. HIV vaccine design and the neutralizing antibody problem. Nat. Immunol. 5(3), 233-236 (2004).

(Continued)

*Primary Examiner* — Benjamin P Blumel
(74) *Attorney, Agent, or Firm* — Patrick J. Halloran

(57) ABSTRACT

The disclosure relates to recombinant vectors and methods for using the same. In certain embodiments, the recombinant vectors are immunogenic.

17 Claims, 21 Drawing Sheets

(56) References Cited

OTHER PUBLICATIONS

Caputo, et al. Recent Advances in the Development of HIV-1 Tat-Based Vaccines. Current HIV Res. 2, 357-376 (2004).
Cerebre, et al. Phase I clinical trial safety of DNA- and modified virus Ankara-vectored human immunodeficiency virus type 1 (HIV-1) vaccines adminstered alone and in a prime-boost regime to healthy HIV-1 unifected volunteers, Vaccine, 24, 417-425 (2006).
Chiklikar, et al. Inverted terminal repeat sequences of adeno-associated virus enhance the antibody and CD8+ response to a HIV-1 p55Gag/LAMP DNA vaccine chimera. Virology, 323, 220-232 (2004).
Desrosiers, et al. Prospects for an AIDS vaccine. Nat. Med. 10(3), 221-223 (2004).
Gallo, R. The end or the beginning, of the drive to an HIV-preventive vaccine: a view from over 20 years. The Lancet, 366, 1894-1898 (2005).
Goonetilleke, et al. Induction of Multifunctional Human Immunodeficiency Virus Type 1 (HIV-1)-Specific T Cells Capable of Proliferation in Healthy Subjects by Using a Prime-Boost Regimen of DNA- and Modified *Vaccinia virus* Ankara-Vectored Vaccines Expressing HIV-1 Gag Coupled to CD8+ T-Cell Epitopes. J. Virol, 80(1), 4717-4728 (2006).
Harari, et. al. An HIV-1 clade C DNA prime, NYVAC boost vaccine regimen induces reliable, polyfunctional, and long-lasting T cell responses, J. Exp. Med, 205(1), 63-77 (2008).
Hei et al. Potentiation of Simian Immunodeficiency Virus (SIV)-Specific CD4+ and CD8+ T Cell. Responses by a DNA-SIV and NYVAC-SIV Prime/Boost Regimen. J. Immunol. 167. 7180-7191 (2001).
Kumar, et al. Development of a candidate DNA/MVA HIV-1 subtype C vaccine for India. Vaccine, 24, 2585-2593 (2006).
McCormack, et al. EV02: A Phase I trial to compare the safety and immunogenicity of HIV DNA-C prime-NYVAC-C boost to NYVAC-C alone. Vaccine, 26, 3162-3174 (2008).
Mwau, et al. A human immunodeficiency virus 1 (HIV-1) clade A vaccine in clinical trials: stimulation of HIV-specific T-cell responses by DNA and recombinant modified *Vaccinia virus* Ankara (MVA) vaccines in humans. J, Gen. Virol, 85, 911-919 (2004).
Naylor, et al. Preclinical and Clinical Studies on Immunogenicity and Safety of the HIV-1 p17-Based Synthetic Peptide AIDS Vaccine-HGP-30-KLH, Int. J. Immunopharmacol. 13(1), 117-127 (1991).
Rodenburg, et al, GenBank Accession No. AAK30988 (2001).
Sandstrom, et al. Therapeutic immunization with recombinant gp160 in HIV-1 infection: a randomized double-blind placebo-controlled trial. The Lancet, 353; 1735-1742 (1999).
Su, et al. Characterization of a Virtually Full-Length Human Immunodeficiency Virus Type 1 Genome of a Prevalent Intersubtype (C/B') Recombinant Strain in China. J. Virol, 74, 11367-76 (2000).
Tongcharoen, et al. A phase 1/2 comparative vaccine trial of the safety and immunogenicity of a CRF01_AE (subtype E) candidate vaccine: ALVAC-HIV (vCP1521) prime with oligomeric gp160 (92TH023/LAI-DID) or bivalent gp120 (CM235/SF2) boost. J. Acquir, Immune Defic. Syndr. 46(1), 48-55 (2007).
Barnett, et al. Vaccination with HIV-1 gp120 DNA induces immune responses that are boosted by a recombinant gp120 protein subunit. Vaccine, 15(8): 869-873 (1997).
Aarts, et al. Vector-based Vaccine/Cytokine Combination Therapy to Enhance Induction of Immune Responses to a Self-Antigen and Antitumor Activity. Cancer Res. 62: 5770-5777 (Oct. 15, 2002).
Alcami, et al. Viral Mimicry of Cytokines. Chemokines and Their Receptors, Nat. Rev, Immunol, 3, 36-50 (2003).
Alcami, et al. A Soluble Receptor for Interleukin-1b Encoded by *Vaccinia virus*: A Novel Mechanism of Virus Modulation of the Host Response to Infection. Cell, 71, 153-167 (1992).
International Search Report for PCT/US2010/032966, Nov. 4, 2010, Centre Hospitalier Universitaire Vaudois Lausanne, et al.
Written Opinion for PCT/US2010/032966, Nov. 4, 2010, Centre Hospitalier Universitaire Vaudois Lausanne, et al.

International Preliminary Examination Report for PCT/US2010/032966, Nov. 4, 2010, Centre Hospitalier Universitaire Vaudois Lausanne, et al.
Alcami, et al. *Vaccinia, Cowpox,* and *Camelpox viruses* Encode Soluble Gamma Interferon Receptors with Novel Broad Species Specificity. J. Virol, 69, 4633-4639 (1995).
Alcami, et al. A mechanism for the inhibition of fever by a virus. Proc. Natl. Acad. Sci. U S A, 93, 11029-11034 (1996).
Alcami, et al. The *Vaccinia virus* Soluble Alpha/Beta Interferon (IFN) Receptor Binds to the Cell Surface and Protects Cells from the Antiviral Effects of IFN. J. Virol. 74, 11230-11239 (2000).
Alcami, et al. *Vaccinia virus* strains Lister, USSR and Evans express soluble and cell-surface tumor necrosis factor receptors, J. Gen, Virol., 80, 949-959 (1999).
Antoine, et al. The Complete Genomic Sequence of the Modified *Vaccinia* Ankara Strain: Comparison with Other Orthopoxviruses. Virology, 244, 365-396 (1998).
Benson, et al. Recombinant. Vaccine-Induced Protection against the Highly Pathogenic Simian Immunodeficiency Virus SIVmac251: Dependence on Route of Challenge Exposure. J. Virol., 72, 4170-4182 (1998).
Blanchard, et al. Modified *Vaccinia virus* Ankara undergoes limited replication in human cells and lacks several immunomodulatory proteins: implications for use as a human vaccine. J. Gen. Virol., 79 (Pt 5), 1159-1167 (1998).
Bowie, et al. A46R and A52R from *Vaccinia virus* are antagonists of host IL-1 and toll-like receptor signalling. Proc. Natl. Acad. Sci. USA, 97, 10162-10167 (2000).
Colamonici, et al. *Vaccinia virus* B18R Gene Encodes a Type I Interferon-binding Protein That Blocks Interferon a Transmembrane Signaling, J. Biol. Chem., 270, 15974-15978. (1995).
Comeau, et al. A Poxvirus-Encoded Semaphorin Induces Cytokine Production from Monocytes and Binds to a Novel Cellular Semaphorin Receptor, VESPR. Immunity, 8, 473-482 (1998).
Denes, et al. Attenuation of vaccine strain of *Vaccinia virus* via inactivation of interferon viroceptor, J. Gene Med, 8: 814-823 (2006).
Drexler, et al. Modified *Vaccinia virus* Ankara as antigen delivery system: how can we best use its potential? Curr. Opin. Biotechnol., 15, 506-512. (2004).
Dubensky, et al. Delivery Systems for Gene-Based Vaccines. Mol. Med. 6(9): 723-732 (2000).
Falkner, et al. Transient dominant selection of recombinant *Vaccinia viruses*. J. Virol 64, 3108-3111 (1990).
Franchini, et al. Poxvirus-based vaccine candidates for HIV: two decades of experience with special emphasis on canarypox vectors. Expert Rev. Vaccines 3, S75-88 (2004).
Gardner, et al. *Vaccinia virus* semaphoring A39R is a 50-55 kDa secreted glycoprotein that affects the outcome of infection in a murine intradermal model. J. Gen. Virol., 82, 2083-2093 (2001).
Goebel, et al. GenBank Accession No. M35027 (1990).
Gomez, et al. Vaccine, 25: 196901992 (2007).
Gramaglia, et al. Ox-40 Ligand: A Potent Costimulatory Molecule for Sustaining Primary CD4 T Cell Responses. J. Immunol. 161:6510-6517 (1998).
Guerra, et al. Cellular Gene Expression Survey of *Vaccinia virus* Infection of Human HeLa Cells. J. Virol., 77, 6493-6506 (2003).
Guerra, et al, Microarray Analysis Reveals Characteristic Changes of Host Cell Gene Expression in Response to Attenuated Modified *Vaccinia virus* Ankara infection of Human HeLa Cells, J. Virol., 78, 5820-5834 (2004).
Gurunathan, et al. CD40 Ligand/Trimer DNA Enhances Both Humoral and Cellular Immune Responses and Induces Protective Immunity to Infectious and Tumor Immunity. J. Immunol, 161: 4563-4571 (1998).
Harte, et al, The Poxvirus Protein A52R Targets Toll-like Receptor Signaling Complexes to Suppress Host Defense. J. Exp. Med., 197, 343-351 (2003).
Hermonat, et al. Use of Adeno-Associated Virus as a Mammalian DNA Cloning Vector: Transduction of Neomycin Resistance Into Mammalian Tissue Culture Cells. Proc. Natl. Acad. Sci. USA, 81: 6466-6470 (1984).

(56) References Cited

OTHER PUBLICATIONS

Herz, et al. Adenovirus-Mediated Transfer of Low Density Lipoprotein Receptor Gene Acutely Accelerates Cholesterol Clearance in Normal Mice. Proc. Natl. Acad. Sci. USA, 90: 2812-2816 (1993).
Hodge, et al. Admixture of Recombinant *Vaccinia virus* Containing the Gene for the Costimulatory Molecule B7 and a Recombinant *Vaccinia virus* Containing a Tumor-associated Antigen Gene Results in Enhanced Specific T-Cell Responses and Antitumor Immunity. Cancer Res, 55: 3598-3603 (1995).
Hodge, et al. Diversified Prime and Boost Protocols Using Recombinant Vaccine Virus and Recombinant Non-Replicating Avian Pox Virus to Enhance T-Cell Immunity and Antitumor Responses. Vaccine, vol. 15, issue 6/7, pp. 759-768 (1997).
Hodge, et al. A Triad of Costimulatory Molecules Synergize to Amplify T-Cell Activation. Cancer Res. 59: 5800-5807 (1999).
Hodge, et al. Vaccine Therapy of Established Tumors in the Absence of Autoimmunity. Clin. Cancer Res. 9: 1837-1849 (2003).
Horig, et al. Phase I Clinical Trial of Recombinant Canarypox (ALVAC) Vaccine Expressing Human Carcinoembryonic Antigen and B7.1 Costimulatory Molecule. Cancer Immunol. Immunother. 49: 504-514 (2000).
Hughes, et al. Functional Discovery via a Compendium of Expression Profiles. Cell, 102, 199-126, (2000).
Hurpin, et al. The Mode of Presentation and Route of Administration Are Critical for the Induction of Immune Responses to p53 and Antitumor Immunity. Vaccine, vol. 16. No. 2/3, pp. 208-215 (1998).
Irvine, et al. Recombinant Virus Vaccination Against Self Antigens Using Anchor-Fixed Immunogens. Cancer Res., vol. 59: 2536-2540 (1999).
Jackson, et al. Role of Genes That Modulates Host Immune Responses in the Immunogenicity and Pathogenicity of *Vaccinia virus*. J. Virol. 79(10), 6554-6559 (2005).
Kanesa-thasan, et al. Safety and Immunogenicity of NYVAC-JEV and ALVAC-JEV attenuated recombinant Japanese encephalitis virus-poxvirus vaccines in *Vaccinia*-nonimmune and *Vaccinia*-immune humans. Vaccine 19, 483-491 (2000).
Kibler, et al. Double-stranded RNA is a trigger for apoptosis in *Vaccinia virus*-infected cells. J. Virol. 71,1992-2003 (1997).
Leitner, et al. Enhancement of Tumor-Specific Immune Response with Plasmid DNA Replicon Vectors. Cancer Res. 60, 51-55 (2000).
Liu, et al, Gene-Based Vaccines. Mol. Ther. 1(6), 497-500 (2000).
Ludwig, et al. Role of Viral Factor E3L in Modified *Vaccinia virus* Ankara Infection of Human HeLa Cells: Regulation of the Virus Life Cycle and Identification of Differentially Expressed Host Genes. J. Virol., 79, 2584-2596 (2005).
Mackett, et al, *Vaccinia virus*: A selectable eukaryotic cloning and expression vector. Proc. Natl. Acad. Sci. U S A 79, 7415-7419 (1982).
Marshall, et al. Phase I study in advanced cancer patients of a diversified prime-and-boost vaccination protocol using recombinant *Vaccinia virus* and recombinant nonreplicating avipox virus to elicit anti-carcinoembryonic antigen immune responses, J. Clin. Oncol. 18, 3964-3973 (2000).
Mateo, et al. An HLA-A2 Polyepitope Vaccine for Melanoma Immunotherapy. J. Immunol. 163(7), 4058-4063 (1999).
Miller, et al. Targeted Vectors for Gene Therapy. FASEB J. 9: 190-199 (1995).
Moingeon, et al. Cancer Vaccines. 19 1305-1326(2001).
Moingeon, et al. Strategies for designing vaccines eliciting Th1 responses in humans. J. Biotech. 98, 189-198 (2002).
Moore, et al. Steroid hormone synthesis by a *Vaccinia* enzyme: as new type of virus virulence factor, EMBO J., 11, 3490 (1992).
Mossman, et al. Species Specificity of Ectromella Virus and *Vaccinia virus* Interferon-γ Binding Proteins. Virology, 208, 762-769 (1995).
Myagkikh, et al. Multiple Immunizations with Attenuated Poxvirus HIV Type 2 Recombinants and Subunit Boosts Required for Protection of Rhesus Macaques, AIDS Res. Hum. Retroviruses, 12, 985-992 (1996).

Nestle, et al. Vaccination of Melanoma Patients with Peptide- or Tumor Lysate-Pulsed Dendritic Cells. Nature Med. vol. 4. No. 3, pp. 328-332 (1998).
Ng, et al. The *Vaccinia virus* A41L protein is a soluble 30 kDa glycoprotein that affects virus virulence. J. Gen. Virol, 82, 2095-2105 (2001).
Ockenhouse, et al. Phase I/IIa Safety. Immunogenicity, and Efficacy trial of NYVAC-PfT, a Pox-Vectored, Multiantigen, Multistage Candidate fro *Plasmodium falciparum* Malaria. J. Infect Dis, 177, 1664-1673 (1998).
Oertli, et al. Rapid Induction of Specific Cytotoxic T Lymphocytes Against Melanoma-Associated Antigens by a Recombinant *Vaccinia virus* Vector Expressing Multiple Immunodominant Epitopes and Costimulatory Molecules In Vivo. Human Gene Therapy, 13(4), 569-575 (Mar. 2002).
Panicali, et al. Construction of poxviruses as cloning vectors: Insertion of the thymidine kinase gene from herpes simplex virus into the DNA of infectious *Vaccinia virus*. Proc. Natl. Acad. Sci. USA, 79, 4927-4931 (1982).
Pardoll, D.M. Cancer vaccines. Nat.Med. 4: 525-531 (1998).
Parkhurst, et al. Improved Induction of Melanoma-Reactive CTL with Peptides from Melanoma Antigen gp100 Modified at HLA-A0201-Binding Residues. J. Immunol. vol. 157, No. 6, pp. 2539-2548 (1996).
Parmiani, et al. Cancer Immunotherapy with Peptide-Based Vaccines: What Have We Achieved? Where Are We Going? J. Natl. Cancer Inst. 94, 805-818 (2002).
Price, et al. *Vaccinia virus* Gene B7R Encodes an 18-kDa Protein That is Resident in the Endoplasmic Reticulum and Affects Virus Virulence., Virology, 767, 65-79 (7000).
Quentin, et al. Adenovirus as an Expression Vector in Muscle Cells in vivo. PNAS USA, 89, 2581-2584 (1992).
Reading, et al. *Vaccinia virus* Interleukin-18-Binding Protein Promotes Virulence by Reducing Gamma Interferon Production and Natural Killer and T-Cell Activity. J. Virol., 77, 9960-9968 (2003).
Reading, et al. *Vaccinia Virus* CrmE Encodes a Soluble and Cell Surface Tumor Necrosis Factor Receptor That Contributes to Virus Virulence. Virology, 292, 285-298 (2002).
Reading, et al. Steroid Hormone Synthesis by *Vaccinia virus* Suppresses the Inflammatory Responses to Infection. J. Exp. Med., 197, 1269-1278 (2003).
Ridenhour, et al. GenBank Accession No. EU512333 (2008).
Siemens, et al, Comparison of Viral Vectors: Gene Transfer Efficiency and Tissue Specificity in a Bladder Cancer Model. J. Urol, 170, 979-984 (2003).
Spagnoli, et al. Cytotoxic T-cell Induction in Metastatic Melanoma Patients Undergoing Recombinant *Vaccinia virus*-Based Immuno-Gene Therapy. Recent Results in Cancer Research, 160, 195-201 (2002).
Spriggs, et al. *Vaccinia* and *Cowpox viruses* Encode a Novel Secreted Interleukin-1-Binding Protein. Cell, 71, 145-152 (1992).
Stack, et al. *Vaccinia virus* protein A46R targets multiple Toll-like-interleukin-1 receptor adaptors and contributes to virulence. J. Exp. Med., 201, 1007-1018 (2005).
Staib, et al. Construction and Isolation of Recombinant MVA. Methods Mol. Biol., 269, 77-100 (2004).
Staib, et al. Inactivation of the viral interleukin 1βreceptor improves CD8+ T-cell memory responses elicited upon immunization with modified *Vaccinia virus* Ankara. J. Gen. Virol., 86, 1997-2006 (2005).
Su, et al, J. Virol. 74, 11367-76(2000).
Symons, et al. *Vaccinia virus* Encodes a Soluble Type I Interferon Receptor of Novel Structure and Broad Species Specificity. Cell, 81, 551-560 (1995).
Symons, et al. A study of the *Vaccinia virus* interferon-γ receptor and its contribution to virus virulence. J. Gen. Virol. 83, 1953-1964. (2002a).
Symons, et al. The *Vaccinia virus* C12L protein inhibits mouse IL-18 and promotes virus virulence in the murine intranasal model. J. Gen. Virol., 83, 2833-2844 (2002b).
Tartaglia, et al. NYVAC: A Highly Attenuated Strain of *Vaccinia virus*. Virology 188, 217-232 (1992).

(56) References Cited

OTHER PUBLICATIONS

Tartaglia, et al. Protection of Cats Against Feline Leukemia Virus by Vaccination with a *Canarypox virus* Recombinant, ALVAC-FL. J. Virol. 67, 2370-2375 (1993).

Tartaglia, et al. Safety and Immunogenicity of Recombinants Based on the Genetically-Engineered *Vaccinia* Strain, NYVAC. Dev. Biol. Stand., 82, 125-129 (1994).

Tartaglia, et al. Therapeutic Vaccines Against Melanoma and Colorectal Cancer, Vaccine, 19(17-19), 2571-2575 (2001).

Taylor, et al. The Challenge of HIV-1 Subtype Diversity, N. Engl. J. Med., 359(18),1965-1966 (2008).

Thomson, et al, Minimal Epitopes Expressed in a Recombinant Polyepitope Protein are Processed and Presented To CD8+ Cytotoxic T Cells: Implications for Vaccine Design. Proc. Natl. Acad.. Sci. USA, 92, 5845-5849 (1995).

Thomson, et al. Recombinant Polyepitope Vaccines for the Delivery of Multiple CD8 Cytotoxic T Cell Epitopes J. Immunol. 157, 822-826 (1996).

Thomson, et al. Delivery of Multiple CD8 Cytotoxic T Cell Epitopes by DNA Vaccination. J. Immunol. 160: 1717-1723 (1998).

Toes, et al. Protective Anti-Tumor Immunity Induced by Vaccination with Recombinant Adenoviruses Encoding Multiple Tumor-Associated Cytotoxic T Lymphocyte Epitopes in a String-of-Beads Fashion. Proc. Natl. Acad. Sci. USA 94, 14660-14665 (1997).

Tsao, et al. Hypopigmentation Associated with an Adenovirus-Mediated gp100/MART-1-Transduced Dendritic Cell Vaccine for Metastatic Melanoma. Arch. Dermatol. 138, 799-802 (2002).

Tscharke, et al. Dermal infection with *Vaccinia virus* reveals roles for virus proteins not seen using other inoculation routes. J. Gen. Virol. 83, 1977-1986 (2002).

Tuting, et al. Autologous Human Monocyte-Derived Dendritic Cells Genetically Modified to Express Melanoma Antigens Elicit Primary Cytotoxic T Cell Responses in vitro: Enhancement by Cotransfection of Genes Encoding the TH1 Biasing Cytokines IL-12 and IFN-alpha. J. Immunol, 160, 1139-1147 (1998).

Van Baren, et al. Tumoral and Immunologic Response After Vaccination with an ALVAC Virus Encoding MAGE Antigens Recognized by T Cells, J. Clin. Oncol. 23(35), 9008-9021 (2005).

Van Der Burg, et al. Induction of p53-Specific Immune Responses in Colorectal Cancer Patients Receiving a Recombinant ALVAC-p53 Candidate Vaccine. Clin. Cancer Res. 8, 1019-1027 (2002).

Van't Wout, et al. Cellular Gene Expression upon Human Immunodeficiency Virus Type 1 Infection of CD4+-T-Cell Lines, J. Virol., 77, 1392-1402 (2003).

Velders, et al. Defined Flanking Spacers and Enhanced Proteolysis is Essential for Eradication of Established Tumors by an Epitope String DNA Vaccine. J. Immunol. 166, 5366-5373 (2001).

Von Mehren, et al. Pilot Study of a Dual Gene Recombinant Avipox Vaccine Containing Both Carcinoembryonic Antigen (CEA) and B7.1 Transgenes in Patients with Recurrent CEA-Expressing Adenocarcinomas. Clin. Cancer Res. 6, 2219-2228 (2000).

Von Mehren, et al. The Influence of Granulocyte Macrophate Colony-Stimulating Factor and Prior Chemotherapy on the Immunological Response to a Vaccine (ALVAC-CEA B7.1) in Patients with Metastatic Melanoma. Clin. Cancer Res. 7: 1181-1191 (2001).

Walzer, et al. Poxvirus semaphoring A39R inhibits phagocytosis by dendritic cells and neutrophils. Eur. J. Immunol., 35, 391-398 (2005a).

Walzer, et al. Plexin C1 Engagement on Mouse Dendritic Cells by Viral Semaphorin A39R Induces Actin Cytoskeleton Rearrangement and Inhibits Integrin-Mediated Adhesion and Chemokine-Induced Migration. J. Immunol., 174, 51-59 (2005b).

Wilcock, et al. The *Vaccinia virus* A40R gene product is a nonstructural, type II membrane glycoprotein that is expressed at the cell surface. J. Gen. Virol., 80, 2137-2148 (1999).

Xiang, et al. An Autologous Oral DNA Vaccine Protects Against Murine Melanoma. Proc. Natl. Acad. Sci. USA, vol. 97, No. 10, pp. 5492-5497 (2000).

Zhu, et al. Cellular gene expression altered by human cytomegalovirus: Global monitoring, with oligonucleotide arrays Proc. Natl. Acad. Sci. USA, 95, 14470-14475 (1998).

Najera, et al. Cellular and Biochemical Differences between Two Attenuated Poxvirus Vaccine Candidates (MVA and NYVAC) and Role of the C7L Gene. J. Virol. 80(12): 6033-6047 (2006).

* cited by examiner

Construction of plasmid transfer vector pGem-RG-B8R wm

FIG. 4
PCR analysis of NYVAC-C-ΔB8R, NYVAC-C-ΔB19R, NYVAC-C-ΔB84/B19R

Construction of plasmid transfer vector pGem-RG-B19R wm

Wild type Copenhagen genome 12 open reading frames plus flanking regions were amplified by PCR to yield the +12 fragment.

This fragment was inserted into NYVAC-C by *in vivo recombination* to create NYVAC-C+12.

US 9,670,506 B2

MODIFIED IMMUNIZATION VECTORS

PRIOR APPLICATIONS

This application is filed under 35 U.S.C. §371, and claims priority to International Application No. PCT/US2010/032966 filed Apr. 30, 2010, which claims priority to U.S. Ser. No. 61/174,024 filed Apr. 30, 2009.

FIELD OF THE INVENTION

The disclosure relates to modified vectors for use in immunological compositions.

BACKGROUND OF THE INVENTION

There is need in the art for effective immunological compositions and methods for immunizing animals and humans using recombinant vectors. It is known in the art that certain vectors (e.g., replication-incompetent vaccinia vectors) are insufficient as immunomodulators. As described herein, modification of such vectors provides a solution to these problems.

BRIEF DESCRIPTION OF THE DRAWINGS

FIG. 4. PCR analysis of NYVAC-C-ΔB8R, NYVAC-C-ΔB19R and NYVAC-C-ΔB8RB19R.

SUMMARY OF THE DISCLOSURE

Figure 1:
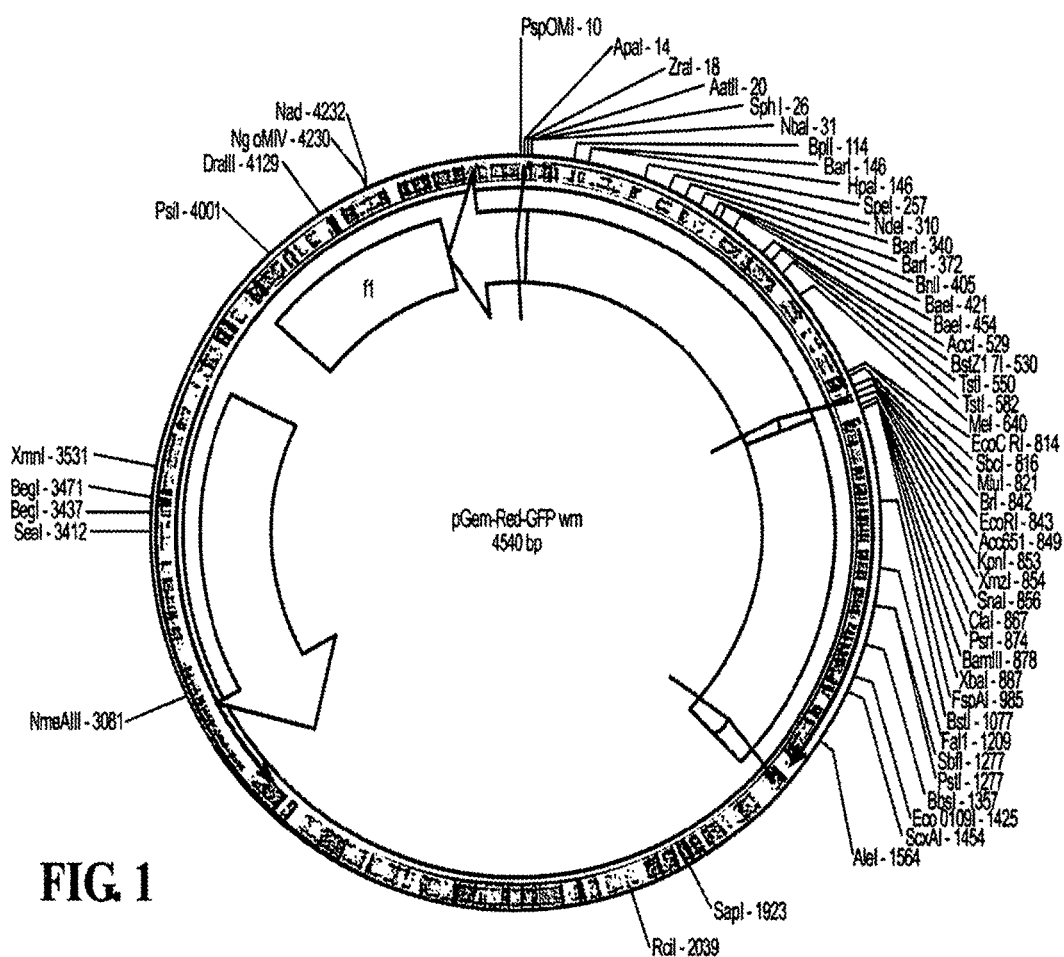
FIG. 1. Plasmid maps of transfer vectors.

Disclosed herein are compositions and reagents for immunizing human beings against infectious or other agents such as tumor cells by inducing or enhancing thereto. In certain embodiments, the compositions comprise recombinant viral vectors comprising modified nucleotide sequences. In certain embodiments, the vectors were modified by deletion of and/or insertion of nucleic acids encoding any one or more of the polypeptides shown in SEQ ID NOS. 1, 3, 5, 7, 9, 11, 13, 15, 17, 19. 21. 23, 25, or 27. Exemplary of such polynucleotides are those shown in SEQ ID NOS. 2, 4, 6, 8, 10, 12, 14, 16, 18, 20, 22, 24, 26, and 28. In some embodiments, such vectors further comprise polynucleotides encoding immunogens. Methods for constructing and using such vectors are described herein. Compositions comprising such vectors and methods for using such compositions are also provided.

DETAILED DESCRIPTION

The present disclosure provides compositions and methodologies useful for expressing nucleic acids and the polypeptides, peptides, or nucleic acids encoded thereby using recombinant vectors. In one embodiment, the compositions comprise recombinant vectors for introducing or altering the expression of a polypeptide, peptide, or nucleic acid in a host. In some embodiments, the compositions may include one or more recombinant viruses comprising polynucleotides encoding polypeptides, peptides, or polynucleotides that were not previously expressed by the virus, or are normally expressed in different amounts or at different times in the life cycle of the virus. In certain embodiments, polynucleotides are incorporated into the genome of a virus to produce a recombinant virus with altered characteristics as compared to the non-modified virus. In some embodiments, the incorporated polynucleotides encode polypeptides, peptides, or polynucleotides that alter the growth characteristics, infectivity, host range, replicative capacity, or immunogenicity of the recombinant virus as compared to the non-modified virus. Such polynucleotides may be used alone or in combination with other polynucleotides such as those described below (e.g., encoding one or more immunogens).

Expression vectors may also be modified by deleting polynucleotides (e.g., a gene) normally found within the vector therefrom. For instance, the poxvirus NYVAC (described in more detail below) was derived from the Copenhagen vaccinia strain using transient dominant selection (Falkner & Moss, 1990) which allows for deletion of one or more target genes without incorporation of a polynucleotide encoding a selectable marker into the viral genome. Polynucleotides may be completely or partially deleted, or inactivated with or without partial deletion. Partial deletion may be accomplished by removing a portion of a polynucleotide encoding a polypeptide from the "genome" of the vector ("vector genome"). As referred to herein, the vector genome may refer to the polynucleotide encoding the various factors required for the viability of a replication-competent or replication-incompetent viral vector, the polynucleotide making up a non-viral (e.g., bacterial, eukaryotic) or viral plasmid vector, or the like.

For instance, NYVAC is derived from the VACV strain Copenhagen (COP) from which 18 genes encoding proteins involved in host range and virulence were deleted (Tartaglia et al., 1992). These vectors were shown to exhibit altered host range and to be useful for expressing immunogens within a wide range of species (Tartaglia et al., 1994). Such vectors have been used as recombinant vaccines against numerous pathogens and tumours in animal models and in target species, including humans (Myagkikh et al., 1996; Benson et al., 1998; Siemens et al., 2003; Franchini et al., 2004). Clinical trials using NYVAC-based vectors showed an acceptable safety profile, with induction of high levels of immunity against heterologous antigens (Kanesa-thasan et al., 2000; Gómez, C. E et al. 2007; Harari, A et al, 2008). Such vectors may be further modified by insertion or deletion of additional polynucleotides using the techniques described herein. Suitable polynucleotides may include, for example, those involved in host range, apoptosis, signaling, cytokine and/or chemokine expression or activity, cytokine and/or chemokine pathways, and/or the like, resulting in novel biological characteristics of the vectors.

In some embodiments, polynucleotides encoding immunomodulatory polypeptides are selectively deleted from a vector genome. Polynucleotides encoding immunogens may also be incorporated into the vector genome. This may lead to modulation of virus-host cell interactions and "improvement" in the immunological profiles of the modified vectors as candidate vaccines. By "improvement" is meant that an immune response against a target antigen is induced or enhanced. In certain embodiments, the modified vectors may exhibit improved safety profiles as compared to non-modified (e.g., parental) vectors.

Polynucleotides suitable to modification (e.g., deletion from, alteration of sequence, or incorporation into a vector genome) may include, for example, any polynucleotide that provides the desired effect (e.g., an improved immune response). For instance, within the NYVAC vector, candidate polynucleotides may include polynucleotides that may be characterized as immunomodulators, and those affecting viral host range, one or more signalling pathways, apoptosis, secreted proteins (e.g., those binding host cytokines and/or chemokines). Exemplary polynucleotides and polypeptides that are candidates for modification include those encoding, for example, B8R (SEQ ID NOS. 1, 2) and/or B19R (SEQ ID NOS. 3, 4). In certain embodiments, suitable and exemplary polynucleotides may encode immunomodulatory polypeptides that interact with, for example, one or more interferons, cytokines and/or chemokines (e.g., B8R (SEQ ID NOS. 1, 2), and/or B19R (SEQ ID NOS. 3, 4)). The nomenclature of these sequences is related to the Copenhagen strain of vaccinia virus (GenBank Accession No. M35027; Goebel, et al. The complete DNA sequence of vaccinia virus. Virology 179 (1), 247-266 (1990); Goebel, et al. Appendix to 'The complete DNA sequence of Vaccinia virus'. Virology 179, 517-563 (1990)). Any of such polynucleotides may be modified (e.g., incorporated into a recombinant vector or as part of a composition containing multiple recombinant vectors) in combination with any other of such polynucleotides. Other polynucleotides may also be suitable for modification in vaccinia or in other viruses (e.g., MVA, avipox, and the like).

The B8R gene (open reading frame ("ORF") shown in SEQ ID NO. 1) encodes the B8R protein (SEQ ID NO. 2) with amino acid similarity to the extracellular domain of the IFN-γ receptor (Alcami & Smith, 1995; Mossman et al., 1995). The protein B8 binds and inhibits IFN-γ from a wide variety of species but not the mouse. Deletion of B8R from WR did not alter virus replication or virulence in mouse models (Symons, et al. 2002a).

The B19R gene of VACV (ORF shown in SEQ ID NO. 3 encoding the B19R polypeptide, SEQ ID NO. 4) is equivalent to the B18R gene of VACV WR and encodes a type I IFN (α,β)-receptor homolog. Protein B19 binds and inhibits type I IFN from a wide variety of species except murine IFN which binds but does not inhibit it. Deletion of B19R from VACV WR has been shown to cause attenuation in a murine intranasal model.

Within vaccinia, the C1L (SEQ ID NO. 5), C2L (SEQ ID NO. 7), C3L (SEQ ID NO. 9), C4L (SEQ ID NO. 11), C5L (SEQ ID NO. 13), C6L (SEQ ID NO. 15), C7L (SEQ ID NO. 17), N1L (SEQ ID NO. 19), N2L (SEQ ID NO. 21), M1L (SEQ ID NO. 23), M2L (SEQ ID NO. 25) and K1L (SEQ ID NO. 27) polypeptides have been shown to be involved in defining the "host range" or replication competence of the virus. Polynucleotides encoding such host range polypeptides are illustrated in SEQ ID NOS. 6, 8, 10, 12, 14, 16, 18, 20, 22, 24, 26, and 28. In the NYVAC virus, these genes have been deleted. In certain embodiments, one or more polynucleotides representing one or more of these host range genes may be introduced into the genome of a viral vector to affect the replication competence of the vector. In NYVAC, for example, one or more polynucleotides representing one or more of such host range genes may be re-incorporated into the NYVAC genome to modify its replication competence. In certain embodiments, as shown in the Examples, polynucleotides encoding C7L (e.g., SEQ ID NOS. 17, 18) and K1L (e.g., SEQ ID NOS. 27, 28) were shown to effect replication competence of NYVAC. In certain embodiments, the recombinant vector (e.g., NYVAC) expresses at least one, two, three, four, five, six, seven, eight, nine, ten, eleven or twelve of C1L (e.g., SEQ ID NOS. 5, 6), C2L (e.g., SEQ ID NOS. 7, 8), C3L (e.g., SEQ ID NOS. 9, 10), C4L (SEQ ID NOS. 11, 12), C5L (e.g., SEQ ID NOS. 13, 14), C6L (e.g., SEQ ID NOS. 15, 16), C7L (e.g., SEQ ID NOS. 17, 18), N1L (SEQ ID NOS. 19, 20), N2L (e.g., SEQ ID NOS. 21, 22), M1L (e.g., SEQ ID NOS. 23, 24), M2L (e.g., SEQ ID NOS. 25, 26), and K1L (e.g., SEQ ID NOS. 27, 28). Various combinations of such polynucleotides and/or polypeptides, as would be apparent to one of skill in the art, may be utilized in vectors. These polynucleotides and/or polypeptides may also be incorporated into vectors engineered to contain or express other polynucleotides and/or polypeptides such as, for example, B8R (SEQ ID NOS. 1, 2) and/or B19R (SEQ ID NOS. 3, 4). Suitable recombinant vectors for introduction or re-introduction of such host range genes include those from which such sequences have been previously deleted or those that otherwise do not contain such genes within the vector genome. It is also possible to modify such host range genes such that their function is altered by, for example, altering the timing or character (e.g., expression level) of expression within a host cell.

Polynucleotides encoding other polypeptides, peptides, or nucleic acids affecting the activity of a recombinant vector (e.g., recombinant virus) may also be incorporated into the vector. In certain embodiments, polynucleotides representing genes from other organisms (exogenous genes) may be incorporated into the vector. The polynucleotides may be inserted into a polynucleotide by insertion, either de novo or by replacement of an existing polynucleotide sequence within the vector genome. For instance, a polynucleotide may replace a gene of a virus. For example, the ranavirus eIF2α-like gene ("eIF2αH") from *Ambystoma tigrinum* virus isolate YEL protein gene (GenBank Accession No. EU512333; version EU512333.1; GI:170180537; "ATV eIF2αH"; SEQ ID NO. 29 encoded by SEQ ID NO. 30; see, e.g., U.S. Pat. No. 7,431,929) may be utilized. ATV eIF2αH encodes a potent, non-dsRNA-binding inhibitor of RNA-dependent protein kinase (PKR). In one embodiment, a polynucleotide encoding ATV eIF2αH (e.g., SEQ ID NO. 30) may be incorporated into a recombinant vector described herein. Without being limited to any particular theory of operation, it is believed that ATV eIF2αH induces signal transduction through NF-κB and IRF-3, while sparing viral protein synthesis from the inhibitory effects of PKR activation. In certain embodiments, a recombinant virus may be produced that exhibits little, decreased, or no replication competence but also induces an immune response in a host. Such a virus may provide an optimal recombinant vector that represents a "compromise" between replication competent that may cause complications in hosts, and replication deficient recombinant vectors that may fail to induce an immune response, or may induce a sub-optimal immune response.

In certain embodiments, in addition to the one or more polynucleotides encoding one or more of B8R (SEQ ID NOS. 1, 2) and/or B19R (SEQ ID NOS. 3, 4)), the recombinant vector may also comprise a polynucleotide encoding ATV eIF2αH (e.g., SEQ ID NOS. 29, 30) such as SEQ ID NO. 54. In other embodiments, a recombinant vector including any one or more of C1L (e.g., SEQ ID NOS. 5, 6), C2L (e.g., SEQ ID NOS. 7, 8), C3L (e.g., SEQ ID NOS. 9, 10), C4L (SEQ ID NOS. 11, 12), C5L (e.g., SEQ ID NOS. 13, 14), C6L (e.g., SEQ ID NOS. 15, 16), C7L (e.g., SEQ ID NOS. 17, 18), N1L (SEQ ID NOS. 19, 20), N2L (e.g., SEQ ID NOS. 21, 22), M1L (e.g., SEQ ID NOS. 23, 24), M2L (e.g., SEQ ID NOS. 25, 26), and/or K1L (e.g., SEQ ID NOS. 27, 28) (or a deletion of any one or more of these sequences) may also comprise a polynucleotide encoding ATV eIF2αH (e.g., SEQ ID NOS. 29, 30). In yet other embodiments, a recombinant vector may also comprise one or more polynucleotides encoding one or more of B8R (SEQ ID NOS. 1, 2) and/or B19R (SEQ ID NOS. 3, 4)) and/or a polynucleotide encoding ATV eIF2αH (e.g., SEQ ID NOS. 29, 30), and/or any one or more of C1L (e.g., SEQ ID NOS. 5, 6), C2L (e.g., SEQ ID NOS. 7, 8), C3L (e.g., SEQ ID NOS. 9, 10), C4L (SEQ ID NOS. 11, 12), C5L (e.g., SEQ ID NOS. 13, 14), C6L (e.g., SEQ ID NOS. 15, 16), C7L (e.g., SEQ ID NOS. 17, 18), N1L (SEQ ID NOS. 19, 20), N2L (e.g., SEQ ID NOS. 21, 22), M1L (e.g., SEQ ID NOS. 23, 24), M2L (e.g., SEQ ID NOS. 25, 26), and/or K1L (e.g., SEQ ID NOS. 27, 28). For instance, the Examples demonstrate a recombinant vaccinia virus in which the E3L gene was deleted and replaced by a polynucleotide encoding ATV eIF2αH (SEQ ID NO. 30 encoding SEQ ID NO. 29; see, e.g., U.S. Pat. No. 7,431,929). It was observed that this modified virus induces host cell production of IFN, exhibits increased sensitivity to IFN, and induces a potent Th1-dominated immune response at low doses. Other embodiments, as could be derived from this disclosure, may also be suitable for use.

In some embodiments, the compositions may include one or more recombinant vectors encoding one or more immunogens that may be used to induce or enhance an immune response that is beneficial to the host. As such, the compositions described herein may also be used to treat and/or prevent conditions relating to an infectious or other agent(s) by inducing or enhancing an immune response against such an agent. In certain embodiments, the compositions may comprise one or more recombinant vectors encoding one or more immunogens (e.g., comprising a polynucleotide encoding the antigen). An immunogen may be isolated from its source (e.g., an infectious agent) of which it forms a part (e.g., a polypeptide normally found within or expressed by that infectious agent). In certain embodiments, the immunogen may be encoded by a nucleotide sequence in expressible form (e.g., within an expression vector).

An immunogen may be a moiety (e.g., polypeptide, peptide or nucleic acid) that induces or enhances the immune response of a host to whom or to which the immunogen is administered. An immune response may be induced or enhanced by either increasing or decreasing the frequency, amount, or half-life of a particular immune modulator (e.g, the expression of a cytokine, chemokine, co-stimulatory molecule). This may be directly observed within a host cell containing a polynucleotide of interest (e.g., following infection by a recombinant virus) or within a nearby cell or tissue (e.g., indirectly). The immune response is typically directed against a target antigen. For example, an immune response may result from expression of an immunogen in a host following administration of a nucleic acid vector encoding the immunogen to the host. The immune response may result in one or more of an effect (e.g., maturation, proliferation, direct- or cross-presentation of antigen, gene expression profile) on cells of either the innate or adaptive immune system. For example, the immune response may involve, effect, or be detected in innate immune cells such as, for example, dendritic cells, monocytes, macrophages, natural killer cells, and/or granulocytes (e.g., neutrophils, basophils or eosinophils). The immune response may also involve, effect, or be detected in adaptive immune cells including, for example, lymphocytes (e.g., T cells and/or B cells). The immune response may be observed by detecting such involvement or effects including, for example, the presence, absence, or altered (e.g., increased or decreased) expression or activity of one or more immunomodulators such as a hormone, cytokine, interleukin (e.g., any of IL-1 through IL-35), interferon (e.g., any of IFN-I (IFN-α, IFN-β, IFN-ε, IFN-κ, IFN-τ, IFN-ζ, IFN-ω), IFN-II (e.g., IFN-γ), IFN-III (IFN-λ1, IFN-λ2, IFN-λ3)), chemokine (e.g., any CC cytokine (e.g., any of CCL1 through CCL28), any CXC chemokine (e.g., any of CXCL1 through CXCL24), Mip1a), any C chemokine (e.g., XCL1, XCL2), any CX3C chemokine (e.g., CX3CL1)), tumor necrosis factor (e.g., TNF-α, TNF-β)), negative regulators (e.g., PD-1, IL-T) and/or any of the cellular components (e.g., kinases, lipases, nucleases, transcription-related factors (e.g., IRF-1, IRF-7, STAT-5, NFKB, STAT3, STAT1, IRF-10), and/or cell surface markers suppressed or induced by such immunomodulators) involved in the expression of such immunomodulators. The presence, absence or altered expression may be detected within cells of interest or near those cells (e.g., within a cell culture supernatant, nearby cell or tissue in vitro or in vivo, and/or in blood or plasma).

Administration of the immunogen may induce (e.g., stimulate a de novo or previously undetected response), or enhance or suppress an existing response against the immunogen by, for example, causing an increased antibody response (e.g., amount of antibody, increased affinity/avidity) or an increased cellular response (e.g., increased number of activated T cells, increased affinity/avidity of T cell receptors). In certain embodiments, the immune response may be protective, meaning that the immune response may be capable of preventing initiation or continued infection of or growth within a host and/or by eliminating an agent (e.g., a causative agent, such as HIV) from the host.

The compositions described herein may include one or more immunogen(s) from a single source or multiple sources. For instance, immunogens may also be derived from or direct an immune response against one or more viruses (e.g., viral target antigen(s)) including, for example, a dsDNA virus (e.g. adenovirus, herpesvirus, epstein-barr virus, herpes simplex type 1, herpes simplex type 2, human herpes virus simplex type 8, human cytomegalovirus, varicella-zoster virus, poxvirus); ssDNA virus (e.g., parvovirus, papillomavirus (e.g., E1, E2, E3, E4, E5, E6, E7, E8, BPV1, BPV2, BPV3, BPV4, BPV5 and BPV6 (In Papillomavirus and Human Cancer, edited by H. Pfister (CRC Press, Inc. 1990); Lancaster et al., Cancer Metast. Rev. pp. 6653-6664 (1987); Pfister, et al. Adv. Cancer Res 48, 113-147 (1987)); dsRNA viruses (e.g., reovirus); (+)ssRNA viruses (e.g., picornavirus, coxsackie virus, hepatitis A virus, poliovirus, togavirus, rubella virus, flavivirus, hepatitis C virus, yellow fever virus, dengue virus, west Nile virus); (−)ssRNA viruses (e.g., orthomyxovirus, influenza virus, rhabdovirus, paramyxovirus, measles virus, mumps virus, parainfluenza virus, respiratory syncytial virus, rhabdovirus, rabies virus); ssRNA-RT viruses (e.g. retrovirus, human immunodeficiency virus (HIV)); and, dsDNA-RT viruses (e.g. hepadnavirus, hepatitis B). Immunogens may also be derived from other viruses not listed above but available to one of skill in the art.

With respect to HIV, immunogens may be selected from any HIV isolate. As is well-known in the art, HIV isolates are now classified into discrete genetic subtypes. HIV-1 is known to comprise at least ten subtypes (A1, A2, A3, A4, B, C, D, E, F1, F2, G, H, J and K) (Taylor et al, NEJM, 359(18):1965-1966 (2008)). HIV-2 is known to include at least five subtypes (A, B, C, D, and E). Subtype B has been associated with the HIV epidemic in homosexual men and intravenous drug users worldwide. Most HIV-1 immunogens, laboratory adapted isolates, reagents and mapped epitopes belong to subtype B. In sub-Saharan Africa, India and China, areas where the incidence of new HIV infections is high, HIV-1 subtype B accounts for only a small minority of infections, and subtype HIV-1 C appears to be the most common infecting subtype. Thus, in certain embodiments, it may be preferable to select immunogens from HIV-1 subtypes B and/or C. It may be desirable to include immunogens from multiple HIV subtypes (e.g., HIV-1 subtypes B and C, HIV-2 subtypes A and B, or a combination of HIV-1 and HIV-2 subtypes) in a single immunological composition. Suitable HIV immunogens include ENV, GAG, POL, NEF, as well as variants, derivatives, and fusion proteins thereof, as described by, for example, Gomez et al. Vaccine, Vol. 25, pp. 1969-1992 (2007)). Exemplary, suitable peptide immunogens derived from HIV include but are not limited to VGNLWVTVYYGVPVW (SEQ ID NO. 31), WVTVYYGVPVWKGAT (SEQ ID NO. 32), GATTTLFCASDAKAY (SEQ ID NO. 33), TTLFCASDAKAYDTE (SEQ ID NO. 34), THACVPADPNPQEMV (SEQ ID NO. 35), ENVTENFNMWKNEMV (SEQ ID NO. 36), ENFNMWKNEMVNQMQ (SEQ ID NO. 37), EMVNQMQEDVISLWD (SEQ ID NO. 38), CVKLTPLCVTLECRN (SEQ ID NO. 39), NCSFNATTVVRDRKQ (SEQ ID NO. 40), NATTVVRDRKQTVYA (SEQ ID NO. 41), VYALFYRLDIVPLTK (SEQ ID NO. 42), FYRLDIVPLTKKNYS (SEQ ID NO. 43), INCNTSAITQACPKV (SEQ ID NO. 44), PKVTFDPIPIHYCTP (SEQ ID NO. 45), FDPIPIHYCTPAGYA (SEQ ID NO. 46), TGDIIGDIRQAHCNI (SEQ ID NO. 47), SSSIITIPCRIKQII (SEQ ID NO. 48), ITIPCRIKQIINMWQ (SEQ ID NO. 49), CRIKQIINMWQEVGR (SEQ ID NO. 50), VGRAMYAPPIKGNIT (SEQ ID NO. 51), MYAPPIKGNITCKSN (SEQ ID. NO. 52), PIKGNITCKSNITGL (SEQ ID NO. 53), ETFRPGGGDMRNNWR (SEQ ID NO. 54), ELYKYKVVEIKPLGV (SEQ ID NO. 55), YKVVEIKPLGVAPTT (SEQ ID NO. 56), EIKPLGVAPTTTKRR (SEQ ID NO. 57), LGVAPTTTKRRVVER (SEQ ID NO. 58), and/or YSENSSEYY (SEQ ID NO. 59). Any of these may be encoded by a polynucleotide within a recombinant vector, and/or used in combination with a recombinant vector as part of an immunization strategy.

Immunogens may also be derived from or direct an immune response against one or more bacterial species (spp.) (e.g., bacterial target antigen(s)) including, for example, *Bacillus* spp. (e.g., *Bacillus anthracis*), *Bordetella* spp. (e.g., *Bordetella pertussis*), *Borrelia* spp. (e.g., *Borrelia burgdorferi*), *Brucella* spp. (e.g., *Brucella abortus, Brucella canis, Brucella melitensis, Brucella suis*), *Campylobacter* spp. (e.g., *Campylobacter jejuni*), *Chlamydia* spp. (e.g., *Chlamydia pneumoniae, Chlamydia psittaci, Chlamydia trachomatis*), *Clostridium* spp. (e.g., *Clostridium botulinum, Clostridium difficile, Clostridium perfringens, Clostridium tetani*), *Corynebacterium* spp. (e.g., *Corynebacterium diptheriae*), *Enterococcus* spp. (e.g., *Enterococcus faecalis, enterococcus faecum*), *Escherichia* spp. (e.g., *Escherichia coli*), *Francisella* spp. (e.g., *Francisella tularensis*), *Haemophilus* spp. (e.g., *Haemophilus influenza*), *Helicobacter* spp. (e.g.; *Helicobacter pylori*), *Legionella* spp. (e.g., *Legionella pneumophila*), *Leptospira* spp. (e.g., *Leptospira interrogans*), *Listeria* spp. (e.g., *Listeria monocytogenes*), *Mycobacterium* spp. (e.g., *Mycobacterium leprae, Mycobacterium tuberculosis*), *Mycoplasma* spp. (e.g., *Mycoplasma pneumoniae*), *Neisseria* spp. (e.g., *Neisseria gonorrhea, Neisseria meningitidis*), *Pseudomonas* spp. (e.g., *Pseudomonas aeruginosa*), *Rickettsia* spp. (e.g., *Rickettsia rickettsii*), *Salmonella* spp. (e.g., *Salmonella typhi, Salmonella typhinurium*), *Shigella* spp. (e.g., *Shigella sonnei*), *Staphylococcus* spp. (e.g., *Staphylococcus aureus, Staphylococcus epidermidis, Staphylococcus saprophyticus*, coagulase negative *staphylococcus* (e.g., U.S. Pat. No. 7,473,762)), *Streptococcus* spp. (e.g., *Streptococcus agalactiae, Streptococcus pneumoniae, Streptococcus pyrogenes*), *Treponema* spp. (e.g., *Treponema pallidum*), *Vibrio* spp. (e.g., *Vibrio cholerae*), and *Yersinia* spp. (*Yersinia pestis*). Immunogens may also be derived from or direct the immune response, against other bacterial species not listed above but available to one of skill in the art.

Immunogens may also be derived from or direct an immune response against one or more parasitic organisms (spp.) (e.g., parasite target antigen(s)) including, for example, *Ancylostoma* spp. (e.g., *A. duodenale*), *Anisakis* spp., *Ascaris lumbricoides, Balantidium coli, Cestoda* spp., *Cimicidae* spp., *Clonorchis sinensis, Dicrocoelium dendriticum, Dicrocoelium hospes, Diphyllobothrium latum, Dracunculus* spp., *Echinococcus* spp. (e.g., *E. granulosus, E. multilocularis*), *Entamoeba histolytica, Enterobius vermicu-* laris, Fasciola spp. (e.g., *F. hepatica, F. magna, F. gigantica, F. jacksoni*), *Fasciolopsis buski, Giardia* spp. (*Giardia lamblia*), *Gnathostoma* spp., *Hymenolepis* spp. (e.g., *H. nana, H. diminuta*), *Leishmania* spp., *Loa loa, Metorchis* spp. (*M. conjunctus, M. albidus*), *Necator americanus, Oestroidea* spp. (e.g., botfly), *Onchocercidae* spp., *Opisthorchis* spp. (e.g., *O. viverrini, O. felineus, O. guayaquilensis,* and *O. noverca*), *Plasmodium* spp. (e.g., *P. falciparum*), *Protofasciola robusta, Parafasciolopsis fasciomorphae, Paragonimus westermani, Schistosoma* spp. (e.g., *S. mansoni, S. japonicum, S. mekongi, S. haematobium*), *Spirometra erinaceieuropaei, Strongyloides stercoralis, Taenia* spp. (e.g., *T. saginata, T. solium*), *Toxocara* spp. (e.g., *T. canis, T. cati*), *Toxoplasma* spp. (e.g., *T. gondii*), *Trichobilharzia regenti, Trichinella spiralis, Trichuris trichiura, Trombiculidae* spp., *Trypanosoma* spp., *Tunga penetrans,* and/or *Wuchereria bancrofti.* Immunogens may also be derived from or direct the immune response against other parasitic organisms not listed above but available to one of skill in the art.

Immunogens may be derived from or direct the immune response against tumor target antigens (e.g., tumor target antigens). The term tumor target antigen (TA) may include both tumor-associated antigens (TAAs) and tumor-specific antigens (TSAs), where a cancerous cell is the source of the antigen. A TA may be an antigen that is expressed on the surface of a tumor cell in higher amounts than is observed on normal cells or an antigen that is expressed on normal cells during fetal development. A TSA is typically an antigen that is unique to tumor cells and is not expressed on normal cells. TAs are typically classified into five categories according to their expression pattern, function, or genetic origin: cancer-testis (CT) antigens (i.e., MAGE, NY-ESO-1); melanocyte differentiation antigens (i.e., Melan A/MART-1, tyrosinase, gp100); mutational antigens (i.e., MUM-1, p53, CDK-4); overexpressed 'self' antigens (i.e., HER-2/neu, p53); and, viral antigens (i.e., HPV, EBV). Suitable TAs include, for example, gp100 (Cox et al., *Science*, 264:716-719 (1994)), MART-1/Melan A (Kawakami et al., *J. Exp. Med.*, 180:347-352 (1994)), gp75 (TRP-1) (Wang et al., *J. Exp. Med.*, 186:1131-1140 (1996)), tyrosinase (Wolfel et al., *Eur. J. Immunol.*, 24:759-764 (1994)), NY-ESO-1 (WO 98/14464; WO 99/18206), melanoma proteoglycan (Hellstrom et al., *J. Immunol.*, 130:1467-1472 (1983)), MAGE family antigens (i.e., MAGE-1, 2, 3, 4, 6, and 12; Van der Bruggen et al., *Science*, 254:1643-1647 (1991); U.S. Pat. No. 6,235,525), BAGE family antigens (Boel et al., *Immunity*, 2:167-175 (1995)), GAGE family antigens (i.e., GAGE-1, 2; Van den Eynde et al., *J. Exp. Med.*, 182:689-698 (1995); U.S. Pat. No. 6,013,765), RAGE family antigens (i.e., RAGE-1; Gaugler et al., *Immunogenetics*, 44:323-330 (1996); U.S. Pat. No. 5,939,526), N-acetylglucosaminyl-transferase-V (Guilloux et al., *J. Exp. Med.*, 183:1173-1183 (1996)), p15 (Robbins et al., *J. Immunol.* 154:5944-5950 (1995)), β-catenin (Robbins et al., *J. Exp. Med.*, 183:1185-1192 (1996)), MUM-1 (Coulie et al., *Proc. Natl. Acad. Sci. USA*, 92:7976-7980 (1995)), cyclin dependent kinase-4 (CDK4) (Wolfel et al., *Science*, 269:1281-1284 (1995)), p21-ras (Fossum et al., *Int. J. Cancer*, 56:40-45 (1994)), BCR-abl (Bocchia et al., *Blood*, 85:2680-2684 (1995)), p53 (Theobald et al., *Proc. Natl. Acad. Sci. USA*, 92:11993-11997 (1995)), p185 HER2/neu (erb-B1; Fisk et al., *J. Exp. Med.*, 181:2109-2117 (1995)), epidermal growth factor receptor (EGFR) (Harris et al., Breast Cancer Res. Treat, 29:1-2 (1994)), carcinoembryonic antigens (CEA) (Kwong et al., *J. Natl. Cancer Inst.*, 85:982-990 (1995) U.S. Pat. Nos. 5,756,103; 5,274,087; 5,571,710; 6,071,716; 5,698,530; 6,045,802; EP 263933; EP 346710; and, EP 784483); carcinoma-associated mutated mucins (i.e., MUC-1 gene products; Jerome et al., *J. Immunol.*, 151:1654-1662 (1993)); EBNA gene products of EBV (i.e., EBNA-1; Rickinson et al., *Cancer Surveys*, 13:53-80 (1992)); E7, E6 proteins of human papillomavirus (Ressing et al., *J. Immunol*, 154: 5934-5943 (1995)); prostate specific antigen (PSA; Xue et al., *The Prostate*, 30:73-78 (1997)); prostate specific membrane antigen (PSMA; Israeli, et al., *Cancer Res.*, 54:1807-1811 (1994)); idiotypic epitopes or antigens, for example, immunoglobulin idiotypes or T cell receptor idiotypes (Chen et al., *J. Immunol.*, 153:4775-4787 (1994)); KSA (U.S. Pat. No. 5,348,887), kinesin 2 (Dietz, et al. Biochem Biophys Res Commun 2000 Sep. 7; 275(3):731-8), HIP-55, TGFβ-1 anti-apoptotic factor (Toomey, et al. Br J Biomed Sci 2001; 58(3):177-83), tumor protein D52 (Bryne J. A., et al., *Genomics*, 35:523-532 (1996)), HIFT, NY-BR-1 (WO 01/47959), NY-BR-62, NY-BR-75, NY-BR-85, NY-BR-87 and NY-BR-96 (Scanlan, M. Serologic and Bioinformatic Approaches to the Identification of Human Tumor Antigens, in *Cancer Vaccines* 2000, Cancer Research Institute, New York, N.Y.), and/or pancreatic cancer antigens (e.g., SEQ ID NOS: 1-288 of U.S. Pat. No. 7,473,531). Immunogens may also be derived from or direct the immune response against include TAs not listed above but available to one of skill in the art.

In some embodiments, derivatives of polypeptides, peptides, or polynucleotides incorporated into or expressed by the vectors described herein including, for example, fragments and/or variants thereof may be utilized. Derivatives may result from, for example, substitution, deletion, or addition of amino acids or nucleotides from or to the reference sequence (e.g., the parental sequence). A derivative of a polypeptide or protein, for example, typically refers to an amino acid sequence that is altered with respect to the referenced polypeptide or peptide. A derivative of a polypeptide typically retains at least one activity of the polypeptide. A derivative will typically share at least approximately 60%, 70%, 80%, 90%, 95%, or 99% identity to the reference sequence. With respect to polypeptides and peptides, the derivative may have "conservative" changes, wherein a substituted amino acid has similar structural or chemical properties. A derivative may also have "nonconservative" changes. Exemplary, suitable conservative amino acid substitutions may include, for example, those shown in Table 1:

TABLE 1

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

Other amino acid substitutions may be considered non-conservative. Derivatives may also include amino acid or nucleotide deletions and/or additions/insertions, or some combination of these. Guidance in determining which amino acid residues or nucleotides may be substituted, inserted, or deleted without abolishing the desired activity of the derivative may be identified using any of the methods available to one of skill in the art.

Derivatives may also refer to a chemically modified polynucleotide or polypeptide. Chemical modifications of a polynucleotide may include, for example, replacement of hydrogen by an alkyl, acyl, hydroxyl, or amino group. A derivative polynucleotide may encode a polypeptide which retains at least one biological or immunological function of the natural molecule. A derivative polypeptide may be one modified by glycosylation, pegylation, biotinylation, or any similar process that retains at least one biological or immunological function of the polypeptide from which it was derived.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (end therefore function) of the polypeptide. Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 10, at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

As mentioned above, this disclosure relates to compositions comprising recombinant vectors, the vectors per se, and methods of using the same. A "vector" is any moiety (e.g., a virus or plasmid) used to carry, introduce, or transfer a polynucleotide or interest to another moiety (e.g., a host cell). In certain cases, an expression vector is utilized. An expression vector is a nucleic acid molecule containing a polynucleotide of interest encoding a polypeptide, peptide, or polynucleotide and also containing other polynucleotides that direct and/or control the expression of the polynucleotide of interest. Expression includes, but is not limited to, processes such as transcription, translation, and/or splicing (e.g., where introns are present).

Viral vectors that may be used include, for example, retrovirus, adenovirus, adeno-associated virus (AAV), alphavirus, herpes virus, and poxvirus vectors, among others. Many such viral vectors are available in the art. The vectors described herein may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), and *PCR Protocols: A Guide to Methods and Applications* (Innis, et al. 1990. Academic Press, San Diego, Calif.).

Suitable retroviral vectors may include derivatives of lentivirus as well as derivatives of murine or avian retroviruses. Exemplary, suitable retroviral vectors may include, for example, Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of retroviral vectors can incorporate multiple exogenous polynucleotides. As recombinant retroviruses are defective, they require assistance in order to produce infectious vector particles. This assistance can be provided by, for example, helper cell lines encoding retrovirus structural genes. Suitable helper cell lines include Ψ2, PA317 and PA12, among others. The vector virions produced using such cell lines may then be used to infect a tissue cell line, such as NIH 3T3 cells, to produce large quantities of chimeric retroviral virions. Retroviral vectors may be administered by traditional methods (i.e., injection) or by implantation of a "producer cell line" in proximity to the target cell population (Culver, K., et al., 1994, *Hum. Gene Ther.*, 5 (3): 343-79; Culver, K., et al., *Cold Spring Harb. Symp. Quant. Biol.*, 59: 685-90); Oldfield, E., 1993, *Hum. Gene Ther.*, 4 (1): 39-69). The producer cell line is engineered to produce a viral vector and releases viral particles in the vicinity of the target cell. A portion of the released viral particles contact the target cells and infect those cells, thus delivering a nucleic acid encoding an immunogen to the target cell. Following infection of the target cell, expression of the polynucleotide of interest from the vector occurs.

Adenoviral vectors have proven especially useful for gene transfer into eukaryotic cells (Rosenfeld, M., et al., 1991, Science, 252 (5004): 431-4; Crystal, R., et al., 1994, Nat. Genet., 8 (1): 42-51), the study eukaryotic gene expression (Levrero, M., et al., 1991, Gene, 101 (2): 195-202), vaccine development (Graham, F. and Prevec, L., 1992, Biotechnology, 20: 363-90), and in animal models (Stratford-Perricaudet, L., et al., 1992, Bone Marrow Transplant., 9 (Suppl. 1): 151-2; Rich, et al., 1993, Hum. Gene Ther., 4 (4): 461-76). Experimental routes for administrating recombinant Ad to different tissues in vivo have included intratracheal instillation (Rosenfeld, M., et al., 1992, *Cell*, 68 (1): 143-55) injection into muscle (Quantin, B., et al., 1992, *Proc. Natl. Acad. Sci. U.S.A.*, 89 (7): 2581-4), peripheral intravenous injection (Herz, J., and Gerard, R., 1993, *Proc. Natl. Acad. Sci. U.S.A.*, 90 (7): 2812-6) and/or stereotactic inoculation to brain (Le Gal La Salle, G., et al., 1993, *Science*, 259 (5097): 988-90), among others.

Adeno-associated virus (AAV) demonstrates high-level infectivity, broad host range and specificity in integrating into the host cell genome (Hermonat, P., et al., 1984, *Proc. Natl. Acad. Sci. U.S.A.*, 81 (20): 6466-70). And Herpes Simplex Virus type-1 (HSV-1) is yet another attractive vector system, especially for use in the nervous system because of its neurotropic property (Geller, A., et al., 1991, *Trends Neurosci.*, 14 (10): 428-32; Glorioso, et al., 1995, *Mol. Biotechnol.*, 4 (1): 87-99; Glorioso, et al., 1995, *Annu. Rev. Microbiol.*, 49: 675-710).

Alphavirus may also be used to express the immunogen in a host. Suitable members of the Alphavirus genus include, among others, Sindbis virus, Semliki Forest virus (SFV), the Ross River virus and Venezuelan, Western and Eastern equine encephalitis viruses, among others. Expression systems utilizing alphavirus vectors are described in, for example, U.S. Pat. Nos. 5,091,309; 5,217,879; 5,739,026; 5,766,602; 5,843,723; 6,015,694; 6,156,558; 6,190,666;

6,242,259; and, 6,329,201; WO 92/10578; Xiong et al., Science, Vol 243, 1989, 1188-1191; Liliestrom, et al. Bio/Technology, 9: 1356-1361, 1991. Thus, the use of alphavirus as an expression system is well known by those of skill in the art.

Poxvirus is another useful expression vector (Smith, et al. 1983, Gene, 25 (1): 21-8; Moss, et al, 1992, Biotechnology, 20: 345-62; Moss, et al, 1992, Curr. Top. Microbiol. Immunol., 158: 25-38; Moss, et al. 1991. Science, 252: 1662-1667). The most often utilized poxyiral vectors include vaccinia and derivatives therefrom such as NYVAC and MVA, and members of the avipox genera such as fowlpox, canarypox, ALVAC, and ALVAC(2), among others.

An exemplary suitable vector is NYVAC (vP866) which was derived from the Copenhagen vaccine strain of vaccinia virus by deleting six nonessential regions of the genome encoding known or potential virulence factors (see, for example, U.S. Pat. Nos. 5,364,773 and 5,494,807). The deletion loci were also engineered as recipient loci for the insertion of foreign genes. The deleted regions are: thymidine kinase gene (TK; J2R); hemorrhagic region (u; B13R+B14R); A type inclusion body region (AT1; A26L); hemagglutinin gene (HA; A56R); host range gene region (C7L-K1L); and, large subunit, ribonucleotide reductase (14L). NYVAC is a genetically engineered vaccinia virus strain that was generated by the specific deletion of eighteen open reading frames encoding gene products associated with virulence and host range. NYVAC has been show to be useful for expressing TAs (see, for example, U.S. Pat. No. 6,265,189). NYVAC (vP866), vP994, vCP205, vCP1433, placZH6H4Lreverse, pMPC6H6K3E3 and pC3H6FHVB were also deposited with the ATCC under the terms of the Budapest Treaty, accession numbers VR-2559, VR-2558, VR-2557, VR-2556, ATCC-97913, ATCC-97912, and ATCC-97914, respectively.

Another suitable virus is the Modified Vaccinia Ankara (MVA) virus which was generated by 516 serial passages on chicken embryo fibroblasts of the Ankara strain of vaccinia virus (CVA) (for review see Mayr, A., et al. Infection 3, 6-14 (1975)). It was shown in a variety of animal models that the resulting MVA was significantly avirulent (Mayr, A. & Danner, K. [1978] Dev. Biol. Stand. 41: 225.34) and has been tested in clinical trials as a smallpox vaccine (Mayr et al., Zbl. Bakt. Hyg. I, Abt. Org. B 167, 375-390 (1987), Stickl et al., Dtsch. med. Wschr. 99, 2386-2392 (1974)). MVA has also been engineered for use as a viral vector for both recombinant gene expression studies and as a recombinant vaccine (Sutter, G. et al. (1994), Vaccine 12: 1032-40; Blanchard et al., 1998, J Gen Virol 79, 1159-1167; Carroll & Moss, 1997, Virology 238, 198-211; Altenberger, U.S. Pat. No. 5,185,146; Ambrosini et al., 1999, J Neurosci Res 55(5), 569). Modified virus Ankara (MVA) has been previously described in, for example, U.S. Pat. Nos. 5,185,146 and 6,440,422; Sutter, et al. (B. Dev. Biol. Stand. Basel, Karger 84:195-200 (1995)); Antoine, et al. (Virology 244: 365-396, 1998); Sutter et al. (Proc. Natl. Acad. Sci. USA 89: 10847-10851, 1992); Meyer et al. (J. Gen. Virol. 72: 1031-1038, 1991); Mahnel, et al. (Berlin Munch. Tierarztl. Wochenschr. 107: 253-256, 1994); Mayr et al. (Zbl. Bakt. Hyg. I, Abt. Org. B 167: 375-390 (1987); and, Stickl et al. (Dtsch. med. Wschr. 99: 2386-2392 (1974)). An exemplary MVA is available from the ATCC under accession numbers VR-1508 and VR-1566.

ALVAC-based recombinant viruses (i.e., ALVAC-1 and ALVAC-2) are also suitable for use in practicing the present invention (see, for example, U.S. Pat. No. 5,756,103). ALVAC(2) is identical to ALVAC(1) except that ALVAC(2) genome comprises the vaccinia E3L and K3L genes under the control of vaccinia promoters (U.S. Pat. No. 6,130,066; Beattie et al., 1995a, 1995b, 1991; Chang et al., 1992; Davies et al., 1993). Both ALVAC(1) and ALVAC(2) have been demonstrated to be useful in expressing foreign DNA sequences, such as TAs (Tartaglia et al., 1993 a, b; U.S. Pat. No. 5,833,975). ALVAC was deposited under the terms of the Budapest Treaty with the American Type Culture Collection (ATCC), 10801 University Boulevard, Manassas, Va. 20110-2209, USA, ATCC accession number VR-2547. Vaccinia virus host range genes (e.g., C18L, C17L, C7L, K1L, E3L, B4R, B23R, and B24R) have also been shown to be expressible in canarypox (e.g., U.S. Pat. No. 7,473,536).

Another useful poxvirus vector is TROVAC. TROVAC refers to an attenuated fowlpox that was a plaque-cloned isolate derived from the FP-1 vaccine strain of fowlpoxvirus which is licensed for, vaccination of 1 day old chicks. TROVAC was likewise deposited under the terms of the Budapest Treaty with the ATCC, accession number 2553.

"Non-viral" plasmid vectors may also be suitable for use. Plasmid DNA molecules comprising expression cassettes for expressing an immunogen may be used for "naked DNA" immunization. Preferred plasmid vectors are compatible with bacterial, insect, and/or mammalian host cells. Such vectors include, for example, PCR-II, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT pub. No. WO 90/14363) and pFastBacDual (Gibco-BRL, Grand Island, N.Y.) as well as Bluescript® plasmid derivatives (a high copy number COLE1-based phagemid, Stratagene Cloning Systems, La Jolla, Calif.), PCR cloning plasmids designed for cloning Taq-amplified PCR products (e.g., TOPO™ TA Cloning® kit, PCR2.1® plasmid derivatives, Invitrogen, Carlsbad, Calif.).

Bacterial vectors may also be suitable for use. These vectors include, for example, Shigella, Salmonella, Vibrio cholerae, Lactobacillus, Bacille calmette guèrin (BCG), and Streptococcus (see for example, WO 88/6626; WO 90/0594; WO 91/13157; WO 92/1796; and WO 92/21376). Many other non-viral plasmid expression vectors and systems are known in the art and could be used with the current invention.

The polynucleotides and polypeptides referred to herein as being suitable for use and/or modification (e.g., SEQ ID NOS. 1-28) may be inserted into non-homologous vector genomes. For instance, while the polynucleotides and polypeptides of SEQ ID NOS. 1-28 may be derived from vaccinia, any one or more of such polynucleotides and/or polypeptides may be incorporated into and/or expressed within a different viral (e.g., MVA, ALVAC, ALVAC(2), TROVAC), bacterial or plasmid vector. If such different vectors contain sequence homologous to one or more of SEQ ID NOS. 1-28, such sequence may be replaced by a polynucleotide encoding SEQ ID NOS. 1-28. Such vectors may further comprise or be modified to comprise a polynucleotide encoding SEQ ID NO. 29, such as SEQ ID NO. 30.

Expression vectors typically comprise one or more flanking polynucleotides "operably linked" to a heterologous polynucleotide encoding a polypeptide. As used herein, the term "operably linked" refers to a linkage between polynucleotide elements in a functional relationship such as when promoter or enhancer affects transcription of a polynucleotide of interest (e.g., a coding sequence). Flanking polynucleotides may be homologous (e.g., from the same species and/or strain as the host cell), heterologous (e.g., from a species other than the host cell species and/or strain), hybrid (e.g., a combination of flanking sequences from more than one source), or synthetic, for example. All polynucleotides referred to herein are typically incorporated into vectors in expressible form, meaning that such polynucleotides are capable of being expressed from the expression vector transformed into a cell or after incorporation of the expression vector or portions thereof into the genome of an infected or transformed cell, such that the polypeptide encoded thereby is expressed in the infected or transformed cell. The flanking sequences described herein typically assist in achieving expression in the infected or transformed cell.

In certain embodiments, it is preferred that the flanking polynucleotide includes a transcriptional regulatory region that drives expression of a polynucleotide of interest in an environment such as a target cell. The transcriptional regulatory region may comprise, for example, a promoter, enhancer, silencer, repressor element, or combinations thereof. The transcriptional regulatory region may be either constitutive, tissue-specific, cell-type specific (e.g., the region is drives higher levels of transcription in a one type of tissue or cell as compared to another) and/or regulatable (e.g., responsive to interaction with a compound such as tetracycline). The source of a transcriptional regulatory region may be any prokaryotic or eukaryotic organism, any vertebrate or invertebrate organism, or any plant, provided that the flanking polynucleotide functions in an environment (e.g., a cell) by causing transcription of a polynucleotide within that environment. A wide variety of suitable transcriptional regulatory regions are available to one of skill in the art.

Suitable transcriptional regulatory regions include, for example, the synthetic e/l promoter; the CMV promoter (e.g., the CMV-immediate early promoter); promoters from eukaryotic genes (e.g., the estrogen-inducible chicken ovalbumin gene, the interferon genes, the gluco-corticoid-inducible tyrosine aminotransferase gene, and the thymidine kinase gene); and the major early and late adenovirus gene promoters; the sv40 early promoter region (Bernoist, et al. Nature 290:304-10 (1981)); the promoter contained in the 3' long terminal repeat (LTR) of Rous sarcoma virus (RSV) (Yamamoto, et al., 1980, cell 22:787-97); the herpes simplex virus thymidine kinase (HSV-TK) promoter (Wagner et al., Proc. Natl. Acad. Sci. USA, 78:1444-45 (1981)); the regulatory sequences of the metallothionine gene (Brinster et al. Nature 296:39-42 (1982)); prokaryotic expression vectors such as the beta-lactamase promoter (Villa-kamaroff et al., Proc. Natl. Acad. Sci. USA, 75:3727-31 (1978)); or, the tac promoter (Deboer et al. Proc. Natl. Acad. Sci. U.s.a., 80:21-25 (1983)). Tissue- and/or cell-type specific transcriptional control regions include, for example, the elastase I gene control region which is active in pancreatic acinar cells (Swift et al. Cell 38:639-46 (1984); Ornitz, et al. Cold Spring Harbor Symp. Quant. Biol. 50:399-409 (1986); Macdonald, et al. Hepatology 7:425-515 (1987)); the insulin gene control region which is active in pancreatic beta cells (Hanahan, et al. Nature 315:115-22 (1985)); the immunoglobulin gene control region which is active in lymphoid cells (Grosschedl et al. Cell 38:647-58 (1984); Adames et al. Nature 318:533-38 (1985); Alexander et al., Mol. Cell. Biol., 7:1436-44 (1987)); the mouse mammary tumor virus control region in testicular, breast, lymphoid and mast cells (Leder et al. Cell 45:485-95 (1986)); the albumin gene control region in liver (Pinkert et al. Genes and Devel. 1:268-76 (1987)); the alpha-feto-protein gene control region in liver (Krumlauf et al. Mol. Cell. Biol., 5:1639-48 (1985); Hammer et al. Science 235:53-58 (1987)); the alpha 1-antitrypsin gene control region in liver (Kelsey et al. Genes and Devel. 1:161-71 (1987)); the beta-globin gene control region in myeloid cells (Mogram et al. Nature 315:338-40 (1985); Kollias et al. Cell 46:89-94 (1986)); the myelin basic protein gene control region in oligodendrocyte cells in the brain (Readhead et al. Cell 48:703-12 (1987)); the myosin light chain-2 gene control region in skeletal muscle (Sani, et al. Nature 314:283-86 (1985)); the gonadotropic releasing hormone gene control region in the hypothalamus (Mason et al. Science 234:1372-78 (1986)), and the tyrosinase promoter in melanoma cells (Hart, et al. Semin. Oncol. February; 23(1):154-8 (1996); Siders, et al. Cancer Gene Ther. September-October, 5(5):281-91 (1998)), among others. Other suitable promoters are known in the art.

Nucleic acid delivery or transformation techniques that may be used include DNA-ligand complexes, adenovirus-ligand-DNA complexes, direct injection of DNA, $CaPO_4$ precipitation, gene gun techniques, electroporation, and colloidal dispersion systems, among others. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome, which are artificial membrane vesicles useful as delivery vehicles in vitro and in vivo. RNA, DNA and intact virions can be encapsulated within the aqueous interior and be delivered to cells in a biologically active form (Fraley, R., et al. *Trends Biochem. Sci.*, 6: 77 (1981)). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

Strategies for improving the efficiency of nucleic acid-based immunization may also be used including, for example, the use of self-replicating viral replicons (Caley, et al. Vaccine, 17: 3124-2135 (1999); Dubensky, et al. Mol. Med. 6: 723-732 (2000); Leitner, et al. Cancer Res. 60: 51-55 (2000)), codon optimization (Liu, et al. Mol. Ther., 1: 497-500 (2000); Dubensky, supra; Huang, et al. J. Virol. 75: 4947-4951 (2001)), in vivo electroporation (Widera, et al. J. Immunol. 164: 4635-3640 (2000)), incorporation of CpG stimulatory motifs (Gurunathan, et al. Ann. Rev. Immunol. 18: 927-974 (2000); Leitner, supra), sequences for targeting of the endocytic or ubiquitin-processing pathways (Thomson, et al. J. Virol. 72: 2246-2252 (1998); Velders, et al. J. Immunol. 166: 5366-5373 (2001)), prime-boost regimens (Gurunathan, supra; Sullivan, et al. Nature, 408: 605-609 (2000); Hanke, et al. Vaccine, 16: 439-445 (1998); Amara, et al. Science, 292: 69-74 (2001)), and the use of mucosal delivery vectors such as *Salmonella* (Darji, et al. Cell, 91: 765-775 (1997); Woo, et al. Vaccine, 19: 2945-2954 (2001)). Other methods are known in the art, some of which are described below.

In other embodiments, it may be advantageous to combine or include within the compositions or recombinant vectors additional polypeptides, peptides or polynucleotides encoding one or more polypeptides or peptides that function as "co-stimulatory" component(s). Such co-stimulatory components may include, for example, cell surface proteins, cytokines or chemokines in a composition of the present invention. The co-stimulatory component may be included in the composition as a polypeptide or peptide, or as a polynucleotide encoding the polypeptide or peptide, for example. Suitable co-stimulatory molecules may include, for example, polypeptides that bind members of the CD28 family (i.e., CD28, ICOS; Hutloff, et al. Nature 1999, 397: 263-265; Peach, et al. J Exp Med 1994, 180: 2049-2058) such as the CD28 binding polypeptides B7.1 (CD80; Schwartz, 1992; Chen et al, 1992; Ellis, et al. J. Immunol., 156(8): 2700-9) and B7.2 (CD86; Ellis, et al. J. Immunol., 156(8): 2700-9); polypeptides which bind members of the integrin family (i.e., LFA-1 (CD11a/CD18); Sedwick, et al. J Immunol 1999, 162: 1367-1375; Wülfing, et al. Science 1998, 282: 2266-2269; Lub, et al. Immunol Today 1995, 16: 479-483) including members of the ICAM family (i.e., ICAM-1, -2 or -3); polypeptides which bind CD2 family members (i.e., CD2, signalling lymphocyte activation molecule (CDw150 or "SLAM"; Aversa, et al. J Immunol 1997, 158: 4036-4044) such as CD58 (LFA-3; CD2 ligand; Davis, et al. Immunol Today 1996, 17: 177-187) or SLAM ligands (Sayos, et al. Nature 1998, 395: 462-469); polypeptides which bind heat stable antigen (HSA or CD24; Zhou, et al. Eur J Immunol 1997, 27: 2524-2528); polypeptides which bind to members of the TNF receptor (TNFR) family (i.e., 4-1BB (CD137; Vinay, et al. Semin Immunol 1998, 10: 481-489)), OX40 (CD134; Weinberg, et al. Semin Immunol 1998, 10: 471-480; Higgins, et al. J Immunol 1999, 162: 486-493), and CD27 (Lens, et al. Semin Immunol 1998, 10: 491-499)) such as 4-1BBL (4-IBB ligand; Vinay, et al. Semin Immunol 1998, 10: 481-48; DeBenedette, et al. J Immunol 1997, 158: 551-559), TNFR associated factor-1 (TRAF-1; 4-IBB ligand; Saoulli, et al. J Exp Med 1998, 187: 1849-1862, Arch, et al. Mol Cell Biol 1998, 18: 558-565), TRAF-2 (4-IBB and OX40 ligand; Saoulli, et al. J Exp Med 1998, 187: 1849-1862; Oshima, et al. Int Immunol 1998, 10: 517-526, Kawamata, et al. J Biol Chem 1998, 273: 5808-5814), TRAF-3 (4-1BB and OX40 ligand; Arch, et al. Mol Cell Biol 1998, 18: 558-565; Jang, et al. Biochem Biophys Res Commun 1998, 242: 613-620; Kawamata S. et al. J Biol Chem 1998, 273: 5808-5814), OX40L (OX40 ligand; Gramaglia, et al. J Immunol 1998, 161: 6510-6517), TRAF-5 (OX40 ligand; Arch, et al. Mol Cell Biol 1998, 18: 558-565; Kawamata, et al. J Biol Chem 1998, 273: 5808-5814), and CD70 (CD27 ligand; Couderc, et al. Cancer Gene Ther., 5(3): 163-75). CD154 (CD40 ligand or "CD40L"; Gurunathan, et al. J. Immunol., 1998, 161: 4563-4571; Sine, et al. Hum. Gene Ther., 2001, 12: 1091-1102) Other co-stimulatory molecules may also be suitable for practicing the present invention.

One or more cytokines may also be suitable co-stimulatory components or "adjuvants", either as polypeptides or being encoded by polynucleotides contained within the compositions of the present invention (Parmiani, et al. Immunol Lett 2000 Sep. 15; 74(1): 41-4; Berzofsky, et al. Nature Immunol. 1: 209-219). Suitable cytokines include, for example, interleukin-2 (IL-2) (Rosenberg, et al. Nature Med. 4: 321-327 (1998)), IL-4, IL-7, IL-12 (reviewed by Pardoll, 1992; Harries, et al. J. Gene Med. 2000 July-August; 2(4):243-9; Rao, et al. J. Immunol. 156: 3357-3365 (1996)), IL-15 (Xin, et al. Vaccine, 17:858-866, 1999), IL-16 (Cruikshank, et al. J. Leuk Biol. 67(6): 757-66, 2000), IL-18 (J. Cancer Res. Clin. Oncol. 2001. 127(12): 718-726), GM-CSF (CSF (Disis, et al. Blood, 88: 202-210 (1996)), tumor necrosis factor-alpha (TNF-α), or interferon-gamma (INF-γ). Other cytokines may also be suitable for practicing the present invention.

Chemokines may also be utilized. For example, fusion proteins comprising CXCL10 (IP-10) and CCL7 (MCP-3) fused to a tumor self-antigen have been shown to induce anti-tumor immunity (Biragyn, et al. Nature Biotech. 1999, 17: 253-258). The chemokines CCL3 (MIP-1α) and CCL5 (RANTES) (Boyer, et al. Vaccine, 1999, 17 (Supp. 2): S53-S64) may also be of use. Other suitable chemokines are known in the art.

It is also known in the art that suppressive or negative regulatory immune mechanisms may be blocked, resulting in enhanced immune responses. For instance, treatment with anti-CTLA-4 (Shrikant, et al. Immunity, 1996, 14: 145-155; Sutmuller, et al. J. Exp. Med., 2001, 194: 823-832), anti-CD25 (Sutmuller, supra), anti-CD4 (Matsui, et al. J. Immunol., 1999, 163: 184-193), the fusion protein IL13Rα2-Fc (Terabe, et al. Nature Immunol., 2000, 1: 515-520), and combinations thereof (i.e., anti-CTLA-4 and anti-CD25, Sutmuller, supra) have been shown to upregulate anti-tumor immune responses and would be suitable in practicing the present invention.

An immunogen may also be administered in combination with one or more adjuvants to boost the immune response. Adjuvants may also be included to stimulate or enhance the immune response. Non-limiting examples of suitable adjuvants include those of the gel-type (i.e., aluminum hydroxide/phosphate ("alum adjuvants"), calcium phosphate), of microbial origin (muramyl dipeptide (MDP)), bacterial exotoxins (cholera toxin (CT), native cholera toxin subunit B (CTB), *E. coli* labile toxin (LT), pertussis toxin (PT), CpG oligonucleotides, BCG sequences, tetanus toxoid, monophosphoryl lipid A (MPL) of, for example, *E. coli, Salmonella minnesota, Salmonella typhimurium*, or *Shigella exseri*), particulate adjuvants (biodegradable, polymer microspheres), immunostimulatory complexes (ISCOMs)), oil-emulsion and surfactant-based adjuvants (Freund's incomplete adjuvant (FIA), microfluidized emulsions (MF59, SAF), saponins (QS-21)), synthetic (muramyl peptide derivatives (murabutide, threony-MDP), nonionic block copolymers (L121), polyphosphazene (PCCP), synthetic polynucleotides (poly A:U, poly I:C), thalidomide derivatives (CC-4407/ACTIMID)), RH3-ligand, or polylactide glycolide (PLGA) microspheres, among others. Fragments, homologs, derivatives, and fusions to any of these toxins are also suitable, provided that they retain adjuvant activity. Suitable mutants or variants of adjuvants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that can be used in the methods and compositions of the invention include, e.g., Ser-63-Lys, Ala-69-Gly, Glu-110-Asp, and Glu-112-Asp mutants. Other suitable adjuvants are also well-known in the art.

As an example, metallic salt adjuvants such alum adjuvants are well-known in the art as providing a safe excipient with adjuvant activity. The mechanism of action of these adjuvants are thought to include the formation of an antigen depot such that antigen may stay at the site of injection for up to 3 weeks after administration, and also the formation of antigen/metallic salt complexes which are more easily taken up by antigen presenting cells. In addition to aluminium, other metallic salts have been used to adsorb antigens, including salts of zinc, calcium, cerium, chromium, iron, and berilium. The hydroxide and phosphate salts of aluminium are the most common. Formulations or compositions containing aluminium salts, antigen, and an additional immunostimulant are known in the art. An example of an immunostimulant is 3-de-O-acylated monophosphoryl lipid A (3D-MPL).

Any of these components may be used alone or in combination with other agents. For instance, it has been shown that a combination of CD80, ICAM-1 and LFA-3 ("TRICOM") may potentiate anti-cancer immune responses (Hodge, et al. Cancer Res. 59: 5800-5807 (1999). Other effective combinations include, for example, IL-12+GM-CSF (Ahlers, et al. J. Immunol., 158: 3947-3958 (1997); Iwasaki, et al. J. Immunol. 158: 4591-4601 (1997)), IL-12+ GM-CSF+TNF-α (Ahlers, et al. Int. Immunol. 13: 897-908 (2001)), CD80+IL-12 (Fruend, et al. Int. J. Cancer, 85: 508-517 (2000); Rao, et al. supra), and CD86+GM-CSF+ IL-12 (Iwasaki, supra). One of skill in the art would be aware of additional combinations useful in carrying out the present invention. In addition, the skilled artisan would be aware of additional reagents or methods that may be used to modulate such mechanisms. These reagents and methods, as well as others known by those of skill in the art, may be utilized in practicing the present invention.

Other agents that may be utilized in conjunction with the compositions and methods provided herein include anti-infective agents (e.g., antibiotics, anti-viral medications). For example, with respect to HIV, agents including, for example, protease inhibitor, an HIV entry inhibitor, a reverse transcriptase inhibitor, and/or an anti-retroviral nucleoside analog. Suitable compounds include, for example, Agenerase (amprenavir), Combivir (Retrovir/Epivir), Crixivan (indinavir), Emtriva (emtricitabine), Epivir (3tc/lamivudine), Epzicom, Fortovase/Invirase (saquinavir), Fuzeon (enfuvirtide), Hivid (ddc/zalcitabine), Kaletra (lopinavir), Lexiva (Fosamprenavir), Norvir (ritonavir), Rescriptor (delavirdine), Retrovir/AZT (zidovudine), Reyatax (atazanavir, BMS-232632), Sustiva (efavirenz), Trizivir (abacavir/zidovudine/lamivudine), Truvada (Emtricitabine/Tenofovir DF), Videx (ddI/didanosine), Videx EC (ddI, didanosine), Viracept (nevirapine), Viread (tenofovir disoproxil fumarate), Zerit (d4T/stavudine), and Ziagen (abacavir) may be utilized. Other suitable agents are known to those of skill in the art. Such agents may either be used prior to, during, or after administration of the compositions and/or use of the methods described herein.

Other agents that may be utilized in conjunction with the compositions and methods provided herein include chemotherapeutics and the like (e.g., chemotherapeutic agents, radiation, anti-angiogenic compounds (Sebti, et al. Oncogene 2000 Dec. 27; 19(56):6566-73)). For example, in treating metastatic breast cancer, useful chemotherapeutic agents include cyclophosphamide, doxorubicin, paclitaxel, docetaxel, navelbine, capecitabine, and mitomycin C, among others. Combination chemotherapeutic regimens have also proven effective including cyclophosphamide+ methotrexate+5-fluorouracil; cyclophosphamide+doxorubicin+5-fluorouracil; or, cyclophosphamide+doxorubicin, for example. Other compounds such as prednisone, a taxane, navelbine, mitomycin C, or vinblastine have been utilized for various reasons. A majority of breast cancer patients have estrogen-receptor positive (ER+) tumors and in these patients, endocrine therapy (i.e., tamoxifen) is preferred over chemotherapy. For such patients, tamoxifen or, as a second line therapy, progestins (medroxyprogesterone acetate or megestrol acetate) are preferred. Aromatase inhibitors (i.e., aminoglutethimide and analogs thereof such as letrozole) decrease the availability of estrogen needed to maintain tumor growth and may be used as second or third line endocrine therapy in certain patients.

Other cancers may require different chemotherapeutic regimens. For example, metastatic colorectal cancer is typically treated with Camptosar (irinotecan or CPT-11), 5-fluorouracil or leucovorin, alone or in combination with one another. Proteinase and integrin inhibitors such as the MMP inhibitors marimastate (British Biotech), COL-3 (Collagenex), Neovastat (Aeterna), AG3340 (Agouron), BMS-275291 (Bristol Myers Squibb), CGS 27023A (Novartis) or the integrin inhibitors Vitaxin (Medimmune), or MED1522 (Merck KgaA) may also be suitable for use. As such, immunological targeting of immunogenic targets associated with colorectal cancer could be performed in combination with a treatment using those chemotherapeutic agents. Similarly, chemotherapeutic agents used to treat other types of cancers are well-known in the art and may also be suitable for use.

Many anti-angiogenic agents are known in the art may also be used in combination with the recombinant vectors described herein (see, for example, Timar, et al. 2001. Pathology Oncol. Res., 7(2): 85-94). Such agents include, for example, physiological agents such as growth factors (i.e., ANG-2, NK1, 2, 4 (HGF), transforming growth factor beta (TGF-β)), cytokines (i.e., interferons such as IFN-α, -β, -γ, platelet factor 4 (PF-4), PR-39), proteases (i.e., cleaved AT-III, collagen XVIII fragment (Endostatin)), HmwKallikrein-d5 plasmin fragment (Angiostatin), prothrombin-F1-2, TSP-1), protease inhibitors (i.e., tissue inhibitor of metalloproteases such as TIMP-1, -2, or -3; maspin; plasminogen activator-inhibitors such as PAI-1; pigment epithelium derived factor (PEDF)), Tumstatin (available through ILEX, Inc.), antibody products (i.e., the collagen-binding antibodies HUIV26, HUI77, XL313; anti-VEGF; anti-integrin (i.e., Vitaxin, (Lxsys))), and glycosidases (i.e., heparinase-I, -III). "Chemical" or modified physiological agents known or believed to have anti-angiogenic potential include, for example, vinblastine, taxol, ketoconazole, thalidomide, dolestatin, combrestatin A, rapamycin (Guba, et al. 2002, Nature Med., 8: 128-135), CEP-7055 (available from Cephalon, Inc.), flavone acetic acid, Bay 12-9566 (Bayer Corp.), AG3340 (Agouron, Inc.), CGS 27023A (Novartis), tetracycline derivatives (i.e., COL-3 (Collagenix, Inc.)), Neovastat (Aeterna), BMS-275291 (Bristol-Myers Squibb), low dose 5-FU, low dose methotrexate (MTX), irsofladine, radicicol, cyclosporine, captopril, celecoxib, D45152-sulphated polysaccharide, cationic protein (Protamine), cationic peptide-VEGF, Suramin (polysulphonated napthyl urea), compounds that interfere with the function or production of VEGF (i.e., SU5416 or SU6668 (Sugen), PTK787/ZK22584 (Novartis)), Distamycin A, Angiozyme (ribozyme), isoflavinoids, staurosporine derivatives, genistein, EMD121974 (Merck KcgaA), tyrphostins, isoquinolones, retinoic acid, carboxyamidotriazole, TNP-470, octreotide, 2-methoxyestradiol, aminosterols (i.e., squalamine), glutathione analogues (i.e., N-acetyl-L-cysteine), combretastatin A-4 (Oxigene), Eph receptor blocking agents (Nature, 414:933-938, 2001), Rh-Angiostatin, Rh-Endostatin (WO 01/93897), cyclic-RGD peptide, accutin-disintegrin, benzodiazepenes, humanized anti-avb3 Ab, Rh-PAI-2, amiloride, p-amidobenzamidine, anti-uPA ab, anti-uPAR Ab, L-phanylalanin-N-methylamides (i.e.; Batimistat, Marimastat), AG3340, and minocycline. Other suitable agents are known in the art and may be suitable for use.

Administration of a composition of the present invention to a host may be accomplished using any of a variety of techniques known to those of skill in the art. The composition(s) may be processed in accordance with conventional methods of pharmacy to produce medicinal agents for administration to patients, including humans and other mammals (i.e., a "pharmaceutical composition"). The pharmaceutical composition is preferably made in the form of a dosage unit containing a given amount of DNA, viral vector particles, polypeptide, peptide, or other drug candidate, for example. A suitable daily dose for a human or other mammal may vary widely depending on the condition of the patient and other factors, but, once again, can be determined using routine methods. The compositions are administered to a patient in a form and amount sufficient to elicit a therapeutic effect. Amounts effective for this use will depend on various factors, including for example, the particular composition of the vaccine regimen administered, the manner of administration, the stage and severity of the disease, the general state of health of the patient, and the judgment of the prescribing physician. The dosage regimen for immunizing a host or otherwise treating a disorder or a disease with a composition of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods.

In general, recombinant viruses may be administered in compositions in an amount of about $10^4$ to about $10^9$ pfu per inoculation; often about $10^4$ pfu to about $10^6$ pfu, or as shown in the Examples, $10^7$ to $10^3$ pfu. Higher dosages such as about $10^4$ pfu to about $10^{10}$ pfu, e.g., about $10^5$ pfu to about $10^9$ pfu, or about $10^6$ pfu to about $10^8$ pfu, or about $10^7$ pfu can also be employed. Another measure commonly used is $DICC_{50}$; suitable $DICC_{50}$ ranges for administration include about $10^1$, about $10^2$, about $10^3$, about $10^4$, about $10^5$, about $10^6$, about $10^7$, about $10^8$, about $10^9$, about $10^{10}$ $DICC_{50}$. Ordinarily, suitable quantities of plasmid or naked DNA are about 1 µg to about 100 mg, about 1 mg, about 2 mg, but lower levels such as 0.1 to 1 mg or 1-10 µg may be employed. Actual dosages of such compositions can be readily determined by one of ordinary skill in the field of vaccine technology.

The pharmaceutical composition may be administered orally, parentally, by inhalation spray, rectally, intranodally, or topically in dosage unit formulations containing conventional pharmaceutically acceptable carriers, adjuvants, and vehicles. The term "pharmaceutically acceptable carrier" or "physiologically acceptable carrier" as used herein refers to one or more formulation materials suitable for accomplishing or enhancing the delivery of a nucleic acid, polypeptide, or peptide as a pharmaceutical composition. A "pharmaceutical composition" is a composition comprising a therapeutically effective amount of a nucleic acid or polypeptide. The terms "effective amount" and "therapeutically effective amount" each refer to the amount of a nucleic acid or polypeptide used to observe the desired therapeutic effect (e.g., induce or enhance and immune response).

Injectable preparations, such as sterile injectable aqueous or oleaginous suspensions, may be formulated according to known methods using suitable dispersing or wetting agents and suspending agents. The injectable preparation may also be a sterile injectable solution or suspension in a non-toxic parenterally acceptable diluent or solvent. Suitable vehicles and solvents that may be employed are water, Ringer's solution, and isotonic sodium chloride solution, among others. For instance, a viral vector such as a poxvirus may be prepared in 0.4% NaCl or a Tris-HCl buffer, with or without a suitable stabilizer such as lactoglutamate, and with or without freeze drying medium. In addition, sterile, fixed oils are conventionally employed as a solvent or suspending medium. For this purpose, any bland fixed oil may be employed, including synthetic mono- or diglycerides. In addition, fatty acids such as oleic acid find use in the preparation of injectables.

Pharmaceutical compositions may take any of several forms and may be administered by any of several routes. The compositions are administered via a parenteral route (e.g., intradermal, intramuscular, subcutaneous, skin scarification) to induce an immune response in the host. Alternatively, the composition may be administered directly into a lymph node (intranodal) or tumor mass (i.e., intratumoral administration). Preferred embodiments of administratable compositions include, for example, nucleic acids, viral particles, or polypeptides in liquid preparations such as suspensions, syrups, or elixirs. Preferred injectable preparations include, for example, nucleic acids or polypeptides suitable for parental, subcutaneous, intradermal, intramuscular or intravenous administration such as sterile suspensions or emulsions. For example, a naked DNA molecule and/or recombinant poxvirus may separately or together be in admixture with a suitable carrier, diluent, or excipient such as sterile water, physiological saline, glucose or the like. The composition may also be provided in lyophilized form for reconstituting, for instance, in isotonic aqueous, saline buffer. In addition, the compositions can be co-administered or sequentially administered with one another, other antiviral compounds, other anti-cancer compounds and/or compounds that reduce or alleviate ill effects of such agents.

As previously mentioned, while the compositions described herein may be administered as the sole active pharmaceutical agent, they can also be used in combination with one or more other compositions or agents (i.e., other immunogens, co-stimulatory molecules, adjuvants). When administered as a combination, the individual components can be formulated as separate compositions administered at the same time or different times, or the components can be combined as a single composition. In one embodiment, a method of administering to a host a first form of an immunogen and subsequently administering a second form of the immunogen, wherein the first and second forms are different, and wherein administration of the first form prior to administration of the second form enhances the immune response resulting from administration of the second form relative to administration of the second form alone, is provided. Also provided are compositions for administration to the host. For example, a two-part immunological composition where the first part of the composition comprises a first form of an immunogen and the second part comprises a second form of the immunogen, wherein the first and second parts are administered separately from one another such that administration of the first form enhances the immune response against the second form relative to administration of the second form alone, is provided. The immunogens, which may be the same or different, are preferably derived from the infectious agent or other source of immunogens. The multiple immunogens may be administered together or separately, as a single or multiple compositions, or in single or multiple recombinant vectors.

A kit comprising a composition of the present invention is also provided. The kit can include a separate container containing a suitable carrier, diluent or excipient. The kit may also include additional components for simultaneous or sequential-administration. In one embodiment, such a kit may include a first form of an immunogen and a second form of the immunogen. Additionally, the kit can include instructions for mixing or combining ingredients and/or administration. A kit may provide reagents for performing screening assays, such as one or more PCR primers, hybridization probes, and/or biochips, for example.

All references cited within this application are incorporated by reference. A better understanding of the present'invention and of its many advantages will be had from the following examples, given by way of illustration.

EXAMPLES

Example 1

NYVAC-HIV C Vector

The recombinant vectors DNA C and NYVAC-HIV C expressed HIV genes derived from the Chinese R5 clade C virus (97CN54; Su, et al. J. Virol. 2000. 74: 11367-76; WO 01/36614; Gomez et al., Vaccine, Vol. 25, pp. 1969-1992 (2007)). This clone has been shown to be representative of clade C strains circulating in China and India. All HIV genes have been optimised for codon usage since it has recently been shown that humanization of synthetic HIV gene codons allowed for an enhanced and REV/RRE-independent expression of env and gag-pol genes in mammalian cells. Genes were optimized for both safety and translation efficiency. The env gene has been designed to express the secreted gp120 form of the envelope proteins and contain an optimal synthetic leader sequence for enhanced expression. The gag, pol and nef genes were fused to express a GAG-POL-NEF polyprotein. An artificial −1 frameshift introduced in the natural slippery sequence of the p7-p6 gene junction results in an in-frame GAG-POL-NEF fusion protein due to the absence of ribosomal frameshift. An N-terminal Gly→Ala substitution in gag prevents the formation and release of virus-like particles from transfected cells. This strategy allows for an equimolar production of GAG, POL and NEF proteins and an enhanced MHC Class-I restricted presentation of their CTL epitopes. For safety and regulatory reason, the packaging signal sequence has been removed; the integrase gene deleted; and the reverse transcriptase gene disrupted by insertion of a scrambled nef gene at the 3' end of the DNA sequence coding for the RT active site known to be associated with an immunodominant CTL epitope. The nef gene has been dislocated by fusing its 5' half to its 3' half without losing its immunodominant CTL epitopes.

A. NYVAC-HIV-C (vP2010)

1. Donor Plasmid pMA60gp120C/gagpolnef-C-14.

Donor plasmid pMA60gp120C/GAG-POL-NEF-C-14 was constructed for engineering of NYVAC or MVA expressing HIV-1 clade C gp120 envelope and GAG-POL-NEF proteins. The plasmid is a pUC derivative containing TK left and right flanking sequences in pUC cloning sites. Between two flanking sequences two synthetic early/late (E/L) promoters in a back to back orientation individually drive codon-optimized clade C gp120 gene and gag-pol-nef gene. The locations of the TK flanking sequences, E/L promoters, transcriptional termination signal, gp120 and gag-pol-nef genes as described in Table 2 below:

TABLE 2

| pMA60gp120C/gagpolnef-C-14 | |
|---|---|
| Left flanking sequence | Nt. 1609-2110 (complementary) |
| Right flanking sequence | Nt. 4752-5433 (complementary) |
| E/L promoter for gp120 | Nt.12-51 |
| Gp120 gene (ATG-TGA) | Nt 61-1557 |
| Terminal signal for gp120 | Nt.1586-1592 |
| E/L promoter for gagpolnef | Nt. 9794-9833 (complementary) |
| gagpolnef gene (ATG-TAA) | Nt. 5531-9784 (complementary) |
| Terminal signal for gagpolnef | Nt.5422-5416 (complementary) |

2. Construction of pMA60gp120C/gagpolnef-C-14 DNA Origin:

a. pMA60:

This plasmid is a pUC derivative containing TK right and left flanking sequences in pUC cloning sites. Between the two flanking sequences there is a synthetic E/L promoter. The left flanking sequence is located at 37-550 and right flanking sequence is at 610-1329. The E/L promoter (AAAATTGAAATTTTATTTTTTTTTTTG-GAATATAAATA; SEQ ID NO. 60) is located at 680-569.

b. pCR-Script Clade C-svngp120:

The plasmid contained a codon-optimized clade C HIV-1 gp120 gene. The gp120 gene is located at nucleotides 1-1497 (ATG to TAA).

c. pCRs-Cript Clade C-syngagnolnef:

The plasmid containing a codon-optimized clade C HIV-1 gagpolnef gene was provided by Hans Wolf and Walf Wagner (Regensburg University, Germany). The gagpolnef gene was located between nucleotides 1-4473 (ATG to TAA).

d. pSE1379.7:

The plasmid is a Bluescript derivative containing a synthetic E/L promoter. The E/L promoter is located at nucleotides 1007-968.

3. Construction of pMA60 gp120C/gagpolnef-C-14:

a. Construction of pMA60-T5NT-24:

pMA60 has a synthetic E/L promoter but has no transcriptional termination signal for the promoter. To insert a terminal signal T5NT for the promoter, a DNA fragment composed of a pair of oligonucleotides, 5'-CCGGAATTTT-TATT-3'(7291) (SEQ ID NO. 61)/3'-TTAAAAATAAGGCC-5' (7292) (SEQ ID NO. 62), was inserted into Xma I site on pMA60. The resulted plasmid was designated pMA60-T5NT-24.

b. Construction of pMA60gp120C-10:

To generate a clade C gp120 gene without extra sequence between promoter and start codon ATG a KpnI-KpnI fragment (nt. 4430-1527) containing the gp120 gene was isolated from pCR-Script clade C-syngp120 and used as template in a PCR. In the PCR, primers 7490/7491 (7490: 5'-TTGAATTCTCGAGCATGGACAGGGCCAAGCT-GCTGCTGCTGCTG (SEQ ID NO. 63) and 7491: 5'-TGCTGCTCACGTTCCTGCACTCCAGGGT (SEQ ID NO. 64)) were used to amplify a ~370 bp 5'-gp120 fragment. The fragment was cut with EcoRI and AatII generating an EcoRI-AatII fragment (~300 bp). The EcoRI-AatII fragment was used to replace a corresponding EcoRI-Aat II fragment (nt. 4432-293) on pCR-Script clade C-syngp120 resulting in a plasmid pCR-Script clade Cgp120-PCR-19. A XhoI-XhoI fragment containing a gp120 gene was isolated from pCR-Script cladeCgp120-PCR-19 and cloned into XhoI site on pMA60-T5NT-24 generating pMA60gp120C-10.

c. Construction of pMA60gp120C/gagpolnef-C-14:

To create a clade C gagpolnef gene without extra sequence between promoter and stat codon of the gene a KpnI-KpnI (nt 7313-4352) fragment containing the gagpolnef gene was isolated from pCRscript-Syngagpolnef and used as template in a PCR reaction. The primers were oligonucleotides (7618: 5'TTTCTCGAGCATGGCCGC-CAGGGCCAGCATCCTGAGG (SEQ ID NO. 65)/7619: 5'-ATCTGCTCCTGCAGGTTGCTGGTGGT (SEQ ID NO. 66). A fragment (~740 bp) amplified in the PCR was cloned into Sma I site on pUC18 resulting in a plasmid designated pATGgpn-740. The ~740 bp fragment in pATGgpn-740 was confirmed by DNA sequencing. The pATGgpn-740 was cut with XhoI and StuI generating an XhoI-StuI fragment (~480 bp). In addition, pCRScript-syngagpolnef was cut with StuI and KpnI generating a StuI-KpnI fragment (nt. 479-4325). Meanwhile pSE1379.7, a Bluescript derivative containing an E/L promoter, was linearized with XhoI and KpnI generating an XhoI-KpnI receptor fragment (~3 kb). The two fragments (XhoI-Stu I and StuI-KpnI) and the receptor fragment (XhoI-KpnI) were ligated together generating a plasmid pATGgagpolnef-C-2. Finally, the pATG-gagpolnef-C-2 was cut with SalI generating a SalI-SalI fragment that contained an E/L-gagpolnef cassette. The SalI-SalI fragment was cloned into a SalI site on pMA60gp120C-10 generating pMA60gp120C/gagpolnef-C-14.

4. Generation of NYVAC-HIV-C Recombinant (vP2010; "NYVAC-C")

The IVR was performed by transfection of 1° CEF cells (Merial product) with pMA60gp120C/gagpolenef C-14 using calcium phosphate method and simultaneously infection of the cells with NYVAC as rescue virus at MOI of 10. After ~14 hr, the transfected-infected cells were harvested, sonicated and used for recombinant virus screening. Recombinant plaques were screened based on plaque lift hybridization method. A 1.5 kb clade C gp120 gene that was labeled with p32 according to a random primer labeling kit protocol (Promega) was used as probe. In the first round screening, ~11700 plaques were screened and three positive clones designated vP2010-1, vP 2010-2, vP2010-3, were obtained. After sequential four rounds of plaque purification, recombinants designated vP2010-1-2-1-1, vP2010-1-2-2-1, vP2010-1-4-1-1, vP2010-1-4-1-2 and vP2010-1-4-2-1 were generated and confirmed by hybridization as 100% positive using the gp120 probe. P2 stocks of these recombinants were prepared. A P3 (roller bottle) stock with a titer 1.2×10⁹ was prepared.

Example 2

Modified Expression Vectors

A. Immunomodulatory Vectors

The plasmid backbone used for the generation of the different plasmid transfer vectors is termed pGem-Red-GFP wm (FIG. 1) This plasmid, derived from pGem-7Zf(-) (Promega Corp.), contains two different fluorescent proteins (Red2 and rsGFP), each under the control of the vaccinia virus synthetic early/late promoter. The plasmid transfer vectors listed in Table 3 were generated by the sequential cloning of the recombination flanking sequences of the specific genes to be deleted.

TABLE 3

| Plasmid transfer vector | Deleted Gene | Recombinant Virus |
|---|---|---|
| pGem-RG-B8R wm | B8R | NYVAC-C-ΔB8R<br>NYVAC-C-ΔB8R/B19R |

TABLE 3-continued

| Plasmid transfer vector | Deleted Gene | Recombinant Virus |
|---|---|---|
| pGem-RG-B19R wm | B19R | NYVAC-C-ΔB19R<br>NYVAC-C-ΔB8R/B19R |

2. NYVAC-C-ΔB8R Recombinant Vectors

The plasmid transfer vector pGem-RG-B8R wm, used for the construction of the recombinant virus "NYVAC-C-ΔB8R", having the B8R open reading frame (e.g, SEQ ID NO. 2 encoding SEQ ID NO. 1) deleted, was obtained by sequential cloning of five DNA fragments containing dsRed2 and rsGFP genes and B8R recombination flanking sequences into the plasmid pGem-7Zf(-) (Promega). The dsRed2 gene under the control of the synthetic early/late promoter was amplified by PCR from plasmid pG-dsRed2 with oligonucleotides Red2-B (5'-GAACTAGGATCCTAA CTCGAGAAA-3'; SEQ ID NO. 67) (Bam HI site underlined) and Red2-N (5'-ATTAGT ATGCATTTATTTATTTAGG-3'; SEQ ID NO. 68) (Nsi I site underlined) (785 bp), digested with Bam HI and Nsi I and inserted into the Bam HI/Nsi I-digested pGem-7Zf(-) to generate pGem-Red wm (3740 bp). The rsGFP gene under the control of the synthetic early/late promoter was amplified by PCR from plasmid pG-dsRed2 with oligonucleotides GFP-X (5'-CGTTGGTCTAGAGAGAAAAATTG-3'; SEQ ID NO. 69) (Xba I site underlined) and GFP-E (5'-CTATA GAATTCTCAAGCTATGC-3'; SEQ ID NO. 70) (Eco RI site underlined) (832 bp), digested with Xba I and Eco RI and inserted into plasmid pGem-Red wm previously digested with Xba I and Eco RI to obtain pGem-Red-GFP wm (4540 bp).

Figure 2:
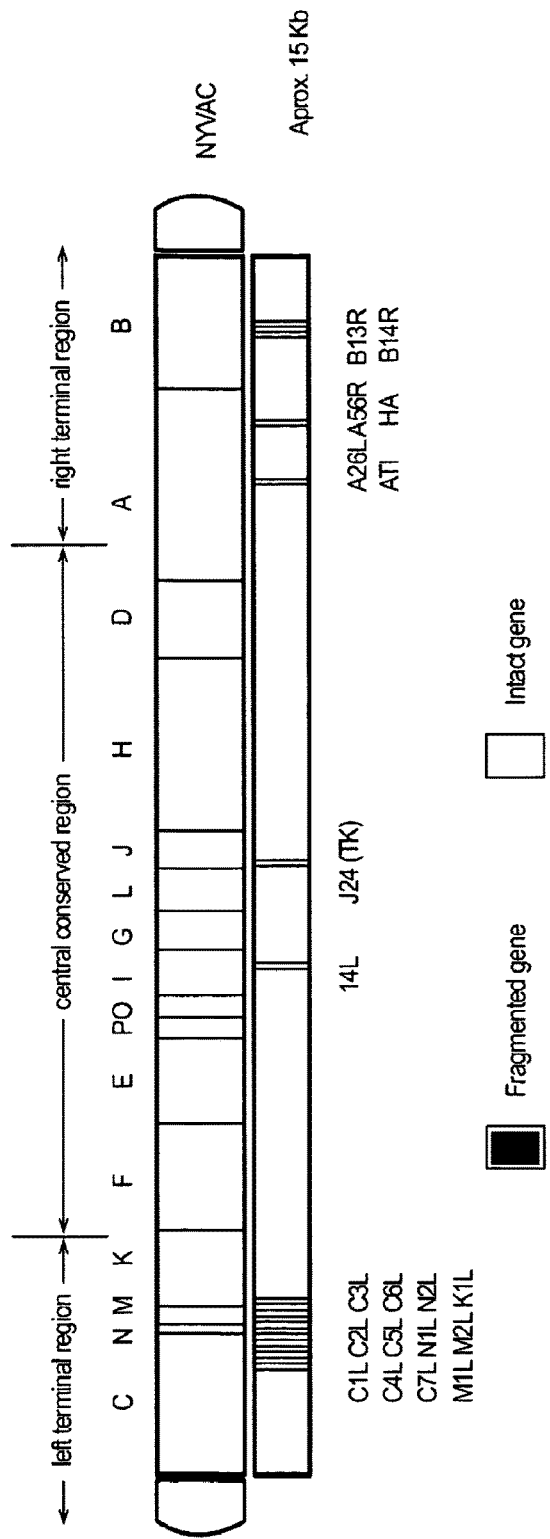
FIG. 2. Schematic representation of NYVAC genome.
Figure 3A:
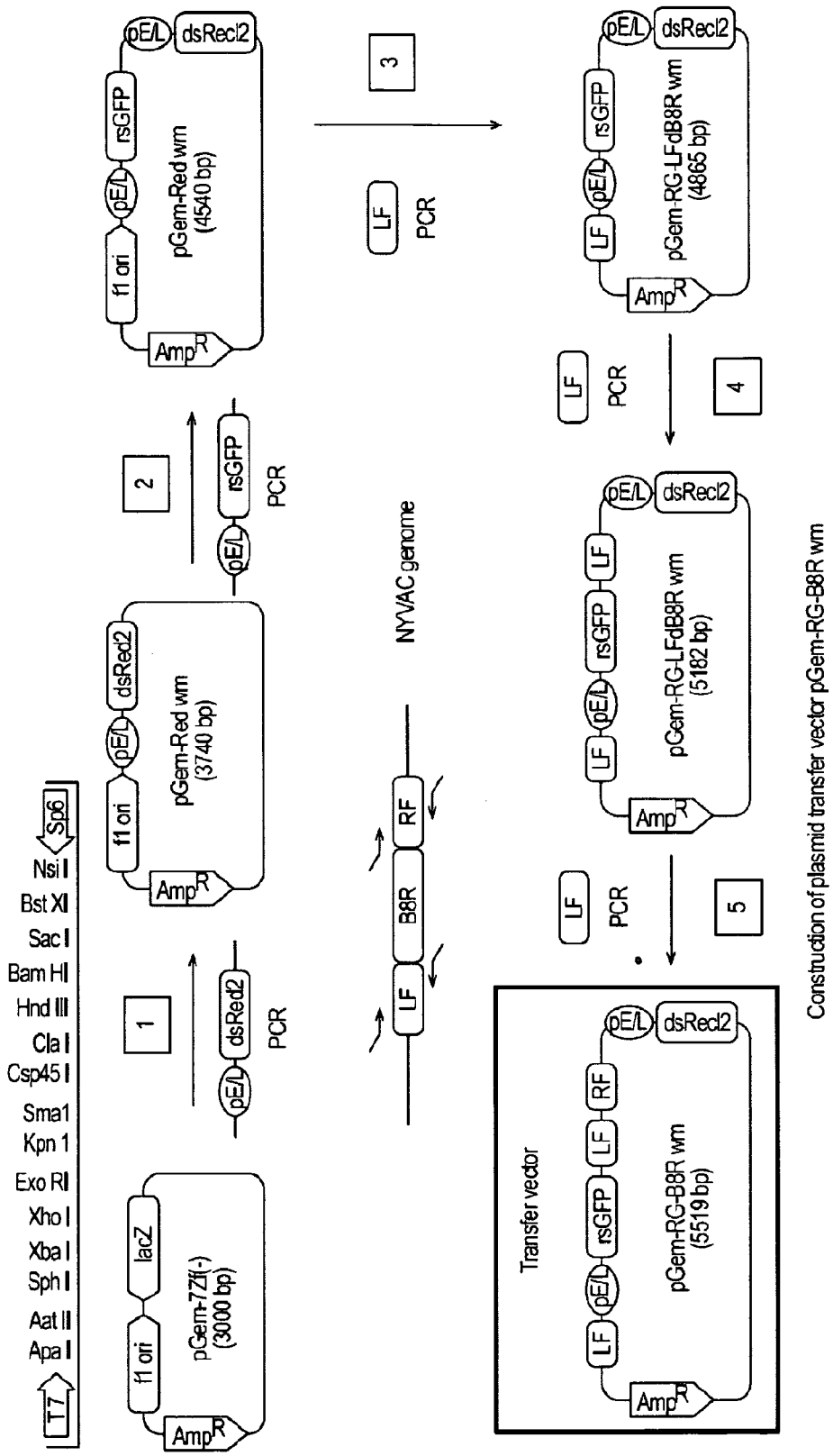
FIG. 3A. Construction of the plasmid transfer vector pGem-RG-B8R wm.
Figure 3B:
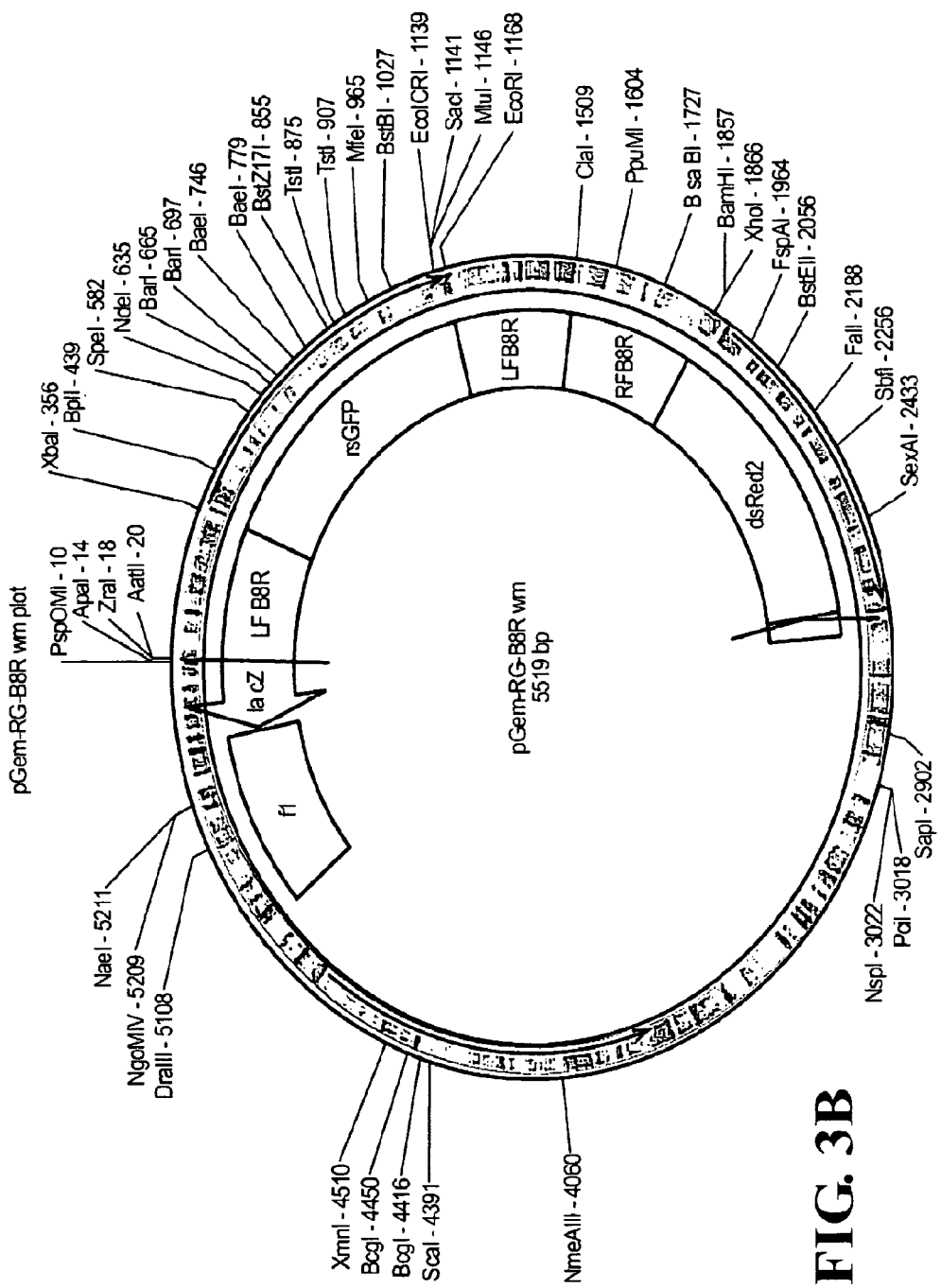
FIG. 3B. pGem-RG-B8R win plot.

NYVAC genome (FIG. 2) was used as the template to amplify the left flank of B8R gene (358 bp) with oligonucleotides LFB8R-AatII-F (5'-TTTTTT GACGTCATTGACTCGTCTACTATTC-3'; SEQ ID NO. 71) (Aat II site underlined) and LFB8R-XbaI-R (5'-TTTTTT TCTAGATGG TGTTGTTTGTTATTTG-3'; SEQ ID NO. 72) (Xba I site underlined). This left flank was digested with Aat II and Xba I and cloned into plasmid pGem-Red-GFP wm previously digested with the same restriction enzymes to generate pGem-RG-LFsB8R wm (4865 bp). The repeated left flank of B8R gene (358 bp) was amplified by PCR from NYVAC genome with oligonucleotides LFB8R'-EcoRI-F (5'-TTTTTTGAATTCATTGACTCGTCTACTATTC-3'; SEQ ID NO. 73) (Eco RI site underlined) and LFB8R'-ClaI-R (5'-TTTTTTATCGATTGGTGTTGT TTGTT-ATTTG-3'; SEQ ID NO. 74) (Cla I site underlined), digested with Eco RI and Cla I and inserted into the Eco RI/Cla I-digested pGem-RG-LFsB8R wm to generate pGem-RG-LFdB8R wm (5182 bp). The right flank of B8R gene (367 bp) was amplified by PCR from NYVAC genome with oligonucleotides RFB8R-ClaI-F (5'-TTTTTT ATCGATCTAATTT TTATTAATGATAC-3'; SEQ ID NO. 75) (Cla I site underlined) and RFB8R-BamHI-R (5'-TTTTTTGGATCCAAACAGCGGACACATTGC-3'; SEQ ID NO. 76) (Bam HI site underlined), digested with Cla I and Bam HI and inserted into the Cla I/Bam HI-digested pGem-RG-LFdB8R wm. The resulting plasmid pGem-RG-B8R wm (5519 bp; FIGS. 3A and 3B) was confirmed by DNA sequence analysis and directs the deletion of B8R gene from NYVAC-C genome.

This deletion mutant NYVAC-C-ΔB8R was constructed by transient dominant selection using dsRed2 and rsGFP genes as the transiently selectable markers. 3×10[6] BSC-40 cells were infected with 0.01 PFU/cell of NYVAC-C and transfected 1 h later with 6 µg DNA of plasmid pGem-RG-B8R wm using Lipofectamine (Invitrogen, San Diego, Calif.) according to the manufacturer's recommendations. After 48 h post-infection, the cells were harvested, lysed by freeze-thaw cycling, sonicated and used for recombinant virus screening. The deletion mutant was selected from progeny virus by consecutive rounds of plaque purification in BSC-40 cells during which plaques were screened for Red2/GFP fluorescence. In the first two passages, viruses from selected plaques expressed both fluorescent proteins, in the next two passages viral progeny from selected plaques expressed only one fluorescent marker (Red2 or GFP) and in the last two passages (six passages in total) viruses from selected plaques do not express any marker due to the loss of the fluorescent marker. The deletion mutant was detected by PCR amplifying the B8R locus.

The resulting NYVAC-C-ΔB8R positive virus plaques were grown in BSC-40 cells, and further passage twice in primary CEF cells. A P-2 stock was prepared in CEF and used for the propagation of the virus in CEF, followed by virus, purification through two 36% (w/v) sucrose cushions in 10 mM Tris-HCl pH 9, and titrated by plaque assay in BSC-40 cells. The purified grown stock of virus was referred as P-3.

To test the purity of the deletion mutant NYVAC-C-ΔB8R, viral DNA was extracted by the method of SDS-Proteinase K-Phenol from BSC-40 cells mock-infected or infected at 5 PFU/cell with NYVAC-C-ΔB8R. Primers LFB8R-AatII-F and LFB8R-BamHI-R spanning B8R flanking regions were used for PCR analysis of B8R locus. The amplification reactions were carried out with Platinum Taq DNA polymerase (Invitrogen, San Diego, Calif.) (results shown in FIG. 4).

Figure 5:
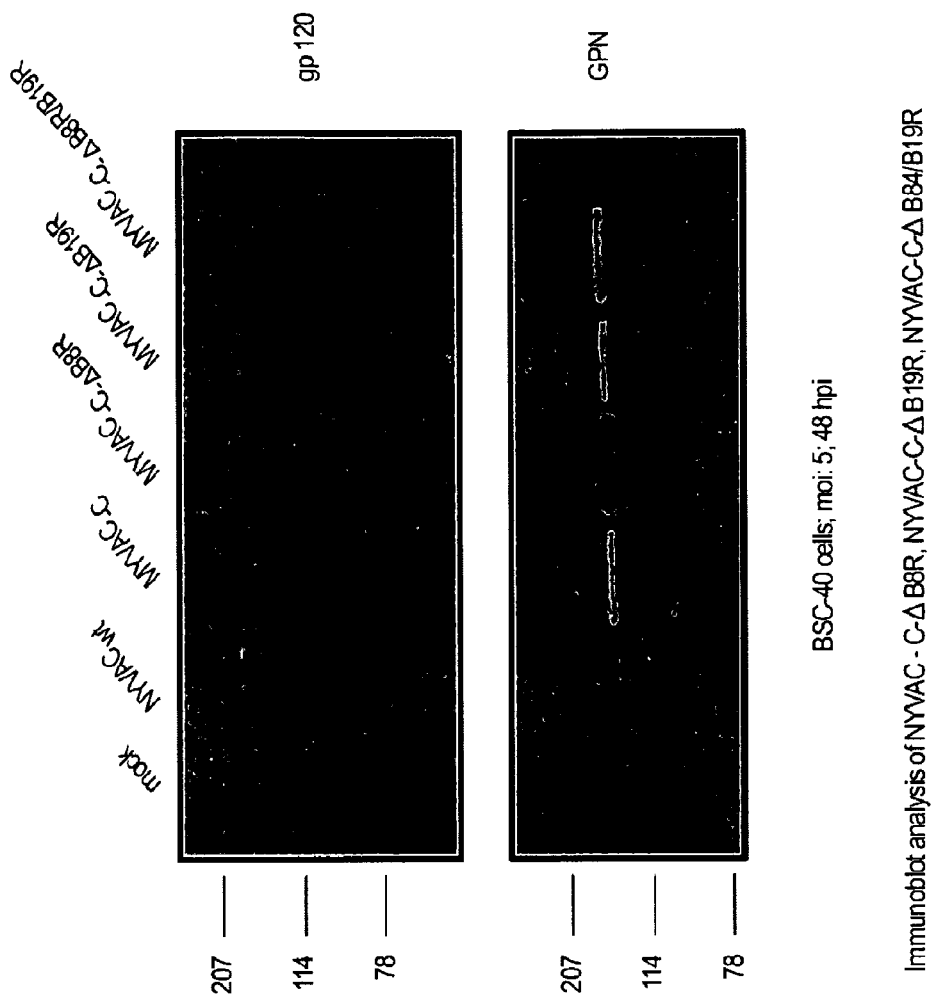
FIG. 5. Immunoblot analysis of NYVAC-C-ΔB8R, NYVAC-C-ΔB19R and NYVAC-C-ΔB8RB19R.

To test the correct expression of HIV proteins gp120 and GPN from NYVAC-C-ΔB8R, monolayers of BSC-40 cells were mock-infected or infected at 5 PFU/cell with NYVAC wt, NYVAC-C, NYVAC-C-ΔB8R. At 48 h post-infection, cells were lysed in Laemmli buffer, cells extracts fractionated by 8% SDS-PAGE and analyzed by Western blot using rabbit polyclonal anti-gp120 antibody (Centro Nacional de Biotecnologia; diluted 1:3000) or polyclonal anti-gag p24 serum (ARP 432, NIBSC, Centralised Facility for AIDS reagent, UK; diluted 1:1000) followed by anti-rabbit-HRP (Sigma; diluted 1:5000) to evaluate the expression of gp120 and GPN proteins (FIG. 5).

Figure 6:
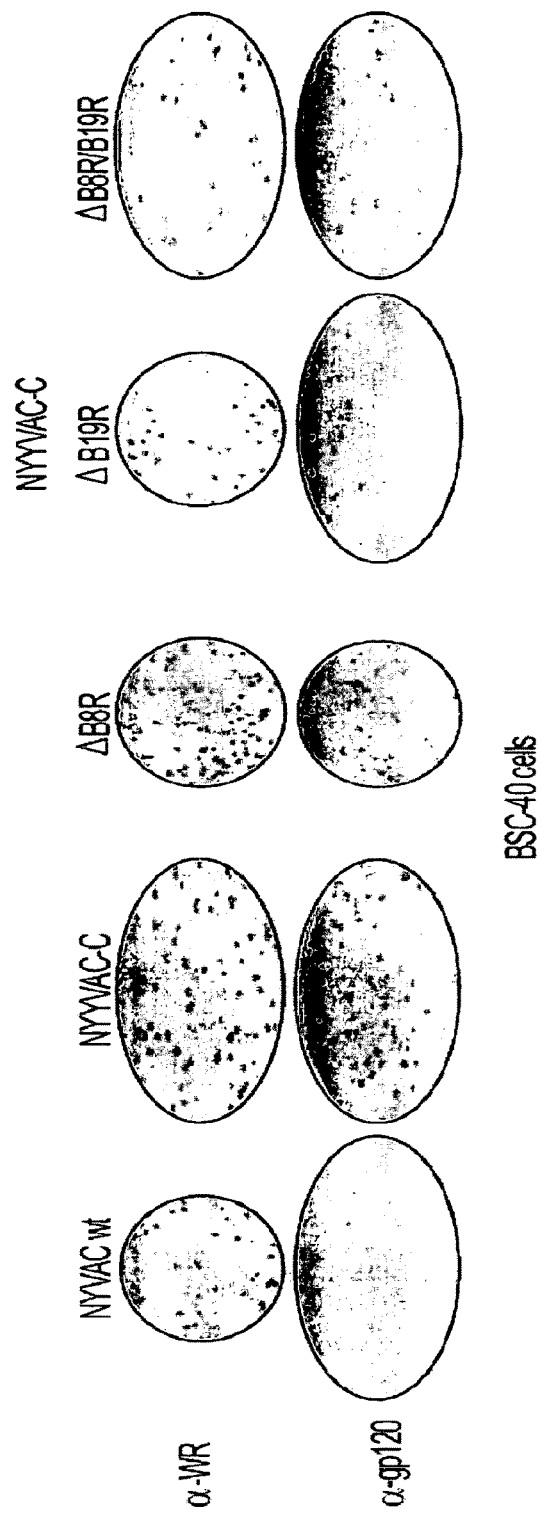
FIG. 6. Immunostain analysis of NYVAC-C-ΔB8R, NYVAC-C-ΔB19R and NYVAC-C-ΔB8RB19R.

To evaluate the stability of HIV proteins expressed by NYVAC-C-ΔB8R, monolayers of BSC-40 cells grown in 6 well-plates were infected with serial dilutions of NYVAC wt, NYVAC-C, NYVAC-C-ΔB8R produced after 12 successive passages. At 42 h post-infection, the viruses were titrated by plaque immunostaining assay using rabbit polyclonal antibody against vaccinia virus strain WR (Centro Nacional de Biotecnologia; diluted 1:1000) or rabbit polyclonal anti-gp120 antibody (Centro Nacional de Biotecnologia; diluted 1:250) followed by anti-rabbit-HRP (Sigma; diluted 1:1000) (FIG. 6). All recombinant viruses showed similar immunoreactivity to both anti-WR and anti-gp120.

Figure 7:
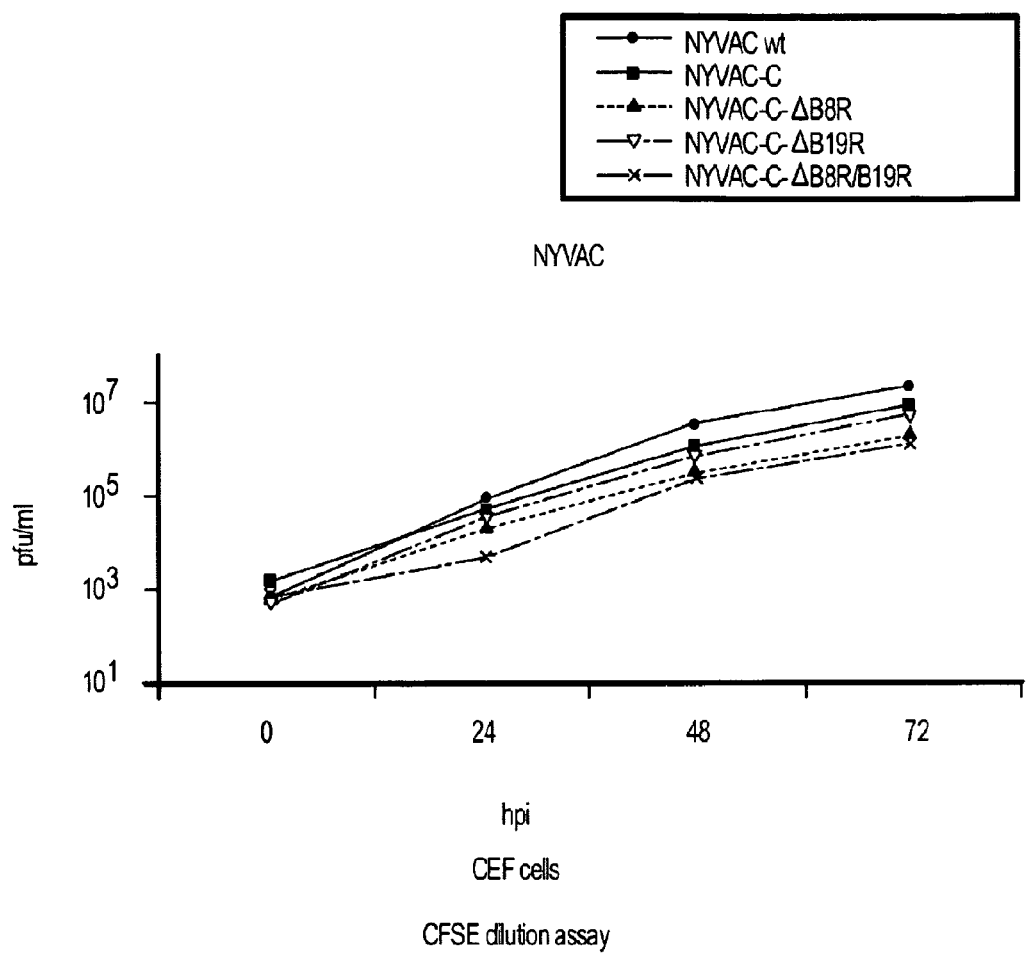
FIG. 7. Virus growth curves of NYVAC-C-ΔB8R, NYVAC-C-ΔB19R and NYVAC-C-ΔB8RB19R.

To determine virus-growth profiles, monolayers of CEF cells grown in 12-well tissue culture plates were infected in duplicate at 0.01 PFU/cell with NYVAC wt, NYVAC-C, NYVAC-C-ΔB8R. Following virus adsorption for 60 min at 37° C., the inoculum was removed. The infected cells were washed once with DMEM without serum and incubated with fresh DMEM containing 2% FCS at 37° C. in a 5% $CO_2$ atmosphere. At different times post-infection (0, 24, 48 and 72 hours), cells were removed by scraping (lysates at 5×10[5] cells/ml), freeze-thawed three times and briefly sonicated. Virus titers in cell lysates were determined by crystal violet staining in BSC-40 cells (FIG. 7).

2. NYVAC-C-ΔB19R Recombinant Vectors

Figure 8A:
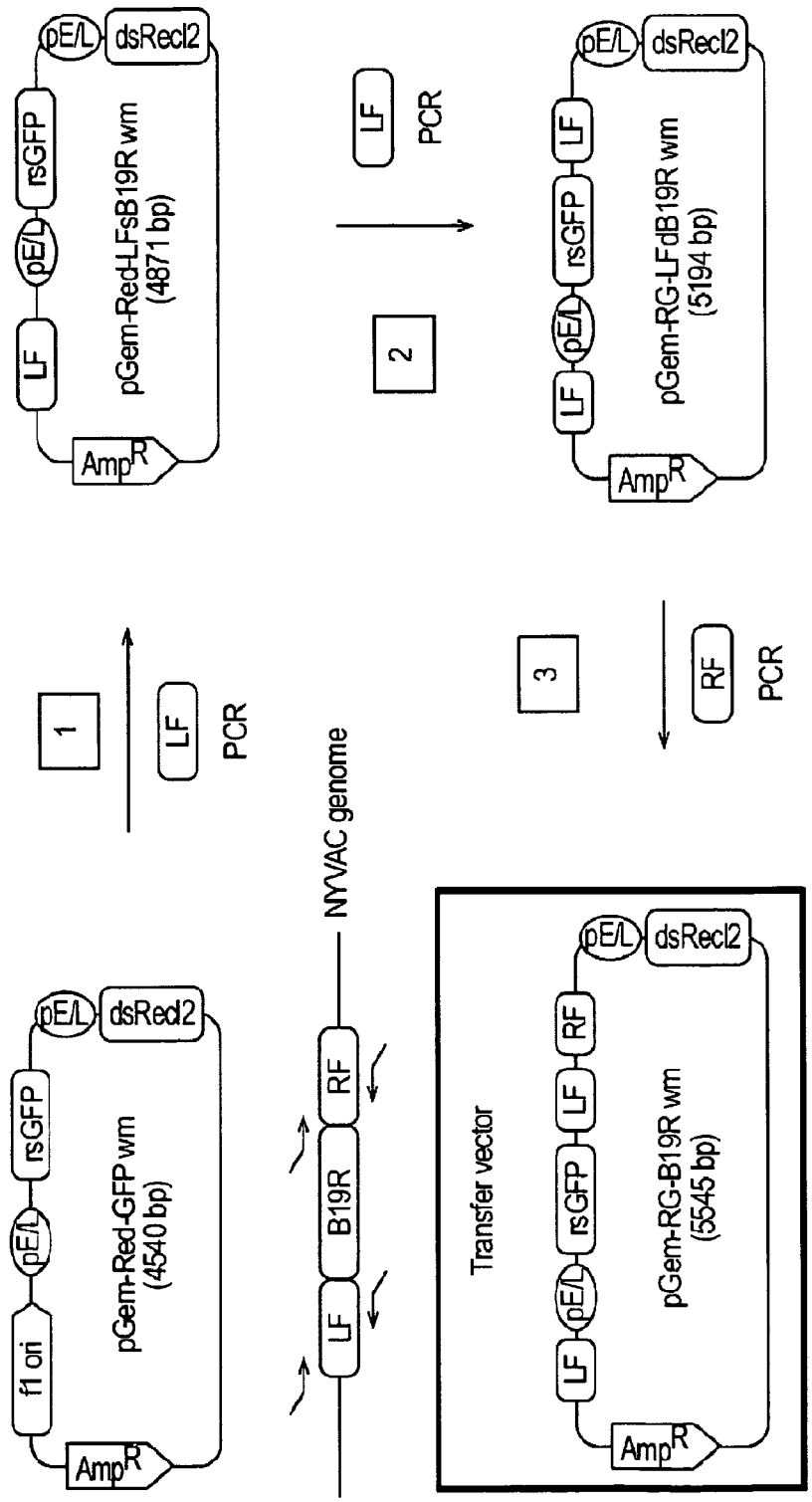
FIG. 8A. Construction of plasmid transfer vector pGem-RG-B19R wm.
Figure 8B:
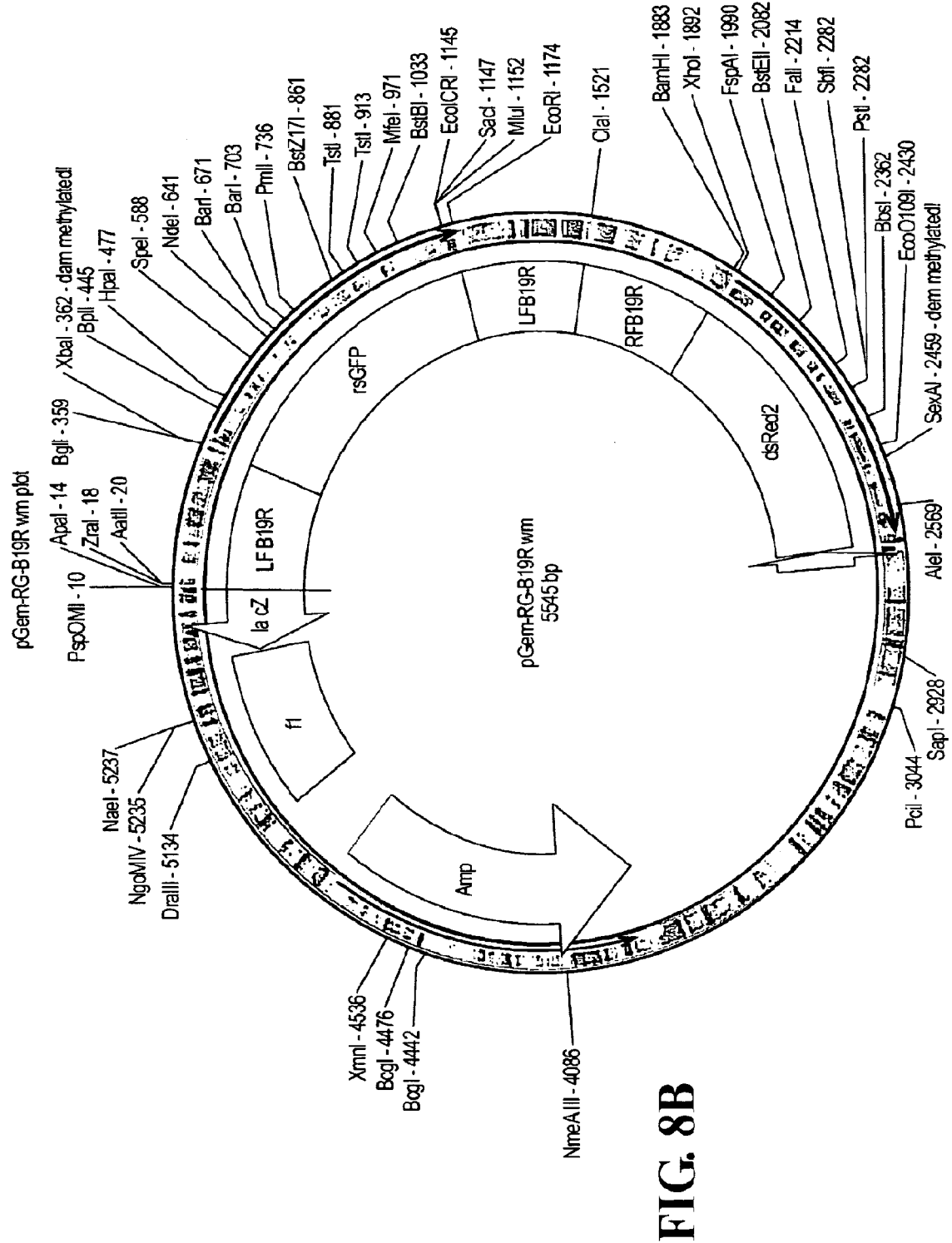
FIG. 8B. pGem-RG-B19R wm plot.

The plasmid transfer vector pGem-RG-B19R wm, used for the construction of the recombinant viruse "NYVAC-C-ΔB19R", having the B19R open reading frame (e.g, SEQ ID NO. 4 encoding SEQ ID NO. 3), was obtained by the sequential cloning of B19R recombination flanking sequences into the plasmid pGem-Red-GFP wm (previously described). NYVAC genome (FIG. 2) was used as the template to amplify the left flank of B19R gene (364 bp) with oligonucleotides LFB19R-AatII-F (5'-TTTTTT GACGTCGAGAAAGTTAAGAAGATAC-3'; SEQ ID NO. 77) (Aat II site underlined) and LFB19R-XbaI-R (5'-TTTTTTTCTAGATCTTTATTATACGGCACTAA-3'; SEQ ID NO. 78) (Xba I site underlined). This left flank was digested with Aat II and Xba I and cloned into plasmid pGem-Red-GFP wm previously digested with the same restriction enzymes to generate pGem-RG-LFsB19R wm (4871 bp). The repeated left flank of B19R gene (364 bp) was amplified by PCR from NYVAC genome with oligonucleotides LFB19R'-EcoRI-F (5'-TTTTTT GAATTCGAGAAAGTTAAGA AGATAC-3'; SEQ ID NO. 79) (Eco RI site underlined) and LFB19R'-ClaI-R (5'-TTTTTTATCGAT TCTTTATTATACGGCACTAA-3'; SEQ ID NO. 80) (Cla I site underlined), digested with Eco RI and Cla I and inserted into the Eco RI/Cla I-digested pGem-RG-LFsB19R wm to generate pGem-RG-LFdB19R wm (5194 bp). The right flank of B19R gene (381 bp) was amplified by PCR from NYVAC genome with oligonucleotides RFB19R-ClaI-F (5'-TTTTTTTATCGATATATACAAT GCATTTT-TATATAC-3'; SEQ ID NO. 81) (Cla I site underlined) and RFB19R-BamHI-R (5'-TTTTTTGGATCCAGTTCTA TCATAATCATC-3'; SEQ ID NO. 82) (Bam HI site underlined), digested with Cla I and Bam HI and inserted into the Cla I/Bam HI-digested pGem-RG-LFdB19R wm. The resulting plasmid pGem-RG-B19R wm (5545 bp; FIGS. 8A and 8B) was confirmed by DNA sequence analysis and directs the deletion of B19R gene from NYVAC-C genomes.

This deletion mutant NYVAC-C-ΔB19R was constructed by transient dominant selection using dsRed2 and rsGFP genes as the selectable markers. 3×10[6] BSC-40 cells were infected with 0.01 PFU/cell of NYVAC-C and transfected 1 h later with 6 µg DNA of plasmid pGem-RG-B19R wm using Lipofectamine (Invitrogen, San Diego, Calif.). After 48 h post-infection, the cells were harvested, lysed by freeze-thaw cycling, sonicated and used for recombinant virus screening. The deletion mutant was selected from progeny virus by consecutive rounds of plaque purification in BSC-40 cells during which plaques were screened for Red2/GFP fluorescence. In the first two passages, viruses from selected plaques expressed both fluorescent proteins. In the next two passages, viral progeny from selected plaques expressed only one fluorescent marker. In the last two passages, viruses from selected plaques do not express any marker due to the loss of the fluorescent marker. The deletion mutant was detected by PCR amplifying the B19R locus.

The resulting NYVAC-C-ΔB19R positive virus plaques were grown in BSC-40 cells, and further passage twice in primary CEF cells. A P-2 stock was prepared in CEF and used for the propagation of the virus in CEF, followed by virus purification through two 36% (w/v) sucrose cushions in 10 mM Tris-HCl pH 9, and titrated by plaque assay in BSC-40 cells. The purified grown stock of virus was referred as P-3.

To test the purity of the deletion mutant NYVAC-C-ΔB19R, viral DNA was extracted by the method of SDS-Proteinase K-Phenol from BSC-40 cells mock-infected or infected at 5 PFU/cell with NYVAC-C-ΔB19R. Primers LFB19R-AatII-F and LFB19R-Bam-R spanning B19R flanking regions were used for PCR analysis of B19R locus. The amplification reactions were carried out with Platinum Taq DNA polymerase (Invitrogen, San Diego, Calif.) (FIG. 4).

To test the correct expression of HIV proteins gp120 and GPN from NYVAC-C-ΔB19R, monolayers of BSC-40 cells were mock-infected or infected at 5 PFU/cell with NYVAC wt, NYVAC-C, NYVAC-C-ΔB19R. At 48 h post-infection, cells were lysed in Laemmli buffer, cells extracts fractionated by 8% SDS-PAGE and analyzed by Western blot using rabbit polyclonal anti-gp120 antibody (Centro Nacional de Biotecnologia; diluted 1:3000) or polyclonal anti-gag p24 serum (ARP 432, NIBSC, Centralised Facility for AIDS reagent, UK; diluted 1:1000) followed by anti-rabbit-HRP (Sigma; diluted 1:5000) to evaluate the expression of gp120 and GPN proteins (FIG. 5).

To evaluate the stability of HIV proteins expressed by NYVAC-C-ΔB19R, monolayers of BSC-40 cells grown in 6 well-plates were infected with serial dilutions of NYVAC wt, NYVAC-C, NYVAC-C-ΔB19R produced after 12 successive passages. At 42 h post-infection, the viruses were titrated by plaque immunostaining assay using rabbit polyclonal antibody against vaccinia virus strain WR (Centro Nacional de Biotecnologia; diluted 1:1000) or rabbit polyclonal anti-gp120 antibody (Centro Nacional de Biotecnologia; diluted 1:250) followed by anti-rabbit-HRP (Sigma; diluted 1:1000) (FIG. 6). All recombinant viruses showed similar immunoreactivity to both anti-WR and anti-gp120.

To determine virus-growth profiles, monolayers of CEF cells grown in 12-well tissue culture plates were infected in duplicate at 0.01 PFU/cell with NYVAC wt, NYVAC-C, NYVAC-C-ΔB19R. Following virus adsorption for 60 min at 37° C., the inoculum was removed. The infected cells were washed once with DMEM without serum and incubated with fresh DMEM containing 2% FCS at 37° C. in a 5% $CO_2$ atmosphere. At different times post-infection (0, 24, 48 and 72 hours), cells were removed by scraping (lysates at $5 \times 10^5$ cells/ml), freeze-thawed three times and briefly sonicated. Virus titers in cell lysates were determined by crystal violet staining in BSC-40 cells (FIG. 7).

4. NYVAC-C-ΔB8R/B19R Recombinant Vectors

The plasmid transfer vector pGem-RG-B19R wm, used for the construction of the recombinant virus "NYVAC-C-ΔB8R/B19R", having the B8R open reading frame (e.g, SEQ ID NO. 2 encoding SEQ ID NO. 1) and the B19R open reading frame (e.g, SEQ ID NO. 4 encoding SEQ ID NO. 3) deleted from the NYVAC genome, was obtained by the sequential cloning of B19R recombination flanking sequences into the plasmid pGem-Red-GFP wm (previously described). NYVAC genome (FIG. 2) was used as the template to amplify the left flank of B19R gene (364 bp) with oligonucleotides LFB19R-AatII-F (5'-TTTTTTGACGTCGAGAAAGTTAAGAAGATAC-3'; SEQ ID NO. 77) (Aat II site underlined) and LFB19R-XbaI-R (5'-TTTTTTCTAGATCTTTATTATACGGCACTAA-3'; SEQ ID NO. 78) (Xba I site underlined). This left flank was digested with Aat II and Xba I and cloned into plasmid pGem-Red-GFP wm previously digested with the same restriction enzymes to generate pGem-RG-LFsB19R wm (4871 bp). The repeated left flank of B19R gene (364 bp) was amplified by PCR from NYVAC genome with oligonucleotides LFB19R'-EcoRI-F (5'-TTTTTTGAATTCGAGAAAGTTAAGAAGATAC-3'; SEQ ID NO. 79) (Eco RI site underlined) and LFB19R'-ClaI-R (5'-TTTTTTATCGAT TCTTATTATACGGCACTAA-3'; SEQ ID NO. 80) (Cla I site underlined), digested with Eco RI and Cla I and inserted into the Eco RI/Cla I-digested pGem-RG-LFsB19R wm to generate pGem-RG-LFdB19R wm (5194 bp). The right flank of B19R gene (381 bp) was amplified by PCR from NYVAC genome with oligonucleotides RFB19R-ClaI-F (5'-TTTTTTATCGATATATACAATG CATTTT-TATATAC-3') (Cla I site underlined; SEQ ID NO. 81) and RFB19R-BamHI-R (5'-TTTTTTGGATCCAGTTCTA TCATAATCATC-3'; SEQ ID NO. 82) (Bam HI site underlined), digested with Cla I and Bam HI and inserted into the Cla I/Bam HI-digested pGem-RG-LFdB19R wm. The resulting plasmid pGem-RG-B19R wm (5545 bp; FIG. 8A and FIG. 8B) was confirmed by DNA sequence analysis and directs the deletion of B19R gene from NYVAC-C-ΔB8R genomes.

This deletion mutant, NYVAC-C-ΔB8R/B19R, was constructed by transient dominant selection using dsRed2 and rsGFP genes as the selectable markers. $3 \times 10^6$ BSC-40 cells were infected with 0.01 PFU/cell of NYVAC-C-ΔB8R and transfected 1 h later with 6 μg DNA of plasmid pGem-RG-B19R wm using Lipofectamine (Invitrogen, San Diego, Calif.). After 48 h post-infection, the cells were harvested, lysed by freeze-thaw cycling, sonicated and used for recombinant virus screening. Deletion mutant was selected from progeny virus by consecutive rounds of plaque purification in BSC-40 cells during which plaques were screened for Red2/GFP fluorescence. In the first two passages viruses from selected plaques expressed both fluorescent proteins. In the next two passages, viral progeny from selected plaques expressed only one fluorescent marker. In the last two passages, viruses from selected plaques do not express any marker due to the loss of the fluorescent marker. The deletion mutant was detected by PCR amplifying the B19R locus.

The resulting NYVAC-C-ΔB8P/B19R positive virus plaques were grown in BSC-40 cells, and further passaged twice in primary CEF cells. A P-2 stock was prepared in CEF and used for the propagation of the virus in CEF, followed by virus purification through two 36% (w/v) sucrose cushions in 10 mM Tris-HCl pH 9, and titrated by plaque assay in BSC-40 cells. The purified grown stock of virus was referred as P-3.

To test the purity of the deletion mutant NYVAC-C-ΔB8P/B19R, viral DNA was extracted by the method of SDS-Proteinase K-Phenol from BSC-40 cells mock-infected or infected at 5 PFU/cell with NYVAC-C-ΔB8P/B19R. Primers LFB8R-AatII-F and LFB8R-BamHI-R spanning B8R flanking regions were used for PCR analysis of B8R locus. Primers LFB19R-AatII-F and LFB19R-BamHI-R spanning B19R flanking regions were used for PCR analysis of B19R locus The amplification reactions were carried out with Platinum Taq DNA polymerase (Invitrogen, San Diego, Calif.) (FIG. 4).

To test the correct expression of HIV proteins gp120 and GPN from NYVAC-C-ΔB8R/B19R, monolayers of BSC-40 cells were mock-infected or infected at 5 PFU/cell with NYVAC wt, NYVAC-C, NYVAC-C-ΔB8P/B19R. At 48 h post-infection, cells were lysed in Laemmli buffer, cells extracts fractionated by 8% SDS-PAGE and analyzed by Western blot using rabbit polyclonal anti-gp120 antibody (Centro Nacional de Biotecnologia; diluted 1:3000) or polyclonal anti-gag p24 serum (ARP 432, NIBSC, Centralised Facility for AIDS reagent, UK; diluted 1:1000) followed by anti-rabbit-HRP (Sigma; diluted 1:5000) to evaluate the expression of gp120 and GPN proteins (FIG. 5).

To evaluate the stability of HIV proteins expressed by NYVAC-C-ΔB8R/B19R, monolayers of BSC-40 cells grown in 6 well-plates were infected with serial dilutions of NYVAC wt, NYVAC-C, NYVAC-C-ΔB8R/B19R produced after 12 successive passages. At 42 h post-infection, the viruses were titrated by plaque immunostaining assay using rabbit polyclonal antibody against vaccinia virus strain WR (Centro Nacional de Biotecnologia; diluted 1:1000) or rabbit polyclonal anti-gp120 antibody (Centro Nacional de Biotecnologia; diluted 1:250) followed by anti-rabbit-HRP (Sigma; diluted 1:1000) (FIG. 6). All recombinant viruses showed similar immunoreactivity to both anti-WR and anti-gp120.

To determine virus-growth profiles, monolayers of CEF cells grown in 12-well tissue culture plates were infected in duplicate at 0.01 PFU/cell with NYVAC wt, NYVAC-C, NYVAC-C-ΔB8R/B19R. Following virus adsorption for 60 min at 37° C., the inoculum was removed. The infected cells were washed once with DMEM without serum and incubated with fresh DMEM containing 2% FCS at 37° C. in a 5% $CO_2$ atmosphere. At different times post-infection (0, 24, 48 and 72 hours), cells were removed by scraping (lysates at $5 \times 10^5$ cells/ml), freeze-thawed three times and briefly sonicated. Virus titers in cell lysates were determined by crystal violet staining in BSC-40 cells (FIG. 7).

B. Replication Competent NYVAC

The development of attenuated, replication competent strains of vaccinia virus that induce a potent immune response is described below. It is known in the art that replication-defective strains of vaccinia virus often do not induce a sufficiently potent immune response to be therapeutically useful. This may be due to the limitation in replication and the failure of most strains of vaccinia virus to induce pro-inflammatory signal transduction and pro-inflammatory gene expression. The recombinant vectors described herein have been developed to provide a solution to these problems. As shown below, replication-competent, attenuated strains of vaccinia virus induce potent pro-inflammatory signal transduction and pro-inflammatory gene expression.

1. NYVAC-C-KC and NYVAC-C+12 Recombinant Vectors

During construction of NYVAC, a non-essential region of the vaccinia virus genome containing twelve genes flanked by the K1L and C7L host range genes was deleted. Deletion of genes in this region renders NYVAC replication-defective in human cells. As shown below, replication competence of NYVAC was restored by re-insertion of the two host range genes C7L and K1L into NYVAC (NYVAC-KC) or NYVAC-C (NYVAC-C-KC), or re-insertion of the entire host range region (C1L (e.g., SEQ ID NOS. 5, 6), C2L (e.g., SEQ ID NOS. 7, 8), C3L (e.g., SEQ ID NOS. 9, 10), C4L (SEQ ID NOS. 11, 12), C5L (e.g., SEQ ID NOS. 13, 14), C6L (e.g., SEQ ID NOS. 15, 16), C7L (e.g., SEQ ID NOS. 17, 18), N1L (SEQ ID NOS. 19, 20), N2L (e.g., SEQ ID NOS. 21, 22), M1L (e.g., SEQ ID NOS. 23, 24), M2L (e.g., SEQ ID NOS. 25, 26), and K1L (e.g., SEQ ID NOS. 27, 28)) into NYVAC (NYVAC+12) or NYVAC-C (NYVAC-C+12). The NYVAC-KC, NYVAC-C-KC, NYVAC+12, and NYVAC-C+12 have other attenuating deletions (present in the "wild-type" NYVAC and NYVAC-C vectors), and thus remain relatively attenuated despite being replication competent.

Figure 9:
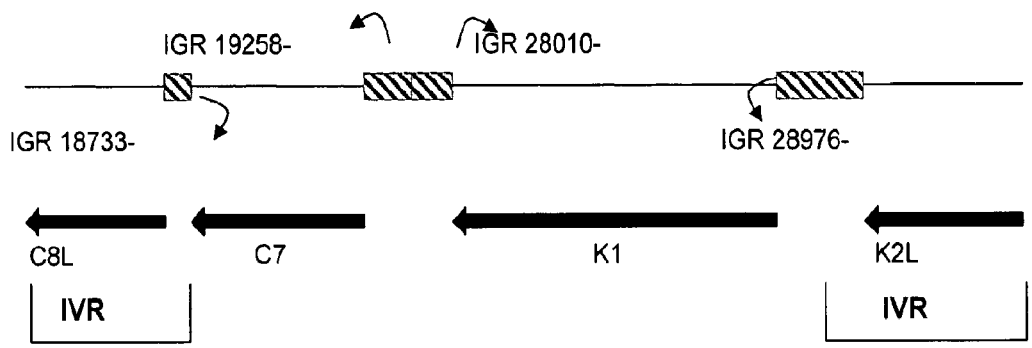
FIG. 9. Methodology used to construct KC viruses. To create a single fragment containing K1L and C7L, the two genes were first amplified by PCR from the wild type vaccinia virus genome, Copenhagen strain. PCR was used to fuse the two fragments into one. In vivo recombination (IVR) was used to insert the final PCR product between the existing inter-genic regions of the genome, creating NYVAC. In vivo combination was also used to create NYVAC-C-KC-ΔB8R-ΔB19R, using NYVAC-C-ΔB8R-ΔB19R as the parental virus.

To produce NYVAC-KC, the C7L and K1L genes from the Copenhagen strain of vaccinia virus were inserted back into the genome of either NYVAC or NYVAC-C. Each gene, plus a corresponding portion of the flanking regions, was amplified by PCR. The two fragments were combined into one fragment using PCR. The entire cassette containing both genes and flanking regions homologous to the adjacent genes of the NYVAC genome was inserted into NYVAC-C by in vivo recombination. Recombinants were selected by growth on RK-13 cells. The resulting viruses are called "NYVAC-KC" and "NYVAC-C-KC", respectively (FIG. 9).

Figure 10:
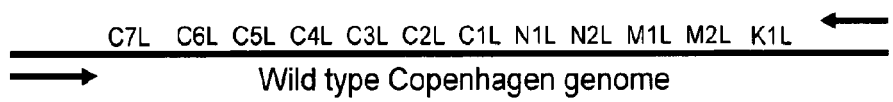
FIG. 10. Methodology used to construct NYVAC-C+12 virus.

To produce the recombinant vector "NYVAC+12" and "NYVAC-C+12", C1L (e.g., SEQ ID NOS. 5, 6), C2L (e.g., SEQ ID NOS. 7, 8), C3L (e.g., SEQ ID NOS. 9, 10), C4L (SEQ ID NOS. 11, 12), C5L (e.g., SEQ ID NOS. 13, 14), C6L (e.g., SEQ ID NOS. 15, 16), C7L (e.g., SEQ ID NOS. 17, 18), N1L (SEQ ID NOS. 19, 20), N2L (e.g., SEQ ID NOS. 21, 22), M1L (e.g., SEQ ID NOS. 23, 24), M2L (e.g., SEQ ID NOS. 25, 26), and K1L (e.g., SEQ ID NOS. 27, 28), which span the region from C7L to K1L of the Copenhagen strain of vaccinia virus (FIG. 2) were inserted (e.g., incorporated) back into genome of either NYVAC or NYVAC-C, respectively (FIG. 10). The entire cassette of genes, with sequences flanking K1L and C7L, was prepared by long-range PCR. The entire cassette was inserted into NYVAC or NYVAC-C by in vivo recombination. Recombinants were selected by growth on RK-13 cells.

The K1L (e.g, SEQ ID NO. 28 encoding SEQ ID NO. 27) and C7L (e.g, SEQ ID NO. 18 encoding SEQ ID NO. 17) genes of VACV Copenhagen were re-inserted into NYVAC-ΔB8R/ΔB19R and NYVAC-C-ΔB8R/ΔB19R, as described above, to yield the viruses "NYVAC-KC-ΔB8R/ΔB19R" and "NYVAC-C-KC-ΔB8R/ΔB19R", respectively. RK-13 cells were co-infected with "NYVAC-C+12-ATVh" (see below) and NYVAC-C-ΔB8R/ΔB19R, or the corresponding viruses lacking HIV genes (e.g., NYVAC-KC-ΔB8R/ΔB19R and NYVAC+12-ATVh), to screen for recombinant viruses containing an intact host range region. Individual plaques were screened by PCR to identify recombinants containing ATV and lacking B8R and B19R.

2. NYVAC-C-KC-ATVh and NYVAC-C+12-ATVh Recombinant Vectors

Double-stranded RNA (dsRNA) is a potent inducer of signalling through stress related signalling pathways, such as TRL3/RIG1 and the p38 MAP kinase pathway. Signalling through these pathways leads to activation of pro-inflammatory transcription factors ATF-2, NF-κB and IRF-3. Vaccinia virus blocks signalling by dsRNA by encoding a dsRNA-binding protein (the product of the E3L gene) that sequesters dsRNA and prevents signalling leading to activation of the pro-inflammatory transcription factors IRF-3, NF-κB; and ATF-2. Vaccinia virus lacking E3L (VVΔE3L) induces signalling that leads to activation of these three pro-inflammatory transcription factors. This induces pro-inflammatory gene expression and induces a potent Th1 dominated immune response in mice, despite replicating to three logs lower titer than wild-type vaccinia (wtVV). However, utility of VVΔE3L is limited by activation of RNA-dependent protein kinase (PKR) by dsRNA in infected cells. Activation of PKR in cells infected with VVΔE3L leads to a rapid inhibition of viral protein synthesis, limiting gene expression to the first four hours of infection.

Figure 11:
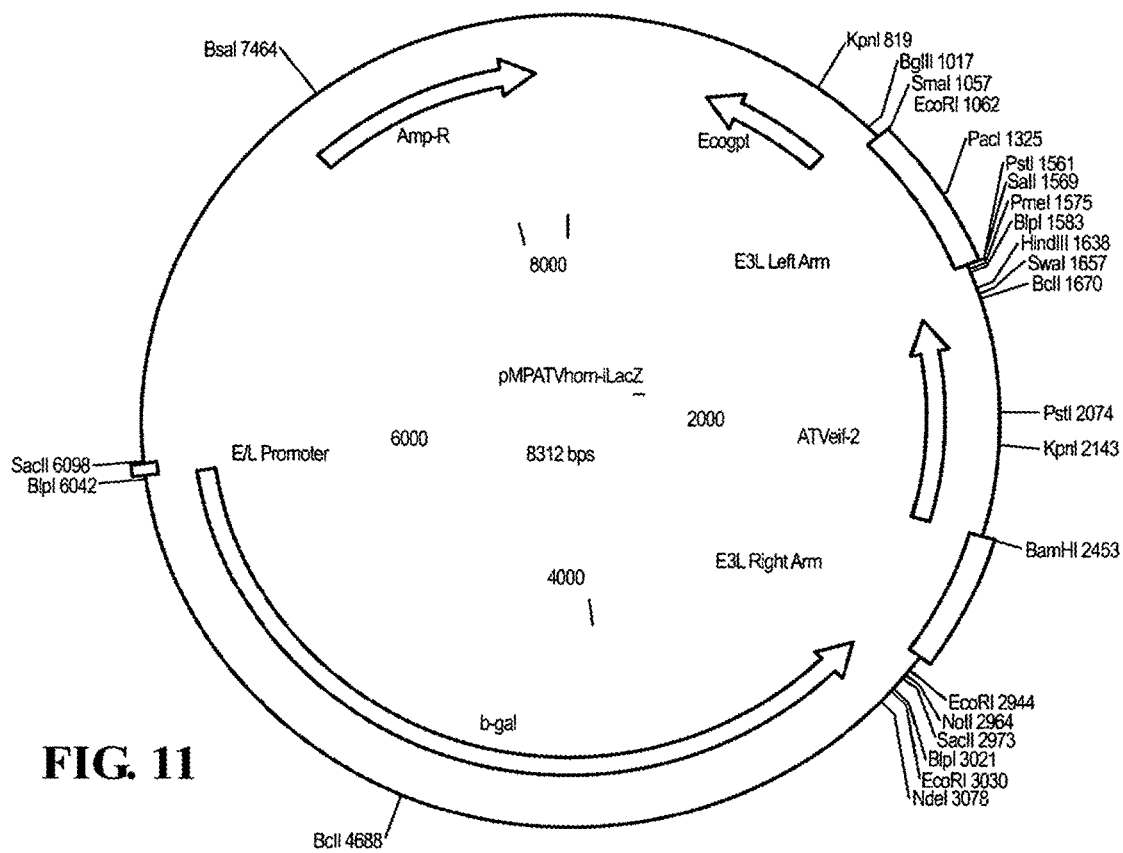
FIG. 11. Methodology used to construct NYVAC-C+12-ATVh virus. The E3L gene of NYVAC was replaced with the eIF2α homologue from Ambystoma tigrinum virus (ATVh) by in vivo recombination (IVR) to create NYVAC-C+12-ATVh. The ATVh had been amplified by PCR, with flanking region sequences at either end of the gene to allow for recombination, and inserted into a transfer plasmid. The plasmid was used in the IVR to transfer the ATVh into the virus genome.
Figure 12A:
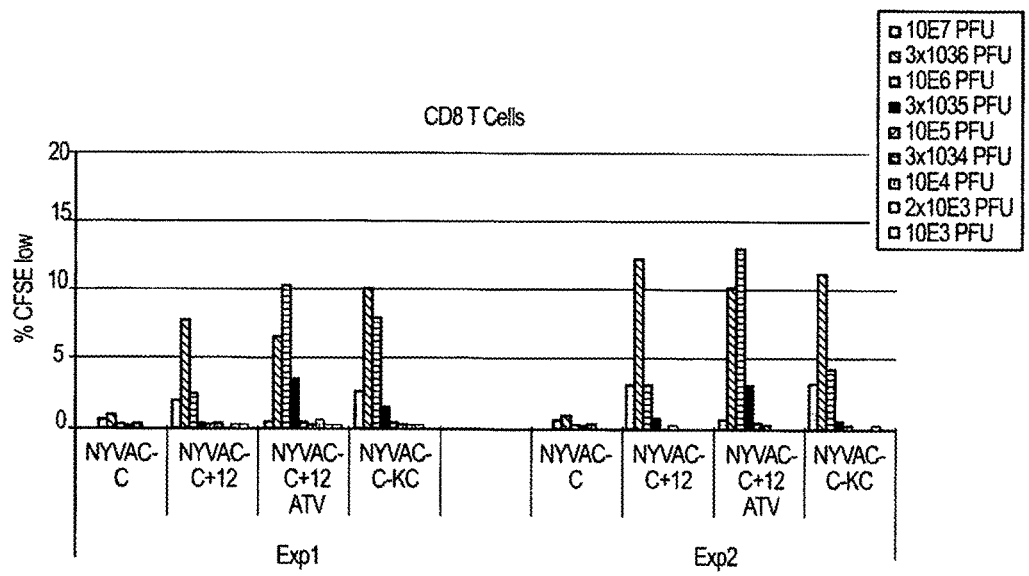
FIGS. 12A and 12B. Flow cytometric analysis.
Figure 12B:
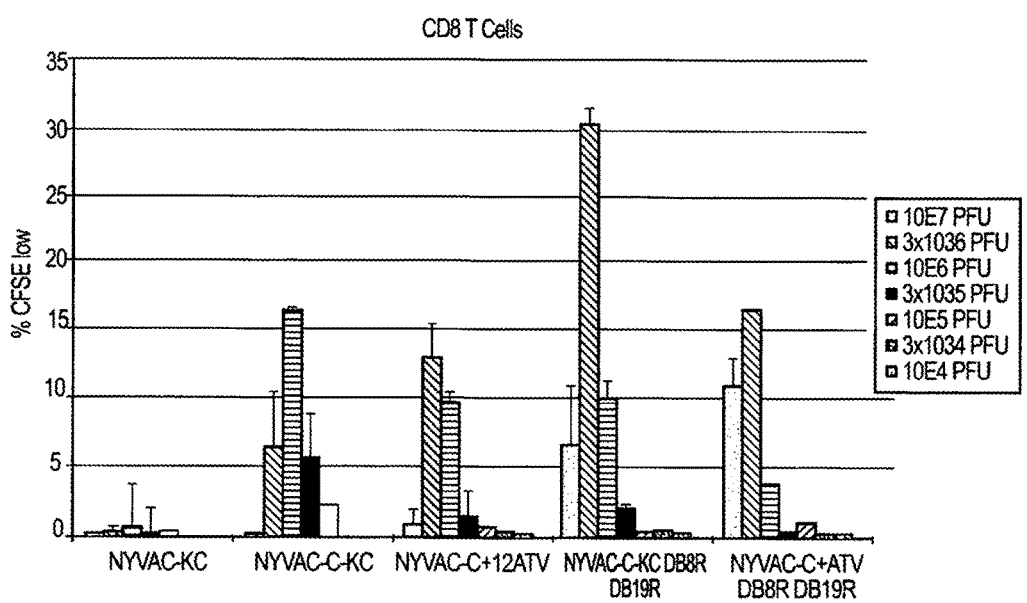
Figure 13A:
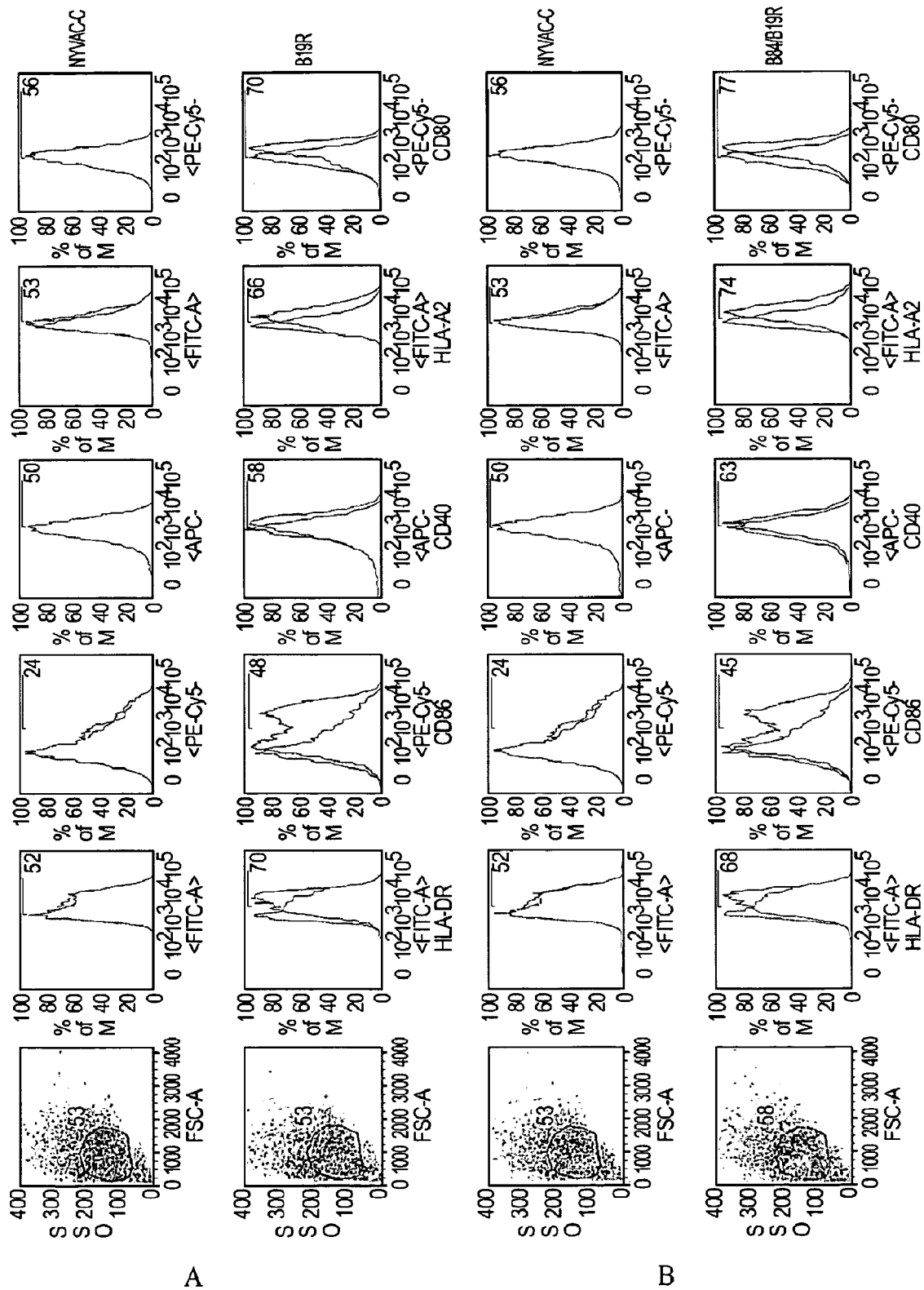
FIG. 13A. Upregulation of costimulatory molecules on infected human moDCs. IL-4 and GM-CSF differentiated DC were infected with NYVAC-C and the deletion mutants B19R (A) and B8R/B19R (B) expression of costimulatory molecules was analyzed by FACS analysis 48 hr post infection. DCs were infected with an MOI of 0.1. The shaded peaks in the histograms represent NYVAC-wt infected DC; the unshaded peaks represent DC infected with NYVAC-C, B19R or B8R/B19R.
Figure 13B:
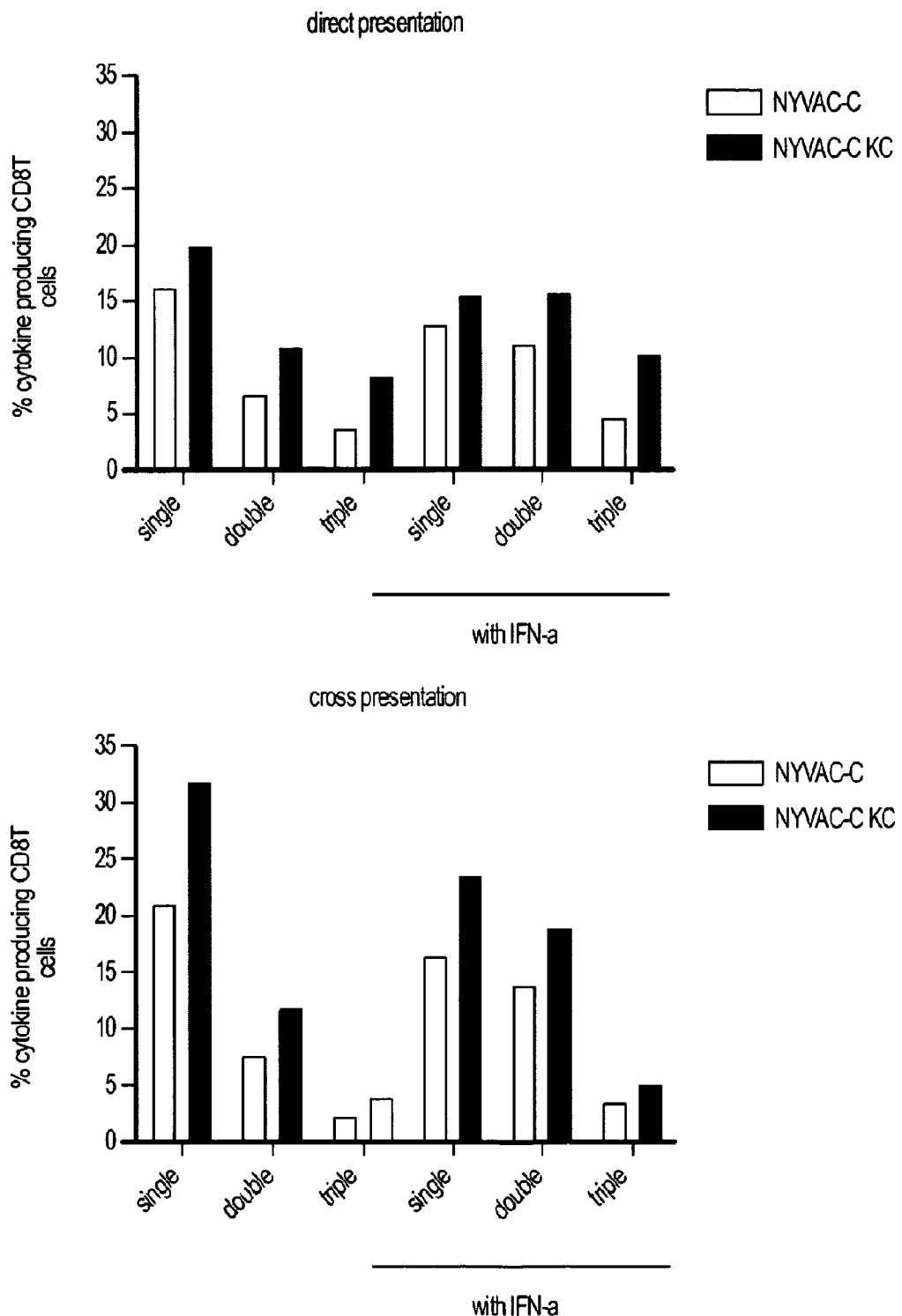
FIG. 13B. Cytokine production by HIV specific CD8 T cells in a direct and cross presentation assay. DCs were infected or incubated with apoptotic infected HeLa cells for 6 hrs before CD8 T cells were added. After overnight incubation the amount of single, double and triple cytokine producing cells was determined by FACS analysis.
Figure 14A:
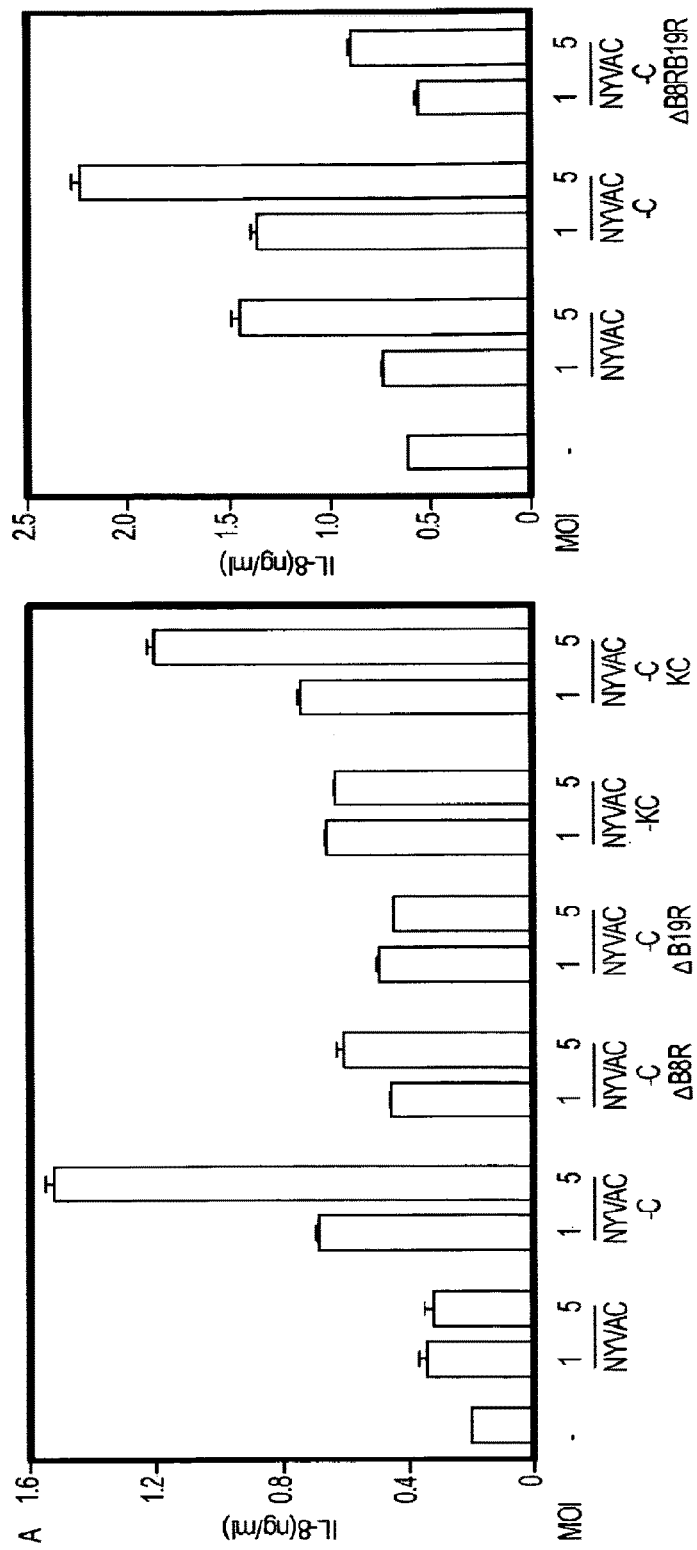
FIG. 14. IL-8 production assays. IL-8 and TNF release by human THP-1 macrophages (A) and whole blood (B) infected with wild-type and mutant NYVAC and NYVAC-C.
Figure 14B:
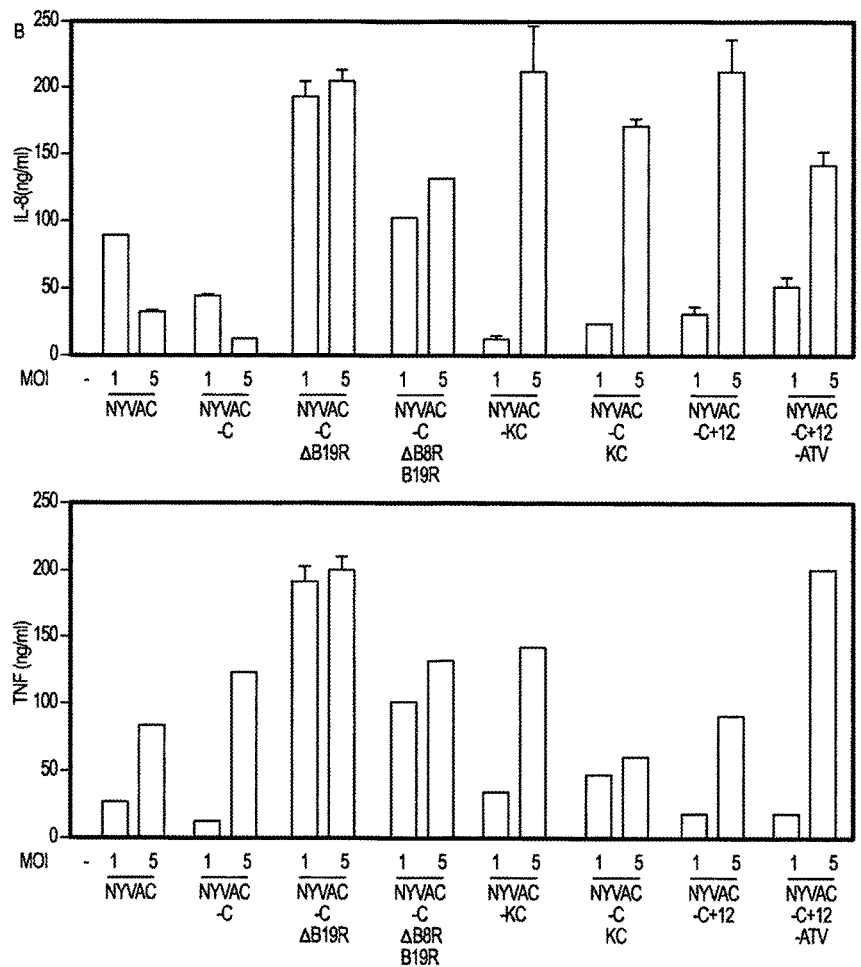

To overcome this deficit, recombinant vectors have been developed that replace the E3L gene in vaccinia with the ATV eIF2αH (SEQ ID NO. 29, 30) which is known to be a potent, non-dsRNA-binding inhibitor of PKR. The eIF2αH gene from ATV (Accession No. EU51233.1) (e.g., SEQ ID NO. 30) was cloned between the BamH1 and BclI sites in the pre-existing transfer plasmid pMPE3ΔGPTMCS (Kibler et al. 1997. Double-stranded RNA is a trigger for apoptosis in vaccinia virus-infected cells. J Virol 71:1992-2003). A map of the resulting plasmid, called pMPATVhom, is shown in FIG. 11. Transient dominant selection (mycophenolic acid resistance) was used to replace the E3L gene in NYVAC+12 and NYVAC-C+12 with the ATV eIF2αH gene (producing "NYVAC+12-ATVh" and "NYVAC-C+12-ATVh"). Correct insertion was confirmed by PCR.

Figure 15A:
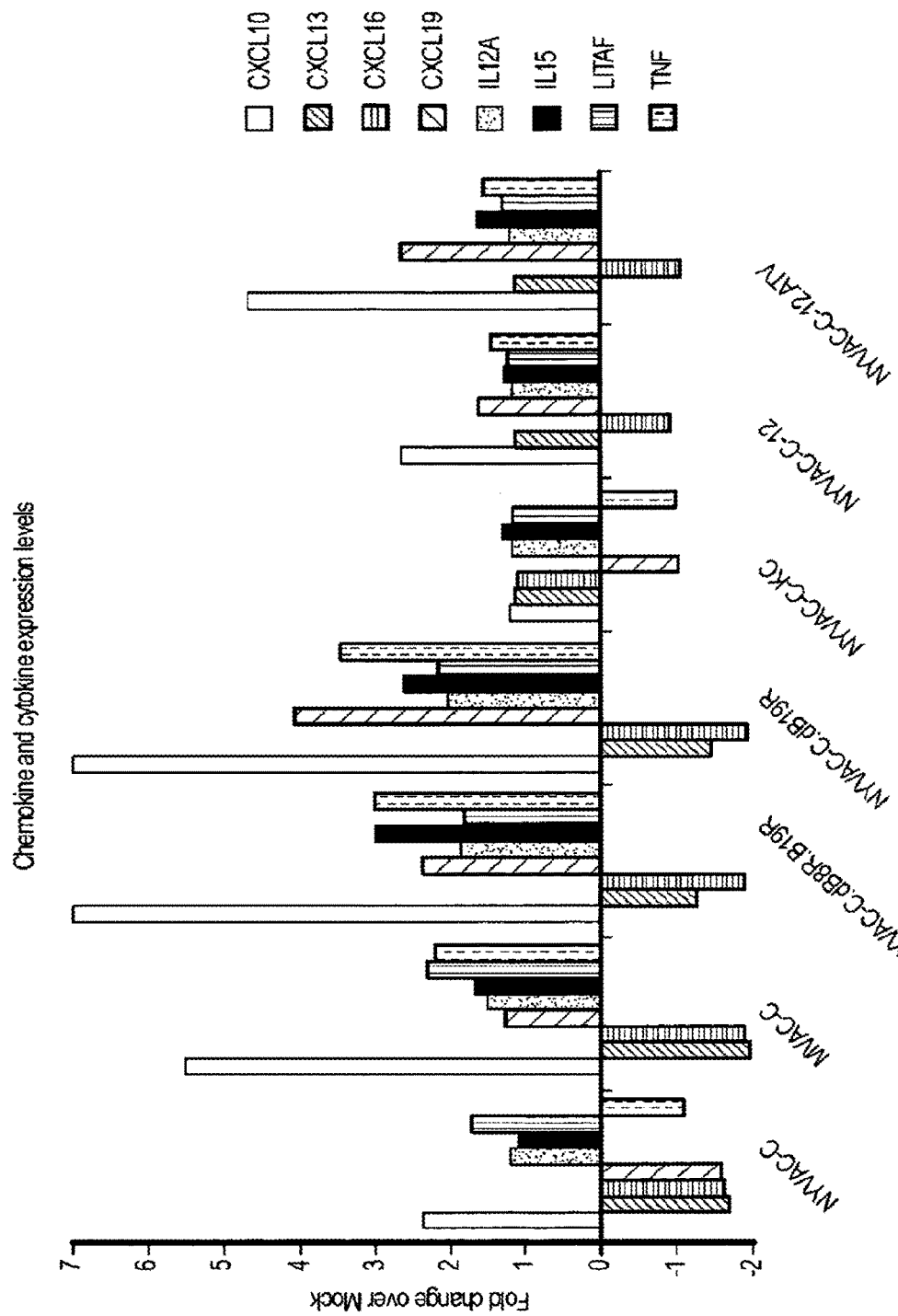
FIG. 15. Gene array assays. A. chemokine and cytokine expression levels; B. IFN expression levels; C. Enhanced expression of pathogen sensing molecules; D. Enhanced expression in genes associated with inflammatory response.
Figure 15B:
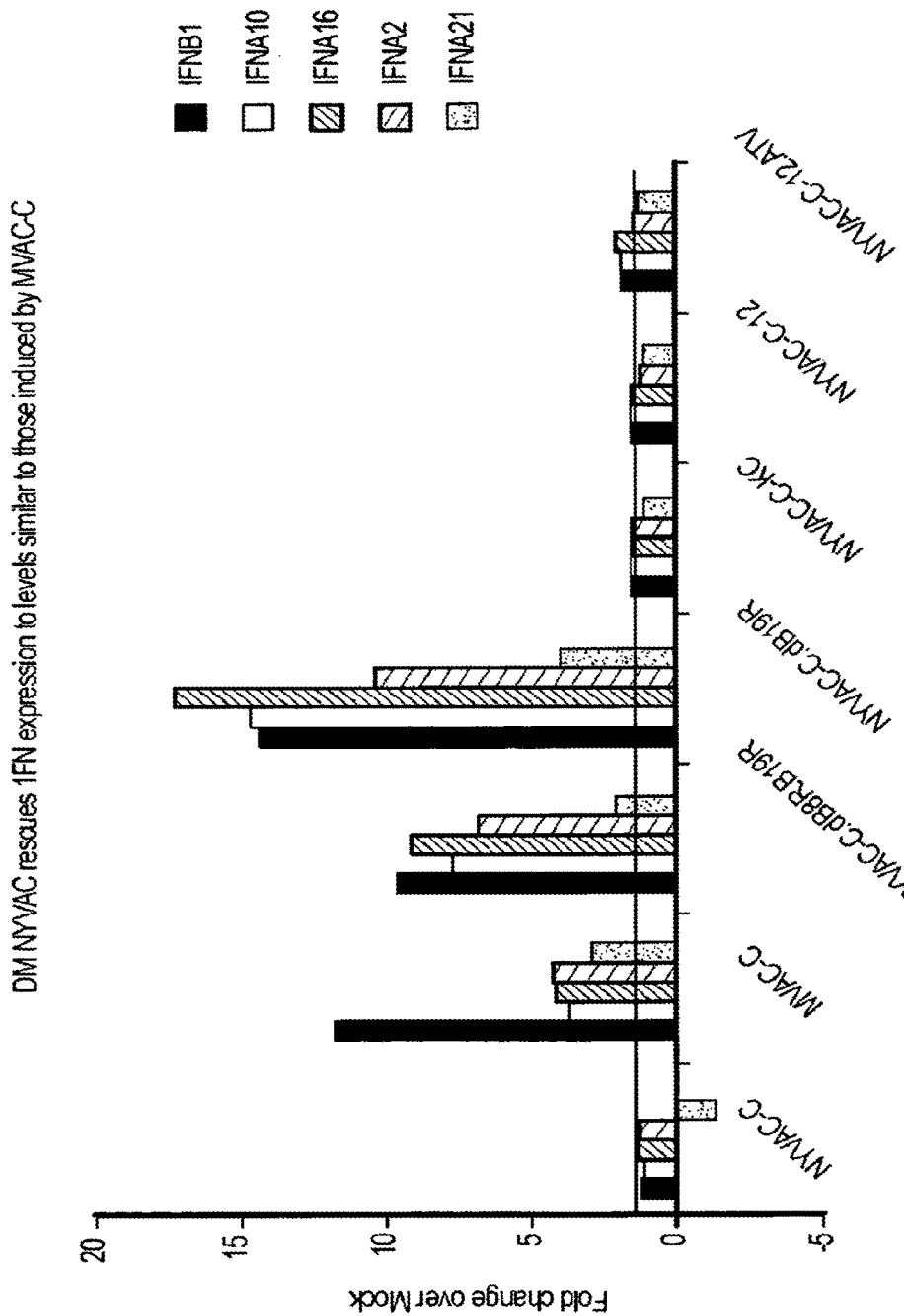
Figure 15C:
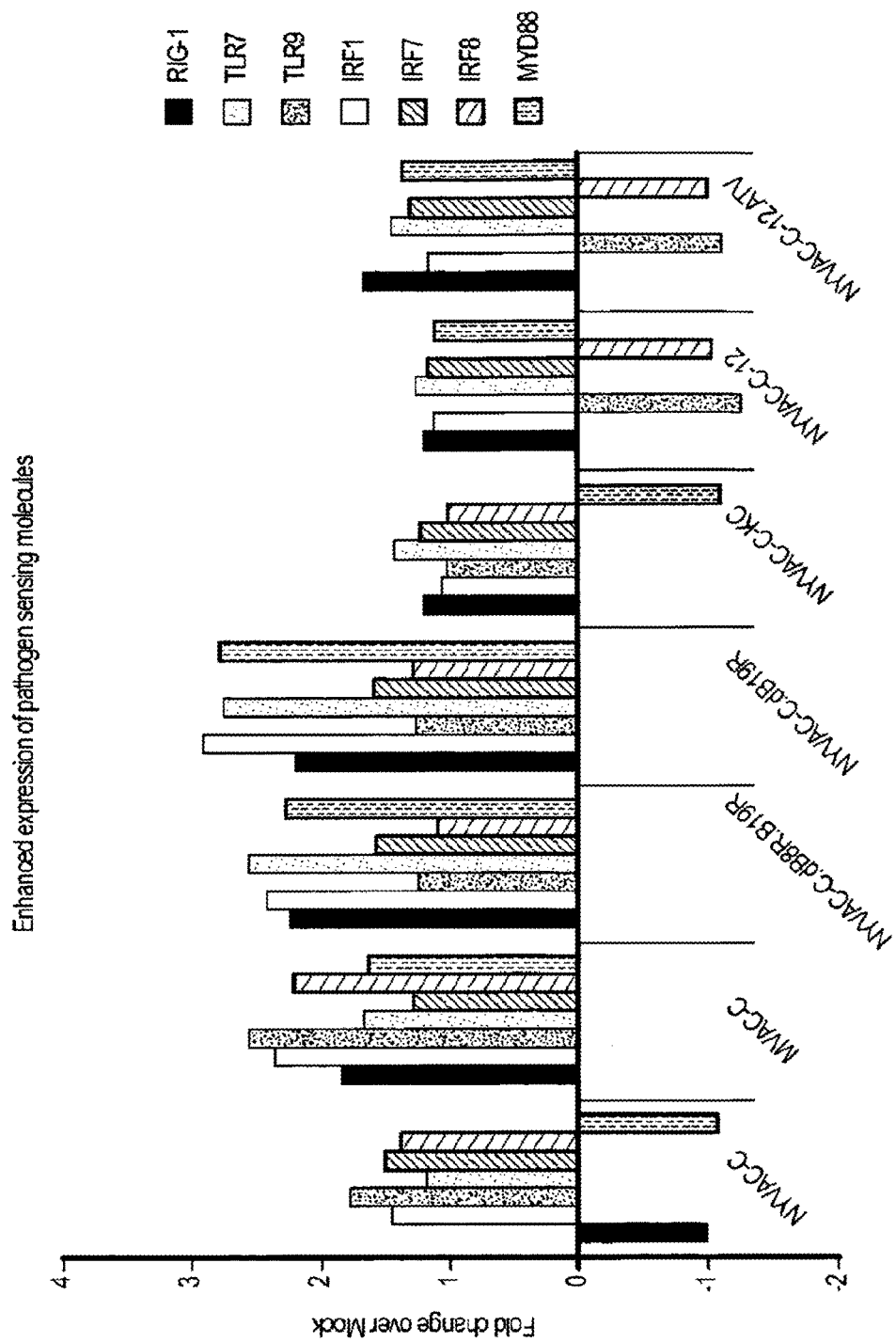
Figure 15D:
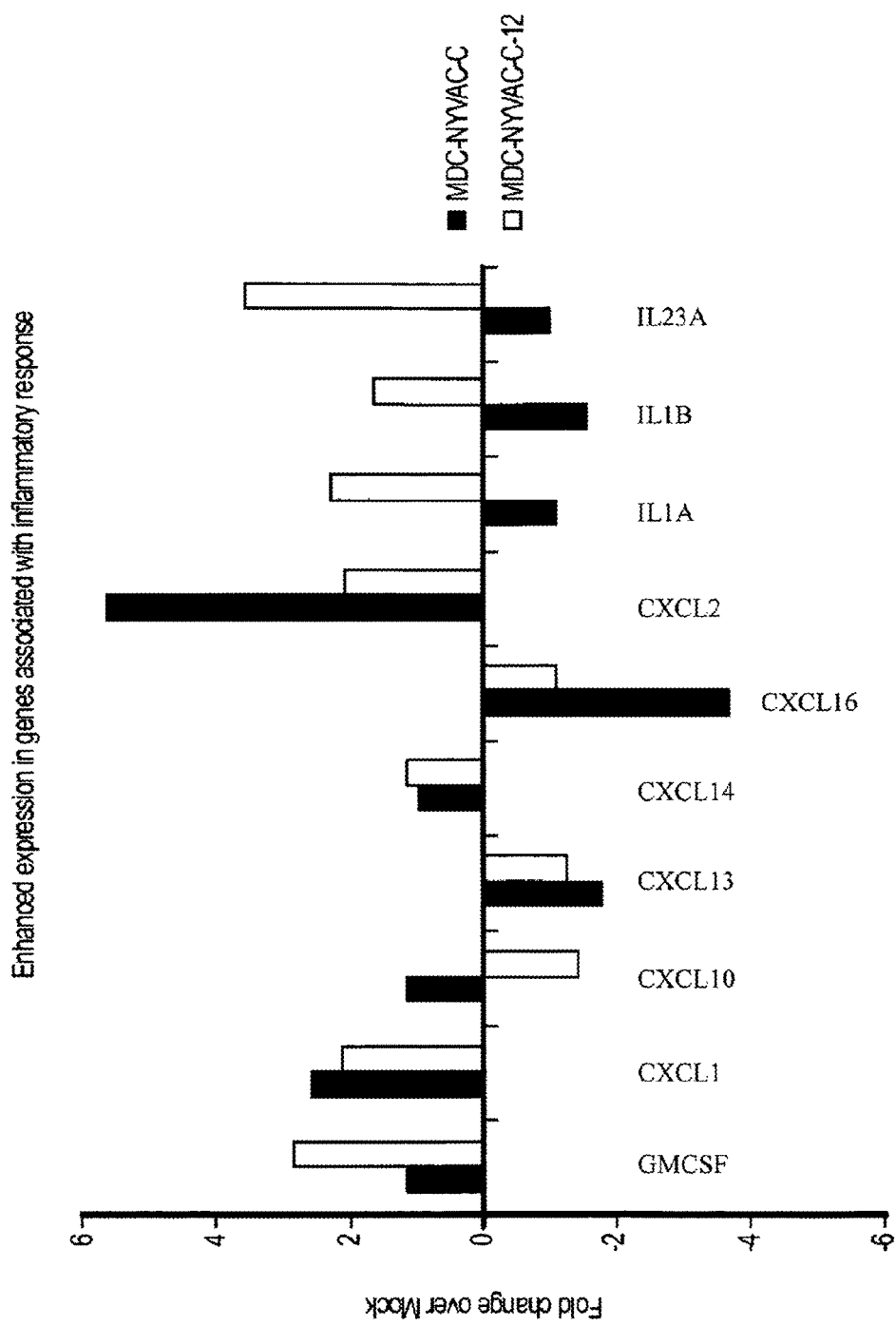

It is believed that virus having the E3L gene replaced by the ATV eIF2αH gene induces signal transduction through NF-κB and IRF-3, while sparing viral protein synthesis from the inhibitory effects of PKR activation. Replication of viruses expressing ATV eIF2αH was limited to a single round by replacing the E3L gene with the gene for the ATV PKR inhibitor. Unlike its parental virus, this virus is highly sensitive to anti-viral effects of interferon. Without being bound by theory, it is believed that the unique interferon-sensitivity of this virus limits replication, to a single round. In addition to limiting replication to a single round in human cells, this modification provides increased pro-inflammatory signal transduction and increased pro-inflammatory gene expression to occur in infected cells. This virus also induces a potent Th1 dominated immune response at low doses. Thus, this virus has the intrinsic safety profile of NYVAC with replication limited by induction and sensitivity to IFN, and increased pro-inflammatory signal transduction and increased pro-inflammatory gene expression.

C. Recombinant Vector Compositions

For administration to a host, recombinant virus is typically, but not necessarily (e.g., for the animal experiments described herein) maintained in a liquid form, with an extractable volume of 1 ml to 1.1 ml in single dose 3 ml vials stored at −20° C. The composition contains approximately $10^8$ $DICC_{50}$ recombinant vector (e.g., recombinant NYVAC), 0.25 ml 10 mM Tris-HCl buffer; pH 7.5, 0.25 ml Virus stabilizer (lactoglutamate); and, 0.5 ml freeze-drying medium.

D. Immunological Data

The recombinant viruses generated herein were tested for their ability to improve the immune response. The results of these studies are shown below.

1. T-Cell Assays

Analysis of the in vitro immunogenicity of the replication-competent NYVAC-C-KC and NYVAC-C+12-ATVh revealed a significant improvement of the ability to stimulate recall HIV-1-specific CD8 T-cell proliferative responses as compared to non-replication competent NYVAC-C (e.g., "wild-type" NYVAC-C). All of the replication competent recombinant viruses (e.g., NYVAC-C-KC and NYVAC-C+12-ATVh) tested were able to induce an HIV-1-specific CD8 T-cell responses in the range of 10-15%, whereas NYVAC-C exhibited a range of CD8 T-cell responses below 0.5%. These data were obtained in several independent experiments; two examples are shown in FIG. 12A. Furthermore, deletion of B8R and B19R genes on NYVAC-C-KC (e.g., NYVAC-C-KC-ΔB8R/ΔB19R) further increased the in vitro immunogenicity in the range of about 30%, as shown in FIG. 12B. Of note, these viruses were tested in a dose-dependent manner (ranging from $10^7$-$10^3$ PFU, i.e. corresponding to a range of MOI going from 10-0.001) in a conventional 6-day CFSE proliferation assay. The proportion of proliferating cells (i.e. $CFSE^{low}$ cells) was gated on live $CD3^+CD8^+$ T cells after 6 days of in vitro stimulation with the different doses of virus.

2. DC Maturation and Cross Presentation

The above-described NYVAC recombinant vectors were tested for their effect on dendritic cell (DC) maturation and antigen processing to HIV specific CD8 T cells. Maturation of monocyte derived human DCs was measured 48 hrs post infection by the expression levels of several co-stimulatory molecules by FACS analysis. Antigen presentation was analyzed after direct infection of DCs and after cross presentation, where the DCs have been incubated with infected apoptotic HeLa cells. Cytokine production by HIV-specific CD8 T cells was measured upon overnight stimulation with the DCs, either directly infected or incubated with HeLa cells.

Enhanced DC maturation was repeatedly observed in DCs infected with the B19R single and B8R/B19R double deletion mutants. Results from a representative experiment are shown in FIG. 13A. Forty eight hours after infection, increased expression of CD86, HLA-DR, HLA-A2 and CD80 was observed. These and other single deletion mutants, however, are not different from NYVAC-C in their antigen presentation. In contrast, the replication competent virus variants showed enhanced antigen presentation in both direct and cross presentation assays compared to NYVAC-C, as determined by the number of single, double and triple cytokine (IFN-γ, TNF-α, MIP-1β) producing CD8 T cells. Results from a representative experiment of NYVAC-C KC are shown in FIG. 13B.

3. Macrophages

The innate immune response elicited by wild-type and modified NYVAC poxvirus was assessed by measuring IL-8 production by human THP-1 macrophages (FIG. 14A) and whole blood (FIG. 14B). THP-1 cells (TIB-202, American Type Culture Collection) were differentiated into macrophages by treatment with 0.5 μM phorbol 12-myristate 13-acetate for 24 h. THP-1 cells were then infected with increasing multiplicity of infection of wild-type and mutant NYVAC and NYVAC-C. After 1 h of contact with cells, the virus inoculum was removed and fresh medium added to the cultures. Cell-culture supernatants collected 24 h after infection were used to quantify IL-8 by ELISA. For whole blood assay, 100 μl of heparinized whole blood collected from three healthy volunteers were diluted 5-fold in RPMI 1640 medium containing viruses and incubated for 24 h at 37° C. in the presence of 5% $CO_2$. Samples were centrifuged, and cell-free supernatants collected to quantify IL-8 and TNF by ELISA.

Results showed that expression of the clade-C gag-pol-nef HIV polypeptides in NYVAC (ie NYVAC-C) enhanced IL-8 production by THP-1 cells by two to four-fold (FIG. 14A). NYVAC-C with B8R, B19R and B8R-B19R gene deletions and replication competent NYVAC-KC and NYVAC-C-KC induced more IL-8 than NYVAC, but did not increase the IL-8 response as compared to NYVAC-C. In whole blood, NYVAC-C induced less IL-8 than NYVAC, whereas NYVAC-C with B19R and B8R-B19R gene deletions and replication competent NYVAC-KC, NYVAC-C-KC, NYVAC-C+12 and NYVAC-C+12-ATV increased IL-8 release by 1.5 to 2.5-fold. NYVAC-C, NYVAC-C with B19R and B8R-B19R gene deletions and replication competent NYVAC-KC and NYVAC-C+12-ATV also increased TNF release by whole blood.

4. Gene Array

Gene expression profiling was conducted following PD-1 engagement. Myeloid or plasmacytoid dendritic cells were infected with wild type and mutant pox viruses for 6 hours. Cells were harvested and RNA was extracted using Qiagen RNeasy™ kit (Cat #74104) according to the manufacturer's instructions. DNA was then hybridized on Illumina™ chips.

Quantification was done using Illumina BeadStation™ 500GX scanner and Illumina BeadStudio™ 3 Software. Illumina gene averaged data was exported from BeadStudio™ as raw data and was screened for quality (visual inspection of the chip image, analysis of the Illumina controls, diagnostic plots). Outliers were removed before subsequent analysis. The data was normalized using quantile method. Genes having intensities below background across all samples were filtered out and values below background were surrogate replaced. The data was log 2 transformed before its analysis in R statistical package "Linear models for microarray analysis" (LIMMA) where a fold change greater or equal to 1.5, or less or equal to −1.5 and a moderated p-value less or equal to 0.05 was considered significant. The NYVAC-C-ΔB8R/ΔB19R double mutants induced gene expression profiles similar to those induces by MVA expressing the C clade, as described below:

Enhanced expression of early and late chemokines (CXC110, CXCL13, CXCL9, CXCL16; FIG. 15A);

Enhanced expression of chemokines that attract T cells, B cells, NK cells and neutrophils;

Enhanced expression of cytokines which activate T cells (IL-15) (FIG. 15A);

Enhanced expression of the IFN-α and IFN-β "machinery" (FIG. 15B);

Enhanced expression pathogen sensory molecules including RIG-1, TLR-7 (FIG. 15C);

Induced the expression of the inflammsomes genes (FIG. 15D).

Induced a unique transcriptional network including but not limited to IRF-1, IRF-7, STAT-5, NFKB, STAT3, STAT1, and IRF-10; and, Induced a transcriptional network signature resembling that induced by YF vaccine.

It is noted that similar gene expression signatures were elicited by macrophages to and DC.

All documents cited in this disclosure are hereby incorporated into this disclosure in their entirety. While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. A recombinant NYVAC vector encoding in its genome C7L (SEQ ID NO: 17) and K1L (SEQ ID NO: 27), wherein the C7L (SEQ ID NO: 17) and K1L (SEQ ID NO: 27) coding sequences are adjacent to one another in the genome.

2. The recombinant NYVAC vector of claim 1, further comprising a polynucleotide encoding Ambystoma tigrinum virus Eukaryotic Translation Initiation Factor (ATV eIF2αH) (SEQ ID NO. 29).

3. The recombinant NYVAC vector of claim 1, the vector further comprising a polynucleotide encoding an immunogen.

4. The recombinant NYVAC vector of claim 3, wherein the immunogen directs an immune response against an antigen selected from the group consisting of a viral target antigen, a bacterial target antigen, a parasitic target antigen, or a tumor target antigen.

5. The recombinant NYVAC vector of claim 4, wherein the viral target antigen is derived from a virus selected from the group consisting of an adenovirus, herpes virus, epstein-barr virus, human cytomegalovirus, varicella-zoster virus, poxvirus, parvovirus, papillomavirus, reovirus, picornavirus, coxsackie virus, hepatitis A virus, poliovirus, togavirus, rubella virus, flavivirus, hepatitis C virus, yellow fever virus, dengue virus, west Nile virus, orthomyxovirus, influenza virus, rhabdovirus, paramyxovirus, measles virus, mumps virus, parainfluenza virus, respiratory syncytial virus, rhabdovirus, rabies virus, retrovirus, human immunodeficiency virus (HIV), hepadnavirus, and hepatitis B virus.

6. The recombinant NYVAC vector of claim 5, wherein the virus is human immunodeficiency virus (HIV).

7. The recombinant NYVAC vector of claim 6, wherein the immunogen is encoded by the genome of HIV-1 inter-subtype (C/B').

8. The recombinant NYVAC vector of claim 6, wherein the immunogen is selected from the group consisting of Env, Gag, Nef, and Pol.

9. The recombinant NYVAC vector of claim 8, wherein the immunogen is provided by a GAG-POL-NEF fusion protein.

10. The recombinant NYVAC vector of claim 6, wherein the immunogen has the amino acid sequence selected from the group consisting of ENV, GAG, POL, NEF, VGNLWVTVYYGVPVW (SEQ ID NO. 56), WVTVYYGVPVWKGAT (SEQ ID NO. 57), GATTTLFCASDAKAY (SEQ ID NO. 58), TTLFCASDAKAYDTE (SEQ ID NO. 59), THACVPADPNPQEMV (SEQ ID NO. 60), ENVTENFNMWKNEMV (SEQ ID NO. 61), ENFNMWKNEMVNQMQ (SEQ ID NO. 62), EMVNQMQED-VISLWD (SEQ ID NO. 63), CVKLTPLCVTLECRN (SEQ ID NO. 64), NCSFNATTVVRDRKQ (SEQ ID NO. 65), NATTVVRDRKQTVYA (SEQ ID NO. 66), VYALFYRLDIVPLTK (SEQ ID NO. 67), FYRLDIVPLTKKNYS (SEQ ID NO. 68), INCNTSAITQACPKV (SEQ ID NO. 69), PKVTFDPIPIHYCTP (SEQ ID NO. 70), FDPIPIHYCTPAGYA (SEQ ID NO. 71), TGDIIGDIRQAHCNI (SEQ ID NO. 72), SSSIITIPCRIKQII (SEQ ID NO. 73), ITIPCRIKQIINMWQ (SEQ ID NO. 74), CRIKQIINMWQEVGR (SEQ ID NO. 75), VGRAMYAPPIKGNIT (SEQ ID NO. 76), MYAPPIKGNITCKSN (SEQ ID NO. 77), PIKGNITCKSNITGL (SEQ ID NO. 78), ETFRPGGGDMRNNWR (SEQ ID NO. 79), ELYKYKVVEIKPLGV (SEQ ID NO. 80), YKVVEIKPLGVAPTT (SEQ ID NO. 81), EIKPLGVAPTTTKRR (SEQ ID NO. 82), LGVAPTTTKRRVVER (SEQ ID NO. 83), and YSENSSEYY (SEQ ID NO. 84).

11. The recombinant NYVAC vector of claim 4, wherein the bacterial target antigen is derived from a bacterial organism selected from the group consisting of Bacillus anthracis, Bordetella pertussis, Borrelia burgdorferi, Bmeella abortus, Brucella canis, Brucella melitensis, Brucella suis, Campylobacter jejuni, Chlamydia pneumoniae, Chlamydia psittaci, Chlamydia trachomatis, Clostridium botulinum, Clostridium difficile, Clostridium perfringens, Clostridium tetani, Corynebacterium diptheriae, Enterococcus faecalis, enterococcus faecum, Escherichia coli, Francisella tularensis, Haemophilus influenza, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhea, Neisseria meningitidis, Pseudomonas aeruginosa, Rickettsia rickettsii, Salmonella typhi, Salmonella typhinurium, Shigella sonnei, Staphylococcus aureus, Staphylococcus epidermidis, Staphylococcus saprophyticus, coagulase negative staphylococcus, Streptococcus agalactiae, Streptococcus pneumoniae, Streptococcus pyrogenes, Treponema pallidum, Vibrio cholerae, and Yersinia pestis.

12. The recombinant NYVAC vector of claim 4, wherein the parasite target antigen is derived from a bacterial organism selected from the group consisting of Ancylostoma duodenale, Anisakis spp., Ascaris lumbricoides, Balantidium coli, Cestoda spp., Cimicidae spp., Clonorchis sinensis, Dicrocoelium dendriticum, Dicrocoelium hospes, Diphyllobothrium latum, Dracunculus spp., Echinococcus granulosus, Echinococcus multif ocularis, Entamoeba histolytica, Enterobius vermicularis, Fasciola hepatica, Fasciola magna, Fasciola gigantica, Fasciola jacksoni, Fasciolopsis buski, Giar-

*dia lamblia, Gnathostoma* spp.*, Hymenolepis nana, Hymenolepis diminuta, Leishmania* spp.*, Loa boa, Metorchis conjunctus, Metorchis albidus, Necator americanus, Oestroidea* spp.*, Onchocercidae* spp.*, Opisthorchis viverrini, Opisthorchis felineus, Opisthorchis guayaquilensis, Opisthorchis noverca, Plasmodium falciparum, Protofasciola robusta, Parafasciolopsis fasc-iomorphae, Paragonimus westermani, Schistosoma mansoni, Schistosoma japonicum, Schistosoma mekongi, Schistosoma haematobium, Spirometra erinaceieuropaei, Strongyloides stercoralis, Taenia saginata, Taenia solium, Toxocara canis, Toxocara cati, Toxoplasma gondii, Trichobilharzia regent, Trichinella spiralis, Trichuris trichiura, Trombiculidae* spp.*, Trypanosoma* spp.*, Tungapenetrans,* and *Wuchereria bancrofti.*

13. The recombinant NYVAC vector of claim 4, wherein the tumor target antigen is selected from the group consisting of: a gp100 (MART-1/Melan A), gp75 (TRP-1), tyrosinase, NY-ESO-1, melanoma proteoglycan, a MAGE family antigen, a BAGE family antigen, a GAGE family antigen, a RAGE family antigens, N-acetylglucosaminyltransferase-V, p15, β-catenin, MUM-1, cyclin dependent kinase-4 (CDK4), p21-ras, BCR-abl, p53, p185 (HER2/neu), epidermal growth factor receptor (EGFR), carcinoembryonic antigen (CEA), a carcinoma-associated mutated mucin, MUC-1, prostate specific antigen (PSA), prostate specific membrane antigen (PSMA), KSA, kinesin 2, HIP-55, TGFβ-1 anti-apoptotic factor, tumor protein D52, H1FT, NY-BR-1, NY-BR-62, NY-BR-75, NY-BR-85, NY-BR- 87, NY-BR-96, and a pancreatic cancer antigen.

14. A composition comprising the recombinant NYVAC vector of claim 4 and a pharmaceutically acceptable carrier.

15. A method of inducing an immune response in a host against a viral target antigen, a bacterial target antigen, a parasitic target antigen, or a tumor target antigen comprising administering an effective amount of the composition of claim 14 to the host.

16. The method of claim 15, for inducing am immune response in a host against human immunodeficiency virus (HIV) wherein the vector encodes an immunogen derived from HIV and administering to the host a peptide selected from the group consisting of ENV, GAG, POL, NET, VGNLWVTVYYGVPVW (SEQ ID NO. 31), WVTVYYGVPVWKGAT (SEQ ID NO. 32), GATTTLFCASDAKAY (SEQ ID NO. 33), TTLFCASDAKAYDTE (SEQ ID NO. 34), THACVPADPNPQEMV (SEQ ID NO. 35), ENVTENFNMWKNEMV (SEQ ID NO. 36), ENFNMWKNEMVNQMQ (SEQ ID NO. 37), EMVNQMQEDVISLWD (SEQ ID NO. 38), CVKLTPLCVTLECRN (SEQ ID NO. 39), NCSFNATTVVRDRKQ (SEQ ID NO. 40), NATTVVRDRKQTVYA (SEQ ID NO. 41), VYALFYRLDIVPLTK (SEQ ID NO. 42), FYRLDIVPLTKKNYS (SEQ ID NO. 43), INCNTSAITQACPKV (SEQ ID NO. 44), PKVTFDPIPIHYCTP (SEQ ID NO. 45), FDPIPIHYCTPAGYA (SEQ ID NO. 46), TGDIIGDIRQAHCNI (SEQ ID NO. 47), SSSIITIPCRIKQII (SEQ ID NO. 48), ITIPCRIKQIINMWQ (SEQ ID NO. 49), CRIKQIINMWQEVGR (SEQ ID NO. 50), VGRAMYAPPIKGNIT (SEQ ID NO. 51), MYAPPIKGNITCKSN (SEQ II) NO. 52), PIKGNITCKSNITGL (SEQ ID NO. 53), ETFRPGGGDMRNNWR (SEQ ID NO. 54), ELYKYKVVEIKPLGV (SEQ ID NO. 55), YKVVEIKPLGVAPTT (SEQ ID NO. 56), EIKPLGVAPTTTKRR (SEQ ID NO. 57), LGVAPTTTKRRVVER (SEQ ID NO. 58), and YSENSSEYY (SEQ ID NO. 59).

17. The method of claim 15, wherein the host is a human being.

* * * * *

```
                        SEQUENCE LISTING

<160> NUMBER OF SEQ ID NOS: 82

<210> SEQ ID NO 1
<211> LENGTH: 272
<212> TYPE: PRT
<213> ORGANISM: Human immunodeficiency virus

<400> SEQUENCE: 1

Met Arg Tyr Ile Ile Ile Leu Ala Val Leu Phe Ile Asn Ser Ile His
1               5                   10                  15

Ala Lys Ile Thr Ser Tyr Lys Phe Glu Ser Val Asn Phe Asp Ser Lys
            20                  25                  30

Ile Glu Trp Thr Gly Asp Gly Leu Tyr Asn Ile Ser Leu Lys Asn Tyr
        35                  40                  45

Gly Ile Lys Thr Trp Gln Thr Met Tyr Thr Asn Val Pro Glu Gly Thr
    50                  55                  60

Tyr Asp Ile Ser Ala Phe Pro Lys Asn Asp Phe Val Ser Phe Trp Val
65                  70                  75                  80

Lys Phe Glu Gln Gly Asp Tyr Lys Val Glu Glu Tyr Cys Thr Gly Leu
                85                  90                  95

Cys Val Glu Val Lys Ile Gly Pro Pro Thr Val Thr Leu Thr Glu Tyr
            100                 105                 110

Asp Asp His Ile Asn Leu Tyr Ile Glu His Pro Tyr Ala Thr Arg Gly
        115                 120                 125

Ser Lys Lys Ile Pro Ile Tyr Lys Arg Gly Asp Met Cys Asp Ile Tyr
    130                 135                 140

Leu Leu Tyr Thr Ala Asn Phe Thr Phe Gly Asp Ser Glu Glu Pro Val
145                 150                 155                 160

Thr Tyr Asp Ile Asp Asp Tyr Asp Cys Thr Ser Thr Gly Cys Ser Ile
                165                 170                 175

Asp Phe Ala Thr Thr Glu Lys Val Cys Val Thr Ala Gln Gly Ala Thr
            180                 185                 190

Glu Gly Phe Leu Glu Lys Ile Thr Pro Trp Ser Ser Glu Val Cys Leu
        195                 200                 205

Thr Pro Lys Lys Asn Val Tyr Thr Cys Ala Ile Arg Ser Lys Glu Asp
```

-continued

```
                210                 215                 220
Val Pro Asn Phe Lys Asp Lys Met Ala Arg Val Ile Lys Arg Lys Phe
225                 230                 235                 240

Asn Lys Gln Ser Gln Ser Tyr Leu Thr Lys Phe Leu Gly Ser Thr Ser
                245                 250                 255

Asn Asp Val Thr Thr Phe Leu Ser Met Leu Asn Leu Thr Lys Tyr Ser
            260                 265                 270

<210> SEQ ID NO 2
<211> LENGTH: 819
<212> TYPE: DNA
<213> ORGANISM: Human immunodeficiency virus

<400> SEQUENCE: 2
atgagatata ttataattct cgcagttttg ttcattaata gtatacacgc taaaataact      60
agttataagt ttgaatccgt caattttgat tccaaaattg aatggactgg ggatggtcta     120
tacaatatat cccttaaaaa ttatggcatc aagacgtggc aaacaatgta caaatgta      180 ccagaaggaa catacgacat atccgcattt ccaagaatg atttcgtatc tttctgggtt     240
aaatttgaac aaggcgatta taagtgaa gagtattgta cgggactatg cgtcgaagta     300
aaaattggac caccgactgt aacattgact gaatacgacg accatatcaa tttgtacatc     360
gagcatccgt atgctactag aggtagcaaa aagattccta tttacaaacg cggtgacatg     420
tgtgatatct acttgttgta tacggctaac ttcacattcg gagattctga agaaccagta     480
acatatgata tcgatgacta cgattgcacg tctacaggtt gcagcataga ctttgccaca     540
acagaaaaag tgtgcgtgac agcacaggga gccacagaag ggtttctcga aaaattact      600 ccatggagtt cggaagtatg tctgacacct aaaaagaatg tatatacatg tgcaattaga     660 tccaagaag atgttcccaa tttcaaggac aaaatggcca gagttatcaa gagaaatt       720 aataaacagt ctcaatctta tttaactaaa tttctcggta gcacatcaaa tgatgttacc     780 actttttctta gcatgcttaa cttgactaaa tattcataa                            819

<210> SEQ ID NO 3
<211> LENGTH: 353
<212> TYPE: PRT
<213> ORGANISM: Human immunodeficiency virus

<400> SEQUENCE: 3

Met Thr Met Lys Met Met Val His Ile Tyr Phe Val Ser Leu Ser Leu
1               5                   10                  15

Leu Leu Leu Leu Phe His Ser Tyr Ala Ile Asp Ile Glu Asn Glu Ile
                20                  25                  30

Thr Glu Phe Phe Asn Lys Met Arg Asp Thr Leu Pro Ala Lys Asp Ser
            35                  40                  45

Lys Trp Leu Asn Pro Ala Cys Met Phe Gly Gly Thr Met Asn Asp Met
        50                  55                  60

Ala Thr Leu Gly Glu Pro Phe Ser Ala Lys Cys Pro Pro Ile Glu Asp
65                  70                  75                  80

Ser Leu Leu Ser His Arg Tyr Lys Asp Tyr Val Val Lys Trp Glu Arg
                85                  90                  95

Leu Glu Lys Asn Arg Arg Arg Gln Val Ser Asn Lys Arg Val Lys His
                100                 105                 110

Gly Asp Leu Trp Ile Ala Asn Tyr Thr Ser Lys Phe Ser Asn Arg Arg
            115                 120                 125
```

```
Tyr Leu Cys Thr Val Thr Thr Lys Asn Gly Asp Cys Val Gln Gly Ile
    130                 135                 140
Val Arg Ser His Ile Lys Lys Pro Pro Ser Cys Ile Pro Lys Thr Tyr
145                 150                 155                 160
Glu Leu Gly Thr His Asp Lys Tyr Gly Ile Asp Leu Tyr Cys Gly Ile
                165                 170                 175
Leu Tyr Ala Lys His Tyr Asn Asn Ile Thr Trp Tyr Lys Asp Asn Lys
                180                 185                 190
Glu Ile Asn Ile Asp Asp Ile Lys Tyr Ser Gln Thr Gly Lys Glu Leu
                195                 200                 205
Ile Ile His Asn Pro Glu Leu Glu Asp Ser Gly Arg Tyr Asp Cys Tyr
    210                 215                 220
Val His Tyr Asp Asp Val Arg Ile Lys Asn Asp Ile Val Val Ser Arg
225                 230                 235                 240
Cys Lys Ile Leu Thr Val Ile Pro Ser Gln Asp His Arg Phe Lys Leu
                245                 250                 255
Ile Leu Asp Pro Lys Ile Asn Val Thr Ile Gly Glu Pro Ala Asn Ile
                260                 265                 270
Thr Cys Thr Ala Val Ser Thr Ser Leu Leu Ile Asp Asp Val Leu Ile
    275                 280                 285
Glu Trp Glu Asn Pro Ser Gly Trp Leu Ile Gly Phe Asp Phe Asp Val
    290                 295                 300
Tyr Ser Val Leu Thr Ser Arg Gly Gly Ile Thr Glu Ala Thr Leu Tyr
305                 310                 315                 320
Phe Glu Asn Val Thr Glu Glu Tyr Ile Gly Asn Thr Tyr Lys Cys Arg
                325                 330                 335
Gly His Asn Tyr Tyr Phe Glu Lys Thr Leu Thr Thr Val Val Leu
                340                 345                 350
Glu

<210> SEQ ID NO 4
<211> LENGTH: 1062
<212> TYPE: DNA
<213> ORGANISM: Human immunodeficiency virus

<400> SEQUENCE: 4
atgacgatga aaatgatggt acatatatat ttcgtatcat tatcattatt gttattgcta      60
ttccacagtt acgccataga catcgaaaat gaaatcacag aattcttcaa taaaatgaga     120
gatactctac cagctaaaga ctctaaatgg ttgaatccag catgtatgtt cggaggcaca     180
atgaatgata tggccactct aggagagcca ttcagtgcaa agtgtcctcc tattgaagac     240
agtcttttat cgcacagata taagactat gtggttaaat gggagaggct agaaaagaat     300
agacggcgac aggtttctaa taacgtgtt aaacatggtg atttatggat agccaactat     360
acatctaaat tcagtaaccg taggtatttg tgcaccgtaa ctacaaagaa tggtgactgt     420
gttcagggta tagttagatc tcatattaaa aaacctcctt catgcattcc aaaaacatat     480
gaactaggta tcatgataa gtatggcata gacttatact gtggaattct ttacgcaaaa     540
cattataata atataacttg gtataaagat aataaggaaa ttaatatcga cgacattaag     600
tattcacaaa cgggaaagga attaattatt cataatccag agttagaaga tagcggaaga     660
tacgactgtt acgttcatta cgacgacgtt agaatcaaga atgatatcgt agtatcaaga     720
tgtaaaaatac ttcgggttat accgtcacaa gaccacaggt ttaaactaat actagatccg     780
aaaatcaacg taacgatagg agaaccctgcc aatataacat gcactgctgt gtcaacgtca     840
```

```
ttattgattg acgatgtact gattgaatgg gaaaatccat ccggatggct tataggattc     900
gattttgatg tatactctgt tttaactagt agaggcggta tcaccgaggc gaccttgtac     960
tttgaaaatg ttactgaaga atatataggt aatacatata aatgtcgtgg acacaactat   1020
tattttgaaa aaaccettac aactacagta gtattggagt aa                      1062
```

<210> SEQ ID NO 5
<211> LENGTH: 224
<212> TYPE: PRT
<213> ORGANISM: Human immunodeficiency virus

<400> SEQUENCE: 5

```
Met Val Lys Asn Asn Lys Ile Ser Asn Ser Cys Arg Met Ile Met Ser
1               5                   10                  15

Thr Asn Pro Asn Asn Ile Leu Met Arg His Leu Lys Asn Leu Thr Asp
            20                  25                  30

Asp Glu Phe Lys Cys Ile Ile His Arg Ser Ser Asp Phe Leu Tyr Leu
        35                  40                  45

Ser Asp Ser Asp Tyr Thr Ser Ile Thr Lys Glu Thr Leu Val Ser Glu
    50                  55                  60

Ile Val Glu Glu Tyr Pro Asp Asp Cys Asn Lys Ile Leu Ala Ile Ile
65                  70                  75                  80

Phe Leu Val Leu Asp Lys Asp Ile Asp Val Asp Ile Glu Thr Lys Leu
                85                  90                  95

Lys Pro Lys Pro Ala Val Arg Phe Ala Ile Leu Asp Lys Met Thr Glu
            100                 105                 110

Asp Ile Lys Leu Thr Asp Leu Val Arg His Tyr Phe Arg Tyr Ile Glu
        115                 120                 125

Gln Asp Ile Pro Leu Gly Pro Leu Phe Lys Lys Ile Asp Ser Tyr Arg
    130                 135                 140

Thr Arg Ala Ile Asn Lys Tyr Ser Lys Glu Leu Gly Leu Ala Thr Glu
145                 150                 155                 160

Tyr Phe Asn Lys Tyr Gly His Leu Met Phe Tyr Thr Leu Pro Ile Pro
                165                 170                 175

Tyr Asn Arg Phe Phe Cys Arg Asn Ser Ile Gly Phe Leu Ala Val Leu
            180                 185                 190

Ser Pro Thr Ile Gly His Val Lys Ala Phe Tyr Lys Phe Ile Glu Tyr
        195                 200                 205

Val Ser Ile Asp Asp Arg Arg Lys Phe Lys Lys Glu Leu Met Ser Lys
    210                 215                 220
```

<210> SEQ ID NO 6
<211> LENGTH: 675
<212> TYPE: DNA
<213> ORGANISM: Human immunodeficiency virus

<400> SEQUENCE: 6

```
atggtgaaaa ataataaaat aagtaatagc tgccgaatga taatgagtac taaccctaat      60
aatattctaa tgagacatct caaaaatctt acagatgatg aatttaaatg tattattcat     120
cgatcatctg attttcttta tttgtccgat agtgactata ctagtataac caaagaaaca     180
ttagttagtg agatcgtaga agaatatccg gatgattgta ataaaatatt agctattata     240
tttttggtgt tagataaaga catagatgta gatatagaaa ctaaactaaa gcctaaaccc     300
gcagttagat ttgccattct agacaagatg actgaggata ttaaactaac ggatctagtc     360
```

```
agacattatt ttagatacat agaacaagat ataccactag gtccgttgtt caaaaaata      420 gattcgtaca gaacaagagc cattaataag tattcgaaag agttaggatt ggctactgaa      480
tactttaata agtacggaca tttaatgttt tatactctcc ctataccata taacagattc      540
ttttgtagaa attcgatagg cttttttagcg gttctatcgc ctacgatagg acacgtaaaa     600
gcattttata aattcataga atatgtttct atagatgata gacgcaaatt taaaaggaa       660 ttaatgtcga aatga                                                       675

<210> SEQ ID NO 7
<211> LENGTH: 512
<212> TYPE: PRT
<213> ORGANISM: Human immunodeficiency virus

<400> SEQUENCE: 7
```

Met Glu Ser Val Ile Phe Ser Ile Asn Gly Glu Ile Ile Gln Val Asn
1               5                   10                  15

Lys Glu Ile Ile Thr Ala Ser Pro Tyr Asn Phe Phe Lys Arg Ile Gln
                20                  25                  30

Asp His His Leu Lys Asp Glu Ala Ile Ile Leu Asn Gly Ile Asn Tyr
            35                  40                  45

His Ala Phe Glu Ser Leu Leu Asp Tyr Met Arg Trp Lys Lys Ile Asn
        50                  55                  60

Ile Thr Ile Asn Asn Val Glu Met Ile Leu Val Ala Ala Val Ile Ile
65                  70                  75                  80

Asp Val Pro Pro Val Asp Leu Cys Val Lys Thr Met Ile His Asn
                85                  90                  95

Ile Asn Ser Thr Asn Cys Ile Arg Met Phe Asn Phe Ser Lys Arg Tyr
            100                 105                 110

Gly Ile Lys Lys Leu Tyr Asn Ala Ser Met Ser Glu Ile Ile Asn Asn
        115                 120                 125

Ile Thr Ala Val Thr Ser Asp Pro Glu Phe Gly Lys Leu Ser Lys Asp
    130                 135                 140

Glu Leu Thr Thr Ile Leu Ser His Glu Asp Val Asn Val Asn His Glu
145                 150                 155                 160

Asp Val Thr Ala Met Ile Leu Leu Lys Trp Ile His Lys Asn Pro Asn
                165                 170                 175

Asp Val Asp Ile Ile Asn Ile Leu His Pro Lys Phe Met Thr Asn Thr
            180                 185                 190

Met Arg Asn Ala Ile Ser Leu Leu Gly Leu Thr Ile Ser Lys Ser Thr
        195                 200                 205

Lys Pro Val Thr Arg Asn Gly Ile Lys His Asn Ile Val Ile Lys
    210                 215                 220

Asn Ser Asp Tyr Ile Ser Thr Ile Thr His Tyr Ser Pro Arg Thr Glu
225                 230                 235                 240

Tyr Trp Thr Ile Val Gly Asn Thr Asp Arg Gln Phe Tyr Asn Ala Asn
                245                 250                 255

Val Leu His Asn Cys Leu Tyr Ile Ile Gly Gly Met Ile Asn Asn Arg
            260                 265                 270

His Val Tyr Ser Val Ser Arg Val Asp Leu Glu Thr Lys Lys Trp Lys
        275                 280                 285

Thr Val Thr Asn Met Ser Ser Leu Lys Ser Glu Val Ser Thr Cys Val
    290                 295                 300

Asn Asp Gly Lys Leu Tyr Val Ile Gly Gly Leu Glu Phe Ser Ile Ser
305                 310                 315                 320

```
Thr Gly Val Ala Glu Tyr Leu Lys His Gly Thr Ser Lys Trp Ile Arg
            325                 330                 335

Leu Pro Asn Leu Ile Thr Pro Arg Tyr Ser Gly Ala Ser Val Phe Val
            340                 345                 350

Asn Asp Asp Ile Tyr Val Met Gly Gly Val Tyr Thr Thr Tyr Glu Lys
            355                 360                 365

Tyr Val Val Leu Asn Asp Val Glu Cys Phe Thr Lys Asn Arg Trp Ile
            370                 375                 380

Lys Lys Ser Pro Met Pro Arg His His Ser Ile Val Tyr Ala Val Glu
385                 390                 395                 400

Tyr Asp Gly Asp Ile Tyr Val Ile Thr Gly Ile Thr His Glu Thr Arg
            405                 410                 415

Asn Tyr Leu Tyr Lys Tyr Ile Val Lys Glu Asp Lys Trp Ile Glu Leu
            420                 425                 430

Tyr Met Tyr Phe Asn His Val Gly Lys Met Phe Val Cys Ser Cys Gly
            435                 440                 445

Asp Tyr Ile Leu Ile Ile Ala Asp Ala Lys Tyr Glu Tyr Tyr Pro Lys
            450                 455                 460

Ser Asn Thr Trp Asn Leu Phe Asp Met Ser Thr Arg Asn Ile Glu Tyr
465                 470                 475                 480

Tyr Asp Met Phe Thr Lys Asp Glu Thr Pro Lys Cys Asn Val Thr His
            485                 490                 495

Lys Ser Leu Pro Ser Phe Leu Ser Asn Cys Glu Lys Gln Phe Leu Gln
            500                 505                 510

<210> SEQ ID NO 8
<211> LENGTH: 1539
<212> TYPE: DNA
<213> ORGANISM: Human immunodeficiency virus

<400> SEQUENCE: 8
atggaaagcg tgatattttc tatcaatggg gaaattatac aagtgaataa ggaaattatt      60
acggcgtctc cgtataattt ttttaaacgc attcaggatc accatctaaa ggatgaagcg     120
attatattga atggtataaa ctatcacgcg tttgaatcgc attagactta tgcgctgg      180 aagaagataa acatcaccat aaacaatgta gaaatgatac tagttgctgc cgtaataatt     240
gatgttccgc ctgtagtaga tctatgtgta aaaactatga ttcataatat taattccaca     300
aattgtataa ggatgtttaa cttttctaaa agatatggaa ttaaaaaact atataatgcg     360
tcgatgtcag aaataatcaa caatattact gcggtgacat ccgatccaga atttggaaaa     420
ttatcaaagg atgaactgac aactatctta tcccacgaag acgttaacgt aaatcatgag     480
gatgttacag ctatgatatt attaaagtgg atacataaaa atccaaacga tgtagatatc     540
atcaacattt tacatcccaa gtttatgact aatactatgc gcaatgctat atcattgttg     600
ggattaacta tatccaaatc tacaaagcca gtgacacgaa atggtataaa acataatata     660
gtagtcatta aaaactctga ttatatatcc acaataaccc attactctcc taggacagaa     720
tattggacga tagtcggtaa tacagataga caattctata tgcaaatgt tttacataat     780 tgtctataca ttattggcgg catgattaac aatagacatg tttattccgt atcgcggta     840 gatcttgaaa cgaaaaaatg gaaaacggtt actaatatgt cgtcgttaaa atcagaagtt     900
agtacttgtg ttaacgatgg aaagttatat gtaataggag gattagaatt ttctatttca     960
acgggtgtgg cagaatattt gaaacacggc acttcgaaat ggataagact tccaaactta    1020
```

```
attactccta gatattcagg cgcgtcggta ttcgtaaacg atgatatata tgtaatgggt    1080 ggagttttata ccacgtatga aaatatgta gtattaaacg atgtggaatg tttcactaaa    1140
aatcgttgga taaaaaagtc tcccatgcct agacatcata gtatagttta tgctgtagag    1200
tacgacggcg acatctatgt aattactgga attactcacg agactcgtaa ttatctatac    1260
aaatatatag ttaaggaaga caatggata gaattgtaca tgtactttaa ccatgtagga    1320
aagatgttcg tgtgttcttg cggtgattat atcttaatta tagcagatgc aaaatacgaa    1380
tattatccaa atcaaatac ttggaatttg ttcgatatgt caactcgtaa tatcgaatat    1440
tatgatatgt ttactaaaga tgagactcca aagtgtaacg taactcataa gtcactgcca    1500
tcgtttttga gcaactgtga aaacaatttt ctacaatag                           1539
```

<210> SEQ ID NO 9
<211> LENGTH: 263
<212> TYPE: PRT
<213> ORGANISM: Human immunodeficiency virus

<400> SEQUENCE: 9

```
Met Lys Val Glu Ser Val Thr Phe Leu Thr Leu Leu Gly Ile Gly Cys
1               5                   10                  15

Val Leu Ser Cys Cys Thr Ile Pro Ser Arg Pro Ile Asn Met Lys Phe
                20                  25                  30

Lys Asn Ser Val Glu Thr Asp Ala Asn Ala Asn Tyr Asn Ile Gly Asp
            35                  40                  45

Thr Ile Glu Tyr Leu Cys Leu Pro Gly Tyr Arg Lys Gln Lys Met Gly
        50                  55                  60

Pro Ile Tyr Ala Lys Cys Thr Gly Thr Gly Trp Thr Leu Phe Asn Gln
65                  70                  75                  80

Cys Ile Lys Arg Arg Cys Pro Ser Pro Arg Asp Ile Asp Asn Gly Gln
                85                  90                  95

Leu Asp Ile Gly Gly Val Asp Phe Gly Ser Ser Ile Thr Tyr Ser Cys
            100                 105                 110

Asn Ser Gly Tyr His Leu Ile Gly Glu Ser Lys Ser Tyr Cys Glu Leu
        115                 120                 125

Gly Ser Thr Gly Ser Met Val Trp Asn Pro Glu Ala Pro Ile Cys Glu
    130                 135                 140

Ser Val Lys Cys Gln Ser Pro Pro Ser Ile Ser Asn Gly Arg His Asn
145                 150                 155                 160

Gly Tyr Glu Asp Phe Tyr Thr Asp Gly Ser Val Val Thr Tyr Ser Cys
                165                 170                 175

Asn Ser Gly Tyr Ser Leu Ile Gly Asn Ser Gly Val Leu Cys Ser Gly
            180                 185                 190

Gly Glu Trp Ser Asp Pro Pro Thr Cys Gln Ile Val Lys Cys Pro His
        195                 200                 205

Pro Thr Ile Ser Asn Gly Tyr Leu Ser Ser Gly Phe Lys Arg Ser Tyr
    210                 215                 220

Ser Tyr Asn Asp Asn Val Asp Phe Lys Cys Lys Tyr Gly Tyr Lys Leu
225                 230                 235                 240

Ser Gly Ser Ser Ser Thr Cys Ser Pro Gly Asn Thr Trp Lys Pro
                245                 250                 255

Glu Leu Pro Lys Cys Val Arg
            260
```

<210> SEQ ID NO 10

```
<211> LENGTH: 792
<212> TYPE: DNA
<213> ORGANISM: Human immunodeficiency virus

<400> SEQUENCE: 10
atgaaggtgg agagcgtgac gttcctgaca ttgttgggaa taggatgcgt tctatcatgc      60
tgtactattc cgtcacgacc cattaatatg aaatttaaga atagtgtgga gactgatgct     120
aatgctaatt acaacatagg agacactata gaatatctat gtctacctgg atacagaaag     180
caaaaatgg gacctatata tgctaaatgt acaggtactg gatggacact ctttaatcaa      240
tgtattaaac ggagatgccc atcgcctcga gatatcgata tggccaact tgatattggt      300
ggagtagact ttggctctag tataacgtac tcttgtaata gcggatatca tttgatcggt     360
gaatctaaat cgtattgtga attaggatct actggatcta tggtatggaa tcccgaggca     420
cctatttgtg aatctgttaa atgccaatcc cctccatcta tatccaacgg aagacataac     480
ggatacgagg attttatac cgatggaagc gttgtaactt atagttgcaa tagtggatat      540
cgttgattg gtaactctgg tgtcctgtgt tcaggaggag aatggtccga tccacccacg       600
tgtcagattg ttaaatgtcc acatcctaca atatcaaacg gatacttgtc tagcgggttt     660
aaaagatcat actcatacaa cgacaatgta gactttaagt gcaagtacgg atataaacta     720
tctggttcct catcatctac ttgctctcca ggaaatacat ggaagccgga acttccaaaa     780
tgtgtacgct aa                                                         792

<210> SEQ ID NO 11
<211> LENGTH: 316
<212> TYPE: PRT
<213> ORGANISM: Human immunodeficiency virus

<400> SEQUENCE: 11
```

Met Asp Thr Ile Lys Ile Phe Asn His Gly Glu Phe Asp Thr Ile Arg
1               5                   10                  15

Asn Glu Leu Val Asn Leu Leu Lys Val Val Lys Trp Asn Thr Ile Asn
            20                  25                  30

Ser Asn Val Thr Val Ser Ser Thr Asp Thr Ile Asp Ile Ser Asp Cys
        35                  40                  45

Ile Arg Glu Ile Leu Tyr Lys Gln Phe Lys Asn Val Arg Asn Ile Glu
    50                  55                  60

Val Ser Ser Asp Ile Ser Phe Ile Lys Tyr Asn Arg Phe Asn Asp Thr
65                  70                  75                  80

Thr Leu Thr Asp Asp Asn Val Gly Tyr Tyr Leu Val Ile Tyr Leu Asn
                85                  90                  95

Arg Thr Lys Ser Val Lys Thr Leu Ile Tyr Pro Thr Pro Glu Thr Val
            100                 105                 110

Ile Thr Ser Ser Glu Asp Ile Met Phe Ser Lys Ser Leu Asn Phe Arg
        115                 120                 125

Phe Glu Asn Val Lys Arg Asp Tyr Lys Leu Val Met Cys Ser Ile Ser
    130                 135                 140

Leu Thr Tyr Lys Pro Ser Ile Cys Arg Ile Gln Tyr Asp Asn Lys
145                 150                 155                 160

Tyr Leu Asp Ile Ser Asp Ser Gln Glu Cys Asn Ile Cys Tyr Cys
                165                 170                 175

Val Ile Thr Met Asp Pro His His Leu Ile Asp Leu Glu Thr Ile Cys
            180                 185                 190

Val Leu Val Asp Lys Ser Gly Lys Cys Leu Leu Val Asn Glu Phe Tyr

```
                195                 200                 205
Ile Arg Phe Arg Lys Asn His Ile Tyr Asn Ser Phe Ala Asp Leu Cys
    210                 215                 220

Met Asp His Ile Phe Glu Leu Pro Asn Thr Lys Glu Leu Phe Thr Leu
225                 230                 235                 240

Arg Asn Asp Asp Gly Arg Asn Ile Ala Trp Asp Asn Lys Leu Glu
                245                 250                 255

Ser Gly Asn Asn Thr Trp Ile Pro Lys Thr Asp Glu Tyr Lys Phe
            260                 265                 270

Leu Ser Lys Leu Met Asn Ile Ala Lys Phe Asn Asn Thr Lys Phe Asp
                275                 280                 285

Tyr Tyr Val Leu Val Gly Asp Thr Asp Pro Cys Thr Val Phe Thr Phe
    290                 295                 300

Lys Val Thr Lys Tyr Tyr Ile Asn Leu Asn Tyr Glu
305                 310                 315

<210> SEQ ID NO 12
<211> LENGTH: 951
<212> TYPE: DNA
<213> ORGANISM: Human immunodeficiency virus

<400> SEQUENCE: 12
atggatacta ttaaaatatt taatcatgga gagtttgata ctattagaaa tgaattggtc      60
aacttgttaa aagttgtaaa atggaacacc attaattcaa atgtaacggt atcgtctacc     120
gacacaatag atatatctga ttgtatcaga gagatattat acaaacagtt taaaaatgta     180
cgaaatatag aggtgagcag tgatatatct ttcataaaat ataatagatt taatgatact     240
actctaacag atgataatgt gggatattat ttagtgattt atttgaatcg gacgaaatct     300
gtaaagactt taatatatcc tactccagaa acagtgataa catcatccga ggatataatg     360
ttttctaaat ctcttaactt tagattcgag aatgtaaagc gcgactataa attggttatg     420
tgttctatat ctttgacata caagccatct atatgcagaa tccaatacga taacaataaa     480
tatttagata ttagcgacag tcaagaatgt aataatatat gttactgcgt cataactatg     540
gatccccacc acttgataga tttagaaacc atatgtgtct tggtcgataa atcaggaaag     600
tgtttgctag taaacgagtt ttatattaga tttaggaaaa atcacatcta caatagcttt     660
gccgatctat gcatggatca tatatttgaa ctaccgaata caaagaatt attcactctg      720 cgcaacgatg atggacgaaa catagcctgg ataatgata gttggaaag tggtaataat      780 acatggattc ctaaaacaga tgatgagtat aagtttctat ctaaattgat gaatattgcg     840
aagtttaaca acaccaaatt tgattactac gtgcttgttg gagatacgga tccgtgtact     900
gtctttacgt tcaaagtaac aaagtattac atcaatctca attatgaata g              951

<210> SEQ ID NO 13
<211> LENGTH: 204
<212> TYPE: PRT
<213> ORGANISM: Human immunodeficiency virus

<400> SEQUENCE: 13

Met Ala Tyr Met Asn Arg Ser Asp Leu Asp Lys Leu Lys His Glu Asn
1               5                   10                  15

Ile Phe Ser Gly Asn Ile Ile Glu Asp Ala Lys Glu Phe Val Phe Gly
            20                  25                  30

Ser Arg Lys Ile Tyr Thr Asp Ser Val Asp Asp Leu Ile Glu Leu Tyr
        35                  40                  45
```

Ser Leu Ala Lys Tyr Leu Asn Asn Glu Asn Leu Lys Asp Val Val Ile
        50                  55                  60

Glu Arg Met Asp Tyr Val Cys Lys Tyr Ile Gly Lys Asp Asn Trp Ser
 65                  70                  75                  80

Thr Ile Tyr Ser Phe Tyr Lys Glu Asn Gly Leu Arg Asn Ser Phe Leu
                85                  90                  95

Arg Gln Tyr Ile Asn Asn Ile Glu Glu Ile Cys Asn Thr Asp Gln
                100                 105                 110

Phe Leu Lys Leu Asp Val Asp Ser Val Cys Asp Ile Leu Asp Asn Asp
            115                 120                 125

Glu Ile Val Val Thr Arg Glu Tyr Thr Ile Leu Asn Met Val Leu Arg
        130                 135                 140

Trp Leu Glu Asn Lys Arg Val Asn Ile Asp Asp Phe Thr Lys Val Met
145                 150                 155                 160

Phe Val Ile Arg Phe Lys Phe Ile Thr Tyr Ser Glu Leu Thr Asn Ala
                165                 170                 175

Ile Glu Lys Ile Ala Pro Glu Tyr Arg Gln Cys Leu Gln Asp Leu Tyr
            180                 185                 190

His Met Lys Ile Thr Arg Pro Arg His Phe Asp Asn
        195                 200

<210> SEQ ID NO 14
<211> LENGTH: 615
<212> TYPE: DNA
<213> ORGANISM: Human immunodeficiency virus

<400> SEQUENCE: 14
atggcgtata tgaacagatc agatctcgat aaactaaaac acgaaaatat ctttctggg      60 aatattatag aggacgccaa agagttcgtc tttggatcta aaaaatata tactgattct     120 gttgatgatc taatagaatt atatagttta gccaaatatc ttaacaacga aaatcttaaa    180
gatgtagtga ttgagagaat ggattatgtg tgcaaatata tcggtaaaga taattggagt    240
actatatatt cgttttataa agaaaatggt ctacgtaata gttttctacg acaatacatc    300
aacaataata tagaagagat atgtaacaca gaccaatttc taaaattgga tgtagattca    360
gtatgtgata ttctagacaa cgatgagatc gtagtaacta gagaatatac tatcttaaac    420
atggtattac gatggctaga aaataaaaga gttaatatag cgactttac taaagttatg     480 ttcgttattc gatttaaatt tataacatat tctgaactca ctaatgcgat agagaaaata    540
gctccagaat acagacaatg cttacaggat ctataccata tgaaaattac gcgtcctaga    600
cactttgata actag                                                     615

<210> SEQ ID NO 15
<211> LENGTH: 151
<212> TYPE: PRT
<213> ORGANISM: Human immunodeficiency virus

<400> SEQUENCE: 15

Met Asn Ala Tyr Asn Lys Ala Asp Ser Phe Ser Leu Glu Ser Asp Ser
 1               5                  10                  15

Ile Lys Asp Val Ile His Asp Tyr Ile Cys Trp Leu Ser Met Thr Asp
            20                  25                  30

Glu Met Arg Pro Ser Ile Gly Asn Val Phe Lys Ala Met Glu Thr Phe
        35                  40                  45

Lys Ile Asp Ala Val Arg Tyr Tyr Asp Gly Asn Ile Tyr Asp Leu Ala

```
                50                  55                  60
Lys Asp Ile Asn Ala Met Ser Phe Asp Ser Phe Ile Arg Ser Leu Gln
 65                  70                  75                  80

Asn Ile Ser Ser Lys Lys Asp Lys Leu Thr Val Tyr Gly Thr Met Gly
                 85                  90                  95

Leu Leu Ser Ile Val Val Asp Ile Asn Lys Gly Cys Asp Ile Ser Asn
                100                 105                 110

Ile Lys Phe Ala Ala Gly Ile Ile Ile Leu Met Glu Tyr Ile Phe Asp
            115                 120                 125

Asp Thr Asp Met Ser His Leu Lys Val Ala Leu Tyr Arg Arg Ile Gln
        130                 135                 140

Arg Arg Asp Asp Val Asp Arg
145                 150

<210> SEQ ID NO 16
<211> LENGTH: 456
<212> TYPE: DNA
<213> ORGANISM: Human immunodeficiency virus

<400> SEQUENCE: 16
atgaatgcgt ataataaagc cgattcgttt tctttagagt ctgattctat caaagatgtt      60
atacacgatt atatttgttg gctcagtatg actgatgaaa tgagaccatc tatcggaaac     120
gtctttaaag cgatggaaac gtttaagata gacgcggtta gatattacga tggtaacata     180
tacgatttag ctaaagatat aaatgcgatg tcattcgaca gttttataag atctctacaa     240
aatatctctt caaagaaaga taaactcact gtttatggaa ccatgggact gctgtctatt     300
gtcgtagata ttaacaaagg ttgtgatata tccaatatca agttcgctgc cggaataatc     360
attttaatgg agtatatttt tgatgacacg gatatgtctc atcttaaagt agcactctat     420
cgtagaatac agagacgtga tgatgtagat agataa                               456

<210> SEQ ID NO 17
<211> LENGTH: 150
<212> TYPE: PRT
<213> ORGANISM: Human immunodeficiency virus

<400> SEQUENCE: 17

Met Gly Ile Gln His Glu Phe Asp Ile Ile Asn Gly Asp Ile Ala
 1               5                  10                  15

Leu Arg Asn Leu Gln Leu His Lys Gly Asp Asn Tyr Gly Cys Lys Leu
                 20                  25                  30

Lys Ile Ile Ser Asn Asp Tyr Lys Leu Lys Phe Arg Phe Ile Ile
             35                  40                  45

Arg Pro Asp Trp Ser Glu Ile Asp Glu Val Lys Gly Leu Thr Val Phe
         50                  55                  60

Ala Asn Asn Tyr Ala Val Lys Val Asn Lys Val Asp Asp Thr Phe Tyr
 65                  70                  75                  80

Tyr Val Ile Tyr Glu Ala Val Ile His Leu Tyr Asn Lys Lys Thr Glu
                 85                  90                  95

Ile Leu Ile Tyr Ser Asp Asp Glu Asn Glu Leu Phe Lys His Tyr Tyr
                100                 105                 110

Pro Tyr Ile Ser Leu Asn Met Ile Ser Lys Lys Tyr Lys Val Lys Glu
            115                 120                 125

Glu Asn Tyr Ser Ser Pro Tyr Ile Glu His Pro Leu Ile Pro Tyr Arg
        130                 135                 140
```

```
Asp Tyr Glu Ser Met Asp
145                 150

<210> SEQ ID NO 18
<211> LENGTH: 453
<212> TYPE: DNA
<213> ORGANISM: Human immunodeficiency virus

<400> SEQUENCE: 18
atgggtatac agcacgaatt cgacatcatt attaatggag atatcgcgtt gagaaattta      60
cagttacata aagggggataa ctacggatgc aaactaaaaa ttatttcgaa tgattacaag     120
aaattaaagt ttagattcat tatacgccca gattggtcgg aaatcgacga ggtcaaagga     180
ttaaccgtat ttgcaaacaa ctatgcggtg aaagttaata aggtagatga cacgttctat     240
tacgtaatat atgaggctgt aatacatctg tataacaaaa aaacagagat attgatttat     300
tctgatgatg agaacgagct cttcaaacac tattacccat acatcagtct aaatatgatt     360
agtaaaaagt ataagttaa agaagagaac tactcatccc cgtatataga acatccgtta     420
atcccgtata gagattatga gtccatggat taa                                   453

<210> SEQ ID NO 19
<211> LENGTH: 117
<212> TYPE: PRT
<213> ORGANISM: Human immunodeficiency virus

<400> SEQUENCE: 19

Met Arg Thr Leu Leu Ile Arg Tyr Ile Leu Trp Arg Asn Asp Asn Asp
1               5                   10                  15

Gln Thr Tyr Tyr Asn Asp Asp Phe Lys Lys Leu Met Leu Leu Asp Glu
            20                  25                  30

Leu Val Asp Asp Gly Asp Val Cys Thr Leu Ile Lys Asn Met Arg Met
        35                  40                  45

Thr Leu Ser Asp Gly Pro Leu Leu Asp Arg Leu Asn Gln Pro Val Asn
    50                  55                  60

Asn Ile Glu Asp Ala Lys Arg Met Ile Ala Ile Ser Ala Lys Val Ala
65                  70                  75                  80

Arg Asp Ile Gly Glu Arg Ser Glu Ile Arg Trp Glu Glu Ser Phe Thr
                85                  90                  95

Ile Leu Phe Arg Met Ile Glu Thr Tyr Phe Asp Leu Met Ile Asp
            100                 105                 110

Leu Tyr Gly Glu Lys
        115

<210> SEQ ID NO 20
<211> LENGTH: 354
<212> TYPE: DNA
<213> ORGANISM: Human immunodeficiency virus

<400> SEQUENCE: 20
atgaggactc tacttattag atatattctt tggagaaatg acaacgatca aacctattat      60
aatgatgatt ttaaaaagct tatgttgttg gatgaattgg tagatgacgg cgatgtatgt     120
acattgatta gaacatgag aatgacgctg tccgacggtc cattgctaga tagattgaat     180
caaccagtta ataatataga agacgctaag cgaatgatcg ctattagtgc caaagtggct     240
agagacattg gtgaacgttc agaaattaga tgggaagagt cattcaccat actctttagg     300
atgattgaaa catattttga tgatctaatg attgatctat atggtgaaaa ataa            354
```

<210> SEQ ID NO 21
<211> LENGTH: 175
<212> TYPE: PRT
<213> ORGANISM: Human immunodeficiency virus

<400> SEQUENCE: 21

Met Thr Ser Ser Ala Met Asp Asn Asn Glu Pro Lys Val Leu Glu Met
1               5                   10                  15

Val Tyr Asp Ala Thr Ile Leu Pro Glu Gly Ser Ser Met Asp Pro Asn
            20                  25                  30

Ile Met Asp Cys Ile Asn Arg His Ile Asn Met Cys Ile Gln Arg Thr
        35                  40                  45

Tyr Ser Ser Ser Ile Ile Ala Ile Leu Asn Arg Phe Leu Thr Met Asn
    50                  55                  60

Lys Asp Glu Leu Asn Asn Thr Gln Cys His Ile Ile Lys Glu Phe Met
65                  70                  75                  80

Thr Tyr Glu Gln Met Ala Ile Asp His Tyr Gly Glu Tyr Val Asn Ala
                85                  90                  95

Ile Leu Tyr Gln Ile Arg Lys Arg Pro Asn Gln His His Thr Ile Asp
            100                 105                 110

Leu Phe Lys Lys Ile Lys Arg Thr Pro Tyr Asp Thr Phe Lys Val Asp
        115                 120                 125

Pro Val Glu Phe Val Lys Lys Val Ile Gly Phe Val Ser Ile Leu Asn
    130                 135                 140

Lys Tyr Lys Pro Val Tyr Ser Tyr Val Leu Tyr Glu Asn Val Leu Tyr
145                 150                 155                 160

Asp Glu Phe Lys Cys Phe Ile Asn Tyr Val Glu Thr Lys Tyr Phe
                165                 170                 175

<210> SEQ ID NO 22
<211> LENGTH: 528
<212> TYPE: DNA
<213> ORGANISM: Human immunodeficiency virus

<400> SEQUENCE: 22
atgacgtcct ctgcaatgga taacaatgaa cctaaagtac tagaaatggt atatgatgct        60
acaattttac ccgaaggtag tagcatggat ccaaatatca tggattgtat aaacagacac       120
atcaatatgt gtatacaacg cacctatagt tctagtataa ttgccatttt gaatagattc       180
ctaacaatga caaggatga actaaacaat acacagtgtc atataattaa agaatttatg        240
acatacgaac aaatggcgat tgaccattat ggagaatatg taaacgctat tctatatcaa       300
attcgtaaaa gacctaatca acatcacacc attgatctgt ttaaaaaaat aaaaagaacc       360
ccgtatgaca cttttaaagt ggatcccgta gaattcgtaa aaaagttat cggatttgta        420 tctatcttga caaatataa accggtttat agttacgtcc tgtacgagaa cgtcctgtac        480
gatgagttca atgtttcat taactacgtg gaaactaagt atttctaa                     528

<210> SEQ ID NO 23
<211> LENGTH: 472
<212> TYPE: PRT
<213> ORGANISM: Human immunodeficiency virus

<400> SEQUENCE: 23

Met Ile Phe Val Ile Glu Ser Lys Leu Leu Gln Ile Tyr Arg Asn Arg
1               5                   10                  15

Asn Arg Asn Ile Asn Phe Tyr Thr Thr Met Asp Asn Ile Met Ser Ala

```
                 20                  25                  30
Glu Tyr Tyr Leu Ser Leu Tyr Ala Lys Tyr Asn Ser Lys Asn Leu Asp
             35                  40                  45

Val Phe Arg Asn Met Leu Gln Ala Ile Glu Pro Ser Gly Asn Asn Tyr
 50                  55                  60

His Ile Leu His Ala Tyr Cys Gly Ile Lys Gly Leu Asp Glu Arg Phe
 65                  70                  75                  80

Val Glu Glu Leu Leu His Arg Gly Tyr Ser Pro Asn Glu Thr Asp Asp
                 85                  90                  95

Asp Gly Asn Tyr Pro Leu His Ile Ala Ser Lys Ile Asn Asn Asn Arg
             100                 105                 110

Ile Val Ala Met Leu Leu Thr His Gly Ala Asp Pro Asn Ala Cys Asp
             115                 120                 125

Lys His Asn Lys Thr Pro Leu Tyr Tyr Leu Ser Gly Thr Asp Asp Glu
             130                 135                 140

Val Ile Glu Arg Ile Asn Leu Leu Val Gln Tyr Gly Ala Lys Ile Asn
145                 150                 155                 160

Asn Ser Val Asp Glu Glu Gly Cys Gly Pro Leu Leu Ala Cys Thr Asp
                 165                 170                 175

Pro Ser Glu Arg Val Phe Lys Lys Ile Met Ser Ile Gly Phe Glu Ala
             180                 185                 190

Arg Ile Val Asp Lys Phe Gly Lys Asn His Ile His Arg His Leu Met
             195                 200                 205

Ser Asp Asn Pro Lys Ala Ser Thr Ile Ser Trp Met Met Lys Leu Gly
             210                 215                 220

Ile Ser Pro Ser Lys Pro Asp His Asp Gly Asn Thr Pro Leu His Ile
225                 230                 235                 240

Val Cys Ser Lys Thr Val Lys Asn Val Asp Ile Asp Leu Leu Leu
                 245                 250                 255

Pro Ser Thr Asp Val Asn Lys Gln Asn Lys Phe Gly Asp Ser Pro Leu
             260                 265                 270

Thr Leu Leu Ile Lys Thr Leu Ser Pro Ala His Leu Ile Asn Lys Leu
             275                 280                 285

Leu Ser Thr Ser Asn Val Ile Thr Asp Gln Thr Val Asn Ile Cys Ile
             290                 295                 300

Phe Tyr Asp Arg Asp Asp Val Leu Glu Ile Ile Asn Lys Gly Lys
305                 310                 315                 320

Gln Tyr Asp Ser Thr Asp Phe Lys Met Ala Val Glu Val Gly Ser Ile
                 325                 330                 335

Arg Cys Val Lys Tyr Leu Leu Asp Asn Asp Ile Ile Cys Glu Asp Ala
             340                 345                 350

Met Tyr Ala Val Leu Ser Glu Tyr Glu Thr Met Val Asp Tyr Leu
             355                 360                 365

Leu Phe Asn His Phe Ser Val Asp Ser Val Val Asn Gly His Thr Cys
             370                 375                 380

Met Ser Glu Cys Val Arg Leu Asn Asn Pro Val Ile Leu Ser Lys Leu
385                 390                 395                 400

Met Leu His Asn Pro Thr Ser Glu Thr Met Tyr Leu Thr Met Lys Ala
                 405                 410                 415

Ile Glu Lys Asp Lys Leu Asp Lys Ser Ile Ile Pro Phe Ile Ala
             420                 425                 430

Tyr Phe Val Leu Met His Pro Asp Phe Cys Lys Asn Arg Arg Tyr Phe
             435                 440                 445
```

Thr Ser Tyr Lys Arg Phe Val Thr Asp Tyr Val His Glu Gly Val Ser
    450                 455                 460

Tyr Glu Val Phe Asp Asp Tyr Phe
465                 470

<210> SEQ ID NO 24
<211> LENGTH: 1419
<212> TYPE: DNA
<213> ORGANISM: Human immunodeficiency virus

<400> SEQUENCE: 24
atgatatttg ttatagagag taaattgttg caaatataca gaaatagaaa tagaaatatt      60
aatttttata ctacaatgga caacattatg tcggccgagt attatctatc tctttatgcc     120
aaatataata gtaaaaattt agatgtattt aggaatatgc tacaagctat cgaaccttct     180
ggaaataatt atcacattct acatgcgtat tgtggaatta aggactaga tgaacgattt      240 gtcgaagaac ttcttcatag aggatactct ccaaatgaga cggatgatga tggaaattat     300
ccattgcata tagcttctaa aattaataat aatagaatag tcgcgatgct gctgacgcac     360
ggcgcagatc caaacgcgtg tgataaacat aataaaacac ctctatatta tctctcggga     420
acagatgatg aagtcataga gaataaaat ttattggtac agtatggagc caagattaac      480
aactcggttg atgaagaagg atgtggtccg ttgttggcgt gtacagatcc ttcagaaaga     540
gtgtttaaaa aaataatgtc catcggattc gaagccagga tagtggataa atttggcaaa     600
aatcatattc atagacatct tatgtcagac aatccaaaag cttctacaat ctcatggatg     660
atgaaactag aattagtcc ctcaaaacca gatcatgatg gaaatacacc tctccatatt      720
gtatgctcta aaacagtcaa gaatgtgac attatagatc ttttacttcc atcaacggat     780
gttaataaac aaaacaaatt cggagatagt cctcttacac ttcttattaa gacattgagc     840
ccagcgcatc ttattaacaa attgctatcg actagcaatg ttattacgga tcaaacagtt     900
aatatttgta tcttttatga tagagatgat gttctagaaa ttattaatga taaaggaaag     960
caatatgatt ctaccgattt taagatggct gttgaagtgg gatccataag atgcgtcaaa    1020
tatctattag acaatgatat aatttgtgaa gatgctatgt actacgctgt actatctgaa    1080
tacgaaacaa tggtagacta tctattgttc aatcatttta gtgtagactc tgtagttaac    1140
ggtcatacat gtatgagcga atgtgtaaga ctaaataacc cagtcatttt atcgaagctg    1200
atgttacata tcctacttc tgagaccatg tatctaacta tgaaagctat agaaaaagat    1260
aaactagata atctctattat tattccgttt atcgcgtact ttgtacttat gcatccggac    1320
ttttgtaaaa atcgtagata ctttacttca tataaacgtt ttgtaactga ttatgttcat    1380
gaaggagtat cttacgaagt attcgatgat tatttttaa                           1419

<210> SEQ ID NO 25
<211> LENGTH: 220
<212> TYPE: PRT
<213> ORGANISM: Human immunodeficiency virus

<400> SEQUENCE: 25

Met Val Tyr Lys Leu Val Leu Leu Phe Cys Ile Ala Ser Leu Gly Tyr
1               5                   10                  15

Ser Val Glu Tyr Lys Asn Thr Ile Cys Pro Pro Arg Gln Asp Tyr Arg
            20                  25                  30

Tyr Trp Tyr Phe Ala Ala Glu Leu Thr Ile Gly Val Asn Tyr Asp Ile
        35                  40                  45

Asn Ser Thr Ile Ile Gly Glu Cys His Met Ser Glu Ser Tyr Ile Asp
 50                  55                  60

Arg Asn Ala Asn Ile Val Leu Thr Gly Tyr Gly Leu Glu Ile Asn Met
 65                  70                  75                  80

Thr Ile Met Asp Thr Asp Gln Arg Phe Val Ala Ala Glu Gly Val
                 85                  90                  95

Gly Lys Asp Asn Lys Leu Ser Val Leu Leu Phe Thr Thr Gln Arg Leu
                100                 105                 110

Asp Lys Val His His Asn Ile Ser Val Thr Ile Thr Cys Met Glu Met
                115                 120                 125

Asn Cys Gly Thr Thr Lys Tyr Asp Ser Asp Leu Pro Glu Ser Ile His
    130                 135                 140

Lys Ser Ser Cys Asp Ile Thr Ile Asn Gly Ser Cys Val Thr Cys
145                 150                 155                 160

Val Asn Leu Glu Thr Asp Pro Thr Lys Ile Asn Pro His Tyr Leu His
                165                 170                 175

Pro Lys Asp Lys Tyr Leu Tyr His Asn Ser Glu Tyr Gly Met Arg Gly
                180                 185                 190

Ser Tyr Gly Val Thr Phe Ile Asp Glu Leu Asn Gln Cys Leu Leu Asp
                195                 200                 205

Ile Lys Glu Leu Ser Tyr Asp Ile Cys Tyr Arg Glu
    210                 215                 220

<210> SEQ ID NO 26
<211> LENGTH: 663
<212> TYPE: DNA
<213> ORGANISM: Human immunodeficiency virus

<400> SEQUENCE: 26
atggtttaca aattagtctt gctcttttgt atcgcatctc tcgggtattc ggtagaatac      60
aagaatacta tatgtcctcc tcgacaagat taccggtatt ggtactttgc cgccgaactc     120
actattggtg taaattacga cattaattct actattattg gtgagtgtca tatgagtgaa     180
agctatatcg acagaaatgc taacatagtg ttgactggat acggactaga aataaacatg     240
accatcatgg atacggatca gagatttgtg gcagcggctg agggtgttgg taaagataat     300
aaactatctg ttctgttgtt taccactcag cggctagata agttcatca taatattagt      360 gtgacaataa catgtatgga aatgaattgt ggaaccacaa aatacgatag cgatcttccg     420
gaatcaattc ataaatcatc atcgtgtgat ataactataa atggatcatg tgtgacatgt     480
gttaacttag agactgatcc aacaaagatt aatccccatt acctacaccc caaggataaa     540
tatctttatc ataattctga gtatggcatg cgtggtagtt atggcgtgac atttatagat     600
gaactaaacc agtgccttct tgacataaaa gaactaagtt atgatatttg ttatagagag     660
taa                                                                    663

<210> SEQ ID NO 27
<211> LENGTH: 284
<212> TYPE: PRT
<213> ORGANISM: Human immunodeficiency virus

<400> SEQUENCE: 27

Met Asp Leu Ser Arg Ile Asn Thr Trp Lys Ser Lys Gln Leu Lys Ser
1               5                   10                  15

Phe Leu Ser Ser Lys Asp Thr Phe Lys Ala Asp Val His Gly His Ser
                20                  25                  30

```
Ala Leu Tyr Tyr Ala Ile Ala Asp Asn Asn Val Arg Leu Val Cys Thr
                35                  40                  45

Leu Leu Asn Ala Gly Ala Leu Lys Asn Leu Leu Glu Asn Glu Phe Pro
 50                  55                  60

Leu His Gln Ala Ala Thr Leu Glu Asp Thr Lys Ile Val Lys Ile Leu
 65                  70                  75                  80

Leu Phe Ser Gly Met Asp Asp Ser Gln Phe Asp Asp Lys Gly Asn Thr
                85                  90                  95

Ala Leu Tyr Tyr Ala Val Asp Ser Gly Asn Met Gln Thr Val Lys Leu
                100                 105                 110

Phe Val Lys Lys Asn Trp Arg Leu Met Phe Tyr Gly Lys Thr Gly Trp
                115                 120                 125

Lys Thr Ser Phe Tyr His Ala Val Met Leu Asn Asp Val Ser Ile Val
                130                 135                 140

Ser Tyr Phe Leu Ser Glu Ile Pro Ser Thr Phe Asp Leu Ala Ile Leu
145                 150                 155                 160

Leu Ser Cys Ile His Thr Thr Ile Lys Asn Gly His Val Asp Met Met
                165                 170                 175

Ile Leu Leu Leu Asp Tyr Met Thr Ser Thr Asn Thr Asn Asn Ser Leu
                180                 185                 190

Leu Phe Ile Pro Asp Ile Lys Leu Ala Ile Asp Asn Lys Asp Ile Glu
                195                 200                 205

Met Leu Gln Ala Leu Phe Lys Tyr Asp Ile Asn Ile Tyr Ser Val Asn
210                 215                 220

Leu Glu Asn Val Leu Leu Asp Asp Ala Glu Ile Thr Lys Met Ile Ile
225                 230                 235                 240

Glu Lys His Val Glu Tyr Lys Ser Asp Ser Tyr Thr Lys Asp Leu Asp
                245                 250                 255

Ile Val Lys Asn Asn Lys Leu Asp Glu Ile Ile Ser Lys Asn Lys Glu
                260                 265                 270

Leu Arg Leu Met Tyr Val Asn Cys Val Lys Lys Asn
                275                 280

<210> SEQ ID NO 28
<211> LENGTH: 855
<212> TYPE: DNA
<213> ORGANISM: Human immunodeficiency virus

<400> SEQUENCE: 28
atggatctgt cacgaattaa tacttggaag tctaagcagc tgaaaagctt tctctctagt      60
aaagatacat ttaaggcgga tgtccatgga catagtgcct tgtattatgc aatagctgat     120
aataacgtgc gtctagtatg tacgttgttg aacgctggag cattgaaaaa tcttctagag     180
aatgaatttc cattacatca ggcagccaca ttagaagata ccaaaatagt aaagattttg     240
ctattcagtg gaatggatga ttcacaattt gatgacaaag gaacaccgc attgtattat     300 gcggttgata gtggtaacat gcaaacggtg aaactgtttg ttaagaaaaa ttggagactg     360
atgttctatg gaaaaactgg atggaaaact tcatttatc atgccgtcat gcttaatgat     420
gtaagtattg tatcatactt tctttcagaa ataccatcta cttttgatct ggctattctc     480
cttagttgta ttcacaccac tataaaaaat ggacacgtgg atatgatgat tcttcttgctc    540 gactatatga cgtcgacaaa caccaataat tcccttctct tcattccgga cattaaattg     600
gctatagata taaagacat tgagatgtta caggctctgt tcaaatacga cattaatatc      660
```

```
tactctgtta atctggaaaa tgtactattg gatgatgccg aaataactaa gatgattata      720
gaaaagcatg ttgaatacaa gtctgactcc tatacaaaag atctcgatat cgtcaagaat      780
aataaattgg atgaaataat tagcaaaaac aaggaactca gactcatgta cgtcaattgt      840
gtaaagaaaa actaa                                                       855
```

<210> SEQ ID NO 29
<211> LENGTH: 259
<212> TYPE: PRT
<213> ORGANISM: Human immunodeficiency virus

<400> SEQUENCE: 29

```
Met Ala His Asn Arg Phe Tyr Ser Glu Ile Leu Pro Lys Gln Gly Asp
1               5                   10                  15

Val Thr Met Cys Arg Val Leu Ser Gln Ser Asp Ser Trp Asp Glu Gly
            20                  25                  30

Val Tyr Val Ser Met Met Glu Tyr Gly Asn Val Glu Gly Tyr Val Ala
        35                  40                  45

Ile Gly Val Glu Asn His Arg Asp Ile Arg Lys Phe Arg Lys Leu
    50                  55                  60

Ala Pro Gly Ala Glu Met Cys Met Thr Val Leu Arg Val Asp Arg Glu
65                  70                  75                  80

Lys Gly Tyr Val Asp Leu Asp Asp Arg Ala Val Asn Ala Asn Gln Ala
                85                  90                  95

Tyr Glu Cys Cys Ser Arg Tyr Gln Leu Arg Arg Thr Glu Met Ala Val
            100                 105                 110

Ala Glu Arg Ala Ala Glu Tyr Ala Gly Val Lys Gly Ser Ala Val Tyr
        115                 120                 125

Asp Phe Leu Asp Glu Thr Val Arg Ala Leu Ile Pro Gly Ser Leu Met
    130                 135                 140

Ser Gly Thr Lys Gly Leu Lys Ile Ser Ser Asp Leu Lys Gln Leu Leu
145                 150                 155                 160

Lys Glu Phe Gly Ala Glu Val Gly Leu Asp Arg Ala Gly Arg Ala Glu
                165                 170                 175

Ala Val Val Arg Val Pro Gly Ala Phe Phe Gly His Val Leu Arg Gly
            180                 185                 190

Val Thr Asn Ala Tyr Asp Ala Met Lys Glu Met Lys Pro Asp Ser Gly
        195                 200                 205

Val Asn Val Ala Val Tyr Pro Pro Glu Arg Gly Val Val Ala Val Thr
    210                 215                 220

Val Met Ala Gly Asp Ser Glu Ala Ala Tyr Trp Gly Leu His Ala Val
225                 230                 235                 240

Leu Phe Lys Val Arg Glu Val Val Lys Ala Ala Gly Gly Gly Leu Cys
                245                 250                 255

Pro Phe Val
```

<210> SEQ ID NO 30
<211> LENGTH: 777
<212> TYPE: DNA
<213> ORGANISM: Human immunodeficiency virus

<400> SEQUENCE: 30

```
atggcacaca acaggtttta cagcgagata ctcccaaaac aaggagacgt tacaatgtgc       60
agagtcttgt ctcagtcaga ctcttgggac gaaggcgttt acgtgtctat gatggagtac      120
ggaaacgtag agggttacgt ggcaatcggc gttgaaaacc acaggacat cagaaagagg       180
```

```
ttcaggaaac ttgccccagg cgctgaaatg tgcatgacgg tcctcagggt agaccgcgaa    240
aagggctacg tggatttgga cgacagggcc gtgaatgcca atcaggcgta cgagtgttgc    300
tccaggtacc agctgaggag gacggagatg gcggtcgcag agagggcggc agagtacgct    360
ggagtaaagg gatctgcagt ctatgacttt ttggacgaaa ccgtgagggc cctgataccc    420
ggctccctga tgtctggaac gaaaggtcta aaaatctctt ccgacctgaa gcagctccta    480
aaagagtttg gagcagaggt cggccttgac agaccggtc gggccgaggc tgtcgtgaga    540
gttcccggcg ccttctttgg gcacgtcctg aggggtgtga cgaatgccta cgacgcaatg    600
aaggagatga agccagactc tggggtgaat gtggccgttt accctcccga acgcggggtt    660
gtggctgtga ctgtgatggc cggcgactct gaggcggcgt actggggact gcacgccgtg    720
ctgtttaagg tgcgagaggt cgtaaaggcg gccgggggag gactgtgccc ctttgtg      777
```

<210> SEQ ID NO 31
<211> LENGTH: 15
<212> TYPE: PRT
<213> ORGANISM: Human immunodeficiency virus

<400> SEQUENCE: 31

Val Gly Asn Leu Trp Val Thr Val Tyr Tyr Gly Val Pro Val Trp
1               5                   10                  15

<210> SEQ ID NO 32
<211> LENGTH: 15
<212> TYPE: PRT
<213> ORGANISM: Human immunodeficiency virus

<400> SEQUENCE: 32

Trp Val Thr Val Tyr Tyr Gly Val Pro Val Trp Lys Gly Ala Thr
1               5                   10                  15

<210> SEQ ID NO 33
<211> LENGTH: 15
<212> TYPE: PRT
<213> ORGANISM: Human immunodeficiency virus

<400> SEQUENCE: 33

Gly Ala Thr Thr Thr Leu Phe Cys Ala Ser Asp Ala Lys Ala Tyr
1               5                   10                  15

<210> SEQ ID NO 34
<211> LENGTH: 15
<212> TYPE: PRT
<213> ORGANISM: Human immunodeficiency virus

<400> SEQUENCE: 34

Thr Thr Leu Phe Cys Ala Ser Asp Ala Lys Ala Tyr Asp Thr Glu
1               5                   10                  15

<210> SEQ ID NO 35
<211> LENGTH: 15
<212> TYPE: PRT
<213> ORGANISM: Human immunodeficiency virus

<400> SEQUENCE: 35

Thr His Ala Cys Val Pro Ala Asp Pro Asn Pro Gln Glu Met Val
1               5                   10                  15

<210> SEQ ID NO 36
<211> LENGTH: 15

-continued

```
<212> TYPE: PRT
<213> ORGANISM: Human immunodeficiency virus

<400> SEQUENCE: 36

Glu Asn Val Thr Glu Asn Phe Asn Met Trp Lys Asn Glu Met Val
1               5                   10                  15

<210> SEQ ID NO 37
<211> LENGTH: 15
<212> TYPE: PRT
<213> ORGANISM: Human immunodeficiency virus

<400> SEQUENCE: 37

Glu Asn Phe Asn Met Trp Lys Asn Glu Met Val Asn Gln Met Gln
1               5                   10                  15

<210> SEQ ID NO 38
<211> LENGTH: 15
<212> TYPE: PRT
<213> ORGANISM: Human immunodeficiency virus

<400> SEQUENCE: 38

Glu Met Val Asn Gln Met Gln Glu Asp Val Ile Ser Leu Trp Asp
1               5                   10                  15

<210> SEQ ID NO 39
<211> LENGTH: 15
<212> TYPE: PRT
<213> ORGANISM: Human immunodeficiency virus

<400> SEQUENCE: 39

Cys Val Lys Leu Thr Pro Leu Cys Val Thr Leu Glu Cys Arg Asn
1               5                   10                  15

<210> SEQ ID NO 40
<211> LENGTH: 15
<212> TYPE: PRT
<213> ORGANISM: Human immunodeficiency virus

<400> SEQUENCE: 40

Asn Cys Ser Phe Asn Ala Thr Thr Val Val Arg Asp Arg Lys Gln
1               5                   10                  15

<210> SEQ ID NO 41
<211> LENGTH: 15
<212> TYPE: PRT
<213> ORGANISM: Human immunodeficiency virus

<400> SEQUENCE: 41

Asn Ala Thr Thr Val Val Arg Asp Arg Lys Gln Thr Val Tyr Ala
1               5                   10                  15

<210> SEQ ID NO 42
<211> LENGTH: 15
<212> TYPE: PRT
<213> ORGANISM: Human immunodeficiency virus

<400> SEQUENCE: 42

Val Tyr Ala Leu Phe Tyr Arg Leu Asp Ile Val Pro Leu Thr Lys
1               5                   10                  15

<210> SEQ ID NO 43
<211> LENGTH: 15
<212> TYPE: PRT
<213> ORGANISM: Human immunodeficiency virus
```

<400> SEQUENCE: 43

Phe Tyr Arg Leu Asp Ile Val Pro Leu Thr Lys Lys Asn Tyr Ser
1               5                   10                  15

<210> SEQ ID NO 44
<211> LENGTH: 15
<212> TYPE: PRT
<213> ORGANISM: Human immunodeficiency virus

<400> SEQUENCE: 44

Ile Asn Cys Asn Thr Ser Ala Ile Thr Gln Ala Cys Pro Lys Val
1               5                   10                  15

<210> SEQ ID NO 45
<211> LENGTH: 15
<212> TYPE: PRT
<213> ORGANISM: Human immunodeficiency virus

<400> SEQUENCE: 45

Pro Lys Val Thr Phe Asp Pro Ile Pro Ile His Tyr Cys Thr Pro
1               5                   10                  15

<210> SEQ ID NO 46
<211> LENGTH: 15
<212> TYPE: PRT
<213> ORGANISM: Human immunodeficiency virus

<400> SEQUENCE: 46

Phe Asp Pro Ile Pro Ile His Tyr Cys Thr Pro Ala Gly Tyr Ala
1               5                   10                  15

<210> SEQ ID NO 47
<211> LENGTH: 15
<212> TYPE: PRT
<213> ORGANISM: Human immunodeficiency virus

<400> SEQUENCE: 47

Thr Gly Asp Ile Ile Gly Asp Ile Arg Gln Ala His Cys Asn Ile
1               5                   10                  15

<210> SEQ ID NO 48
<211> LENGTH: 15
<212> TYPE: PRT
<213> ORGANISM: Human immunodeficiency virus

<400> SEQUENCE: 48

Ser Ser Ser Ile Ile Thr Ile Pro Cys Arg Ile Lys Gln Ile Ile
1               5                   10                  15

<210> SEQ ID NO 49
<211> LENGTH: 15
<212> TYPE: PRT
<213> ORGANISM: Human immunodeficiency virus

<400> SEQUENCE: 49

Ile Thr Ile Pro Cys Arg Ile Lys Gln Ile Ile Asn Met Trp Gln
1               5                   10                  15

<210> SEQ ID NO 50
<211> LENGTH: 15
<212> TYPE: PRT
<213> ORGANISM: Human immunodeficiency virus

<400> SEQUENCE: 50

```
Cys Arg Ile Lys Gln Ile Ile Asn Met Trp Gln Glu Val Gly Arg
1               5                   10                  15
```

<210> SEQ ID NO 51
<211> LENGTH: 15
<212> TYPE: PRT
<213> ORGANISM: Human immunodeficiency virus

<400> SEQUENCE: 51

```
Val Gly Arg Ala Met Tyr Ala Pro Pro Ile Lys Gly Asn Ile Thr
1               5                   10                  15
```

<210> SEQ ID NO 52
<211> LENGTH: 15
<212> TYPE: PRT
<213> ORGANISM: Human immunodeficiency virus

<400> SEQUENCE: 52

```
Met Tyr Ala Pro Pro Ile Lys Gly Asn Ile Thr Cys Lys Ser Asn
1               5                   10                  15
```

<210> SEQ ID NO 53
<211> LENGTH: 15
<212> TYPE: PRT
<213> ORGANISM: Human immunodeficiency virus

<400> SEQUENCE: 53

```
Pro Ile Lys Gly Asn Ile Thr Cys Lys Ser Asn Ile Thr Gly Leu
1               5                   10                  15
```

<210> SEQ ID NO 54
<211> LENGTH: 15
<212> TYPE: PRT
<213> ORGANISM: Human immunodeficiency virus

<400> SEQUENCE: 54

```
Glu Thr Phe Arg Pro Gly Gly Gly Asp Met Arg Asn Asn Trp Arg
1               5                   10                  15
```

<210> SEQ ID NO 55
<211> LENGTH: 15
<212> TYPE: PRT
<213> ORGANISM: Human immunodeficiency virus

<400> SEQUENCE: 55

```
Glu Leu Tyr Lys Tyr Lys Val Val Glu Ile Lys Pro Leu Gly Val
1               5                   10                  15
```

<210> SEQ ID NO 56
<211> LENGTH: 15
<212> TYPE: PRT
<213> ORGANISM: Human immunodeficiency virus

<400> SEQUENCE: 56

```
Tyr Lys Val Val Glu Ile Lys Pro Leu Gly Val Ala Pro Thr Thr
1               5                   10                  15
```

<210> SEQ ID NO 57
<211> LENGTH: 15
<212> TYPE: PRT
<213> ORGANISM: Human immunodeficiency virus

<400> SEQUENCE: 57

```
Glu Ile Lys Pro Leu Gly Val Ala Pro Thr Thr Thr Lys Arg Arg
```

<210> SEQ ID NO 58
<211> LENGTH: 15
<212> TYPE: PRT
<213> ORGANISM: Human immunodeficiency virus

<400> SEQUENCE: 58

Leu Gly Val Ala Pro Thr Thr Thr Lys Arg Arg Val Val Glu Arg
1               5                   10                  15

<210> SEQ ID NO 59
<211> LENGTH: 9
<212> TYPE: PRT
<213> ORGANISM: Human immunodeficiency virus

<400> SEQUENCE: 59

Tyr Ser Glu Asn Ser Ser Glu Tyr Tyr
1               5

<210> SEQ ID NO 60
<211> LENGTH: 39
<212> TYPE: DNA
<213> ORGANISM: Vaccinia virus

<400> SEQUENCE: 60
aaaattgaaa ttttattttt ttttttttgga atataaata                                 39

<210> SEQ ID NO 61
<211> LENGTH: 14
<212> TYPE: DNA
<213> ORGANISM: Vaccinia virus

<400> SEQUENCE: 61 ccggaattttt tatt                                                            14

<210> SEQ ID NO 62
<211> LENGTH: 14
<212> TYPE: DNA
<213> ORGANISM: Vaccinia virus

<400> SEQUENCE: 62
ttaaaaataa ggcc                                                             14

<210> SEQ ID NO 63
<211> LENGTH: 44
<212> TYPE: DNA
<213> ORGANISM: Vaccinia virus

<400> SEQUENCE: 63
ttgaattctc gagcatggac agggccaagc tgctgctgct gctg                            44

<210> SEQ ID NO 64
<211> LENGTH: 28
<212> TYPE: DNA
<213> ORGANISM: Vaccinia virus

<400> SEQUENCE: 64
tgctgctcac gttcctgcac tccagggt                                              28

<210> SEQ ID NO 65
<211> LENGTH: 37
<212> TYPE: DNA
<213> ORGANISM: Vaccinia virus

<400> SEQUENCE: 65
tttctcgagc atggccgcca gggccagcat cctgagg                                37

<210> SEQ ID NO 66
<211> LENGTH: 26
<212> TYPE: DNA
<213> ORGANISM: Vaccinia virus

<400> SEQUENCE: 66
atctgctcct gcaggttgct ggtggt                                            26

<210> SEQ ID NO 67
<211> LENGTH: 24
<212> TYPE: DNA
<213> ORGANISM: Vaccinia virus

<400> SEQUENCE: 67
gaactaggat cctaactcga gaaa                                              24

<210> SEQ ID NO 68
<211> LENGTH: 25
<212> TYPE: DNA
<213> ORGANISM: Vaccinia virus

<400> SEQUENCE: 68
attagtatgc atttatttat ttagg                                             25

<210> SEQ ID NO 69
<211> LENGTH: 23
<212> TYPE: DNA
<213> ORGANISM: Vaccinia virus

<400> SEQUENCE: 69
cgttggtcta gagagaaaaa ttg                                               23

<210> SEQ ID NO 70
<211> LENGTH: 22
<212> TYPE: DNA
<213> ORGANISM: Vaccinia virus

<400> SEQUENCE: 70
ctatagaatt ctcaagctat gc                                                22

<210> SEQ ID NO 71
<211> LENGTH: 31
<212> TYPE: DNA
<213> ORGANISM: Vaccinia virus

<400> SEQUENCE: 71 tttttttgacg tcattgactc gtctactatt c                                     31

<210> SEQ ID NO 72
<211> LENGTH: 31
<212> TYPE: DNA
<213> ORGANISM: Vaccinia virus

<400> SEQUENCE: 72 ttttttttcta gatggtgttg tttgttattt g                                     31

<210> SEQ ID NO 73
<211> LENGTH: 31
<212> TYPE: DNA

-continued

<213> ORGANISM: Vaccinia virus

<400> SEQUENCE: 73 tttttgaat tcattgactc gtctactatt c 31

<210> SEQ ID NO 74
<211> LENGTH: 31
<212> TYPE: DNA
<213> ORGANISM: Vaccinia virus

<400> SEQUENCE: 74
ttttttatcg attggtgttg tttgttattt g 31

<210> SEQ ID NO 75
<211> LENGTH: 32
<212> TYPE: DNA
<213> ORGANISM: Vaccinia virus

<400> SEQUENCE: 75
ttttttatcg atctaatttt tattaatgat ac 32

<210> SEQ ID NO 76
<211> LENGTH: 30
<212> TYPE: DNA
<213> ORGANISM: Vaccinia virus

<400> SEQUENCE: 76
ttttttggat ccaaacagcg gacacattgc 30

<210> SEQ ID NO 77
<211> LENGTH: 31
<212> TYPE: DNA
<213> ORGANISM: Vaccinia virus

<400> SEQUENCE: 77
ttttttgacg tcgagaaagt taagaagata c 31

<210> SEQ ID NO 78
<211> LENGTH: 32
<212> TYPE: DNA
<213> ORGANISM: Vaccinia virus

<400> SEQUENCE: 78
tttttttcta gatctttatt atacggcact aa 32

<210> SEQ ID NO 79
<211> LENGTH: 31
<212> TYPE: DNA
<213> ORGANISM: Vaccinia virus

<400> SEQUENCE: 79
ttttttgaat tcgagaaagt taagaagata c 31

<210> SEQ ID NO 80
<211> LENGTH: 32
<212> TYPE: DNA
<213> ORGANISM: Vaccinia virus

<400> SEQUENCE: 80
ttttttatcg attctttatt atacggcact aa 32

<210> SEQ ID NO 81
<211> LENGTH: 35

```
<212> TYPE: DNA
<213> ORGANISM: Vaccinia virus

<400> SEQUENCE: 81 tttttatcg atatatacaa tgcattttta tatac                           35

<210> SEQ ID NO 82
<211> LENGTH: 30
<212> TYPE: DNA
<213> ORGANISM: Vaccinia virus

<400> SEQUENCE: 82 tttttggat ccagttctat cataatcatc                                 30
```